(12) United States Patent
Thomsen et al.

(10) Patent No.: US 7,354,722 B1
(45) Date of Patent: Apr. 8, 2008

(54) MODULATORS OF SMURF AND BMP/TGFβ SIGNALING PATHWAYS

(75) Inventors: Gerald H. Thomsen, Port Jefferson, NY (US); Jeffrey Wrana, Toronto (CA)

(73) Assignee: Signal Pharmaceuticals, San Diego, CA (US)

( * ) Notice: Subject to any disclaimer, the term of this patent is extended or adjusted under 35 U.S.C. 154(b) by 722 days.

(21) Appl. No.: 10/009,945

(22) PCT Filed: Jun. 12, 2000

(86) PCT No.: PCT/US00/16250

§ 371 (c)(1),
(2), (4) Date: Jun. 21, 2002

(87) PCT Pub. No.: WO00/77168

PCT Pub. Date: Dec. 21, 2000

Related U.S. Application Data

(60) Provisional application No. 60/138,969, filed on Jun. 11, 1999.

(51) Int. Cl.
*G01N 33/53* (2006.01)

(52) U.S. Cl. .......................... 435/7.1; 435/7.21; 435/4; 435/325; 435/7.2; 514/2; 530/350; 530/324; 530/300; 424/198.1

(58) Field of Classification Search ................ 530/350, 530/324, 300; 435/7.1, 7.21, 4, 325, 7.2; 514/2; 424/198.1
See application file for complete search history.

(56) References Cited

U.S. PATENT DOCUMENTS

| | | | | |
|---|---|---|---|---|
| 6,001,619 A | 12/1999 | Beach et al. | ................ | 435/193 |
| 6,060,262 A | 5/2000 | Beer-Romero et al. | ....... | 435/15 |
| 6,087,122 A | 7/2000 | Hustad et al. | ................ | 435/29 |
| 6,103,869 A | 8/2000 | Souchelnytokyi et al. | .. | 530/330 |

FOREIGN PATENT DOCUMENTS

WO    WO 97/12962    *   4/1997

OTHER PUBLICATIONS

Seffernick et al. (J. Bacteriology. vol. 183, pp. 2405-2410, 2001).*
Wells, (Biochemistry, vol. 29, pp. 8509-8517, 1990).*
Guo et al. (PNAS, vol. No. 25, pp. 9205-9210, 2004.*
JMB, vol. 282, pp. 933-946, Saleh et al., 1998.*
U.S. Appl. No. 09/385,198, filed Aug. 30, 1999, Hoekstra et al.
Afrakhte, et al. 1998. "Induction of Inhibitory Smad6 and Smad7 mRNA by TGF-β family members," Biochemical and Biophysical Research Communications 244: 505-511.
Baker, et al. 1996. "A novel mesoderm inducer, Madr2, functions in the activin signal transduction pathway," Genes & Development 10:1880-1889.
Bartel, et al. 1990. "The recognition component of the N-end rule pathway," EMBO Journal 9: 3179-3189.
Bartel, et al. 1995. "Analyzing protein-protein interactions using two-hybrid system," Methods in Enzymology, vol. 254, (24):1-263.
Bashirullah, et al. 1998. "RNA Localization in Development," Annu. Rev. Biochem. 67:335-94.
Bitzer, et al. 2000. "A mechanism of suppression of TGF-β/Smad signaling by NF-kB/Rel A," Genes & Development 14:187-197.
Bonifacino, et al. 1998. "Ubiquitin and the Control of Protein Fate in the Secretory and Endocytic Pathways," Ann. Rev. Cell. Biol. 14:19-57.
Chen, et al. 1995. "The WW domain of Yes-associated protein binds a proline-rich ligand that differs from the consensus established for Src homoloogy 3-binding modules," Proc. Natl. Acad. Sci. USA 82:7819-7823.
Chung, et al. 1998. "A novel, putative MEK kinase controls developmental timing and spatial paterning in Dictyostelium and is regulated by utiquitin-mediated protein degradation," Genes Dev. 12: 3564-78.
Coffman, T.M., 1997. "A genetic approach for studying the physiology of the Type 1A ($AT_{1A}$) Angiotensin Receptor," Seminars in Nephrology 17:404-411.
Derynck, et al., 1998, "Smads: Transcriptional Activators of TGF-β Responses," Cell 19:737-740
Dickson, B.J., 1998. "Photorecptor development: Breaking down the barriers," Current Biology 8:R90-R92.
Eppert, et al. 1996. "MADR2 Maps to 18q21 and encodes a TGFβ-Regulated MAD-Related protein that is functionally mutated in Colorectal Carcinoma," Cell 86: 543-552.
Epps, et al. 1998. "The Drosophila semushi mutation blocks nuclear import of Bicoid during embryogenesis," Current Biology 8:1277-1280.
Esther, Jr., et al. 1996. "Mice Lacking Angiotensin-Converting Enzyme Have Low Blood Pressure, Renal Pathology, and Reduced Male Fertility," Laboratory Investigation 74:953.

(Continued)

*Primary Examiner*—Hope Robinson
(74) *Attorney, Agent, or Firm*—Jones Day

(57) ABSTRACT

This invention provides unique members of the Hect family of ubiquitin ligases that specifically target BMP and TGFβ/activin pathway-specific Smads. The novel ligases have been named Smurf1 and Smurf2. They directly interact with Smads1 and 5 and Smad7, respectively, and regulate the ubiquitination, turnover and activity of Smads and other proteins of these pathways. Smurf1 interferes with biological responses to BMP, but not activin signaling. In amphibian embryos Smurf1 inhibits endogenous BMP signals, resulting in altered pattern formation and cell fate specification in the mesoderm and ectoderm. The present invention provides a unique regulatory link between the ubiquitination pathway and the control of cell fate determination by the TGFβ superfamily during embryonic development. Thus, Smurf1 is a negative regulator of Smad1 signal transduction, by targeting Smad1, Smurf1 blocks BMP signaling. In mammalian cells, Smurf2 suppresses TGFβ signalling, and in *Xenopus*, blocks formation of dorsal mesoderm and causes anterior truncation of the embryos. Smurf2 forms a stable complex with Smad7, which induces degradation and downregulation of TGFβ/activin signalling.

19 Claims, 47 Drawing Sheets

OTHER PUBLICATIONS

Fainsod, et al. 1994. "On the function of BMP-4 in patterning the marginal zone of the Xenopus embryo," Embo J 13:5015-25.

Gilboa, et al. 1998. "Oligomeric structure of Type I and Type II transforming growth Factor β Receptors: homodimers form in the ER and persist at the Plasma Membrane," J. Cell Biol. 140:767-777.

Govers, et al. 1999. "Identification of a novel ubiquitin conjugation motif, required for ligand-induced internalization of the growth hormone receptor," EMBO J. 18:28-36.

Graff, et al. 1996. "Xenopus Mad proteins transduce distinct subsets of signals for the TGFβ Superfamily," Cell 86:1-20.

Harland, et al. 1997. "Formation and function of Spemann's Organizer," Ann. Rev. Cell Biol. 13:611-667.

Harvey, et al. 1999. "Nedd4-like proteins: an emerging family of ubiquitin-protein ligases implicated in diverse cellular functions," Trends Cell Biol. 9:166-169.

Hayashi, et al. 1997. "The MAD-Related protein Smad7 Associates with TGFβ Receptor and Functions as an antagonist of TGFβ signaling," Cell 89:1165-1173.

Hein, et al. 1995. "NPI1, an essential yeast gene involved in induced degradation of Gap1 and Fur4 permeases, encodes the RspS ubiquitin-protein ligase," Mol. Microbiol. 18:77-87.

Heldin, et al. 1997. "TGF-β signalling from cell membrane to nucleus through SMAD proteins," Nature 390:465-71.

Hemmati-Brivanlou, et al. 1995. "Ventral mesodermal patterning in Xenopus Embryos: expression patterns and activities of BMP-2 and BMP-4," Dev. Genet. 17:78-89.

Hemmati-Brivanlou, et al. 1997. "Vertebrate Embryonic Cells will become nerve cells nnless told otherwise," Cell 88:13-17.

Henis, et al. 1994. "The Types II and III transforming growth Factor-β Receptors form Homo-Oligomers," J. Cell Biol. 126:139-154.

Hershko, et al. 1998. "The Ubiquitin System," Ann. Rev. Biochem. 67:425-479.

Hicke, L., 1999. "Gettin' down with ubiquitin: turning off cell-surface receptors, transporters and channels," Trends Cell Biol. 9:107-112.

Hochstrasser, M., 1996. "Ubiquitin-Dependent protein degradation," Ann. Rev. Genet. 30:405-439.

Hoodless, et al. 1996. "MADR1, a MAD-Related protein that functions in BMP2 signaling pathways", Cell 85:489-500.

Horb, et al. 1997. "A vegetally-localized T-box transcription factor in Xenopus eggs specifies mesoderm and endoderm and is essential for embryonic mesoderm formation," Dev. 124:1689-1698.

Huang, et al. 1995. "Control of cell fate by a deubiquitinating enzyme encoded by the fat facets gene," Science 270:1828-31.

Huibregtse, et al. 1995. "A family of proteins structurally and functionally related to the E6-AP ubiquitin-protein ligase," Proc. Natl. Acad. Sci. U.S.A. 92:2563-7.

Imamura, et al. 1997. "Smad6 inhibits signaling by the TGF-β superfamily," Nature 389:622-626.

Ishisaki, et al. 1998. "Smad7 is an activin-inducible inhibitor of activin-induced growth arrest and apoptosis in Mouse B Cells," J. Biol. Chem. 273:24293-24296.

Itoh, et al. 1998. "Transforming growth factor β1 induces nuclear export of inhibitory Smad7," J. Biol. Chem. 273:29195-29201.

Jiang, et al. 1998. "Regulation of the Hedgehog and Wingless signalling pathways by the F-box/WD40-repeat protein Slimb," Nature 391:493-6.

Joazeiro, et al. 1999. "The tyrosine kinase negative regulator c-Cb1 as a RING-Type, E2-Dependent ubiquitin-protein ligase," Science 286:309-312.

Jonk, et al. 1998. "Identification and fuctional characterization of a Smad binding element (SBE) in the JunB promoter that acts as a transforming growth Factor-β, activin, and bone morphogenetic protein-inducible enhancer," J. Biol. Chem. 273:21145.

Joseph, et al. 1998. "Mutant Vg1 ligands disrupt endoderm and mesoderm formation in Xenopus embryos," Development 125:2677-85.

Kawabata, et al. 1998. "Signal transduction by bone morphogenetic proteins," Cytokine Growth Factor Rev. 9:49-61.

Kimelman, et al. 1998. "Mesoderm Induction: A Postmodern View," Cell 94:419-21.

Kim, et al. 1997, "Drosophila Mad binds to DNA and directly mediates activation of vestigial by Decapentaplegic," Nature 388:304.

Kretzschmar, et al. 1997. "The TGF-β family mediator Smad1 is phosphorylated directly and activated functionally by the BMP receptor kinase," Genes Dev. 11:984-95.

Kumar, et al. 1997. "cDNA Cloning expression analysis, and mapping of the Mouse Nedd4 Gene," Genomics 40:435-43.

Kwon, et al. 1998. "The mouse and human genes encoding the recognition component of the N-end rule pathway," Proc. Natl. Acad. Sci. U.S.A. 95:7898-903.

Levkowitz, et al. 1999. "Ubiquitin ligase activity and tyrosine phosophorylation underlie suppression of growth factor signaling by c-Cb1/Sli-1," Mol. Cell 4:1029-1040.

Lindsay, et al. 1998. "A deubiquitinating enzyme that disassembles free polyubiquitin chains is required for development but not growth in dictyostelium," J. Bio. Chem. 273:24131-8.

Macias-Silva, et al. 1996. "MADR2 is a substrate of the TGFβ receptor and its phosphorylation is required for nuclear accumulation and signaling," Cell 87:1215-1224.

Macias-Silva, et al. 1998. "Specific activation of Smad1 signaling pathways by the BMP7 Type 1 Receptor, ALK2," J. Biol. Chem. 273:25628-36.

Massague, et al. 2000. "Controlling TGF-β signaling," Genes Deve. 14:627-644.

Massague, J., 1998. "TGF-β signal transduction," Ann. Rev. Biochem. 67:753-791.

Miyazono, K., 2000. "TGF-β signaling by Smad proteins," Cyto. Growth Factor Rev. 11:15-22.

Murakami, et al. 1996. "Hypertensive and Hypotensive Mice produced by the introduction and disruption of genes on the Renin-Angiotensin system," Blood Press. Suppl. 2:36.

Muralidhar, et al. 1993. "The Drosphila bendless gene encodes a neural protein related to ubiquitin-conjugating enzymes," Neuron 11:253-66.

Nakao, et al. 1997. "Identification Smad7, a TGFβ-inducible antagonist of TGF-β signalling," Nature 389:631-635.

Nalefski, et al. 1996. "The C2 domain calcium-binding motif: Structural and functional diversity," Protein Sci. 5:2375-2390.

Nefsky, et al. 1996. "Pub1 acts as an E6-AP-like protein ubiquitin ligase in the degradation of cdc25," Embo. J. 15:1301-1312.

Patton, et al. 1998. "Combinatorial control in ubiquitin-dependent proteolysis: don't Skp the F-box hypothesis," Trends, Genet, 14:236-243.

Plant, et al. 1997. "The c2 domain of the ubiquitin protein ligase Nedd4 mediates $Ca^{2+}$-dependent plasma membrane localization," J. Biol. Chem. 272:32329-36.

Pukatzki, et al. 1998. "novel component involved in ubiquitination is required for development of *Dictyostelium discoideum,*" J. Biol. Chem. 273:24131-8.

Reddi, A. H., 1998. "Role of morphogenetic proteins in skeletal tissue engineering and regeneration," Nature Biotech. 16:247-252.

Reeck, et al. 1987. "Homology" in proteins and nucleic acids: A terminology muddle and a way out of it, Cell 50:667.

Rotin, D., 1998. "WW (WWP) domains: From structure to function," Curr. Topics Microbiol. Immunol. 228-115-133.

Sasai, et al. 1997. "Ectodermal patterning in vertebrate embryos," Dev. Biol. 182:5-20.

Scheiffner, et al. 1993. "The HPV-16 E6 and E6-AP Complex functions as a ubiquitin-protein ligase in the ubiquitination of p53," cell 75:495-505.

Staub, et al. 1997. "Immunolocalization of the Ubiquitin-protein ligase Nedd4 in tissues expressing the epithelial $Na^+$ channel (EnaC)," Am. J Physiol. 272:C1871-80.

Staub, et al. 2000. "Regulation of stability and function of the epithelial $Na^+$ channel (EnaC) by utiquitination," Kidney Int. 57:809-815.

Staub, et al. 1997. "Regulation of the epithelial $Na^+$ channel by Nedd4 and ubiquitination," EMBO J 16:6325-6336.

Staub, et al. 1996. "WW domains," Structure 4:495-499.

Staub, et al. 1996. "WW domains of Nedd4 bind to the proline-rich PY motifs in the epithelial $Na^+$ channel deleted in Liddle's syndrome," EMBO J. 15:2371-2380.

Suzuki, et al. 1997. "Smad5 induces ventral fates in Xenopus embryo," Dev. Biol. 184:402-405.

Takase, et al. 1998. "Induction of Smad6 mRNA by bone morphogenetic proteins," Biochem. Biophys. Res. Commun. 244:26-29.

Thomsen, G.H., 1997. "Antagonism within and around the organizer: BMP inhibitors in vertebrate body patterning," Trends Genet. 13:209-211.

Thomsen, G.H., 1996. "Xenopus mothers against decapentaplegic is an embryonic ventralizing agent that acts downstream of the BMP-2/4 receptor," Development 122:2359-66.

Tsukazaki, et al. 1998. "SARA, a FYVE domain protein that recruits Smad2 to the TGFβ receptor," Cell 95:799-791.

Ulloa, et al. 1999. "Inhibition of transforming growth factor-β/SMAD signalling by the interferon-γ/STAT pathway," Nature 397:710-713.

van Kerkhof, et al. 2000. "Endocytosis and degradation of the growth hormone receptor are proteasome-dependent," J. Biol. Chelm. 275:1575-1580.

Wang, , et al. 1999. "Functional domains of the Rsp5 Ubiquitin-protein ligase," Mol. Cell Biol. 19:342-52.

Whitman, M., 1998. "Smads and early developmental signaling by the TGFβ superfamily," Genes and Dev. 12:2445-2462.

Wigler, et al. 1979. "Transformation of mamalian cells with genes from procaryotes and eucaryotes," Cell 16:777-785.

Wilson, et al. 1997. "Concentration-dependent patterning of the Xenopus ectoderm by BMP4 and its signal transducer Smad1," Dev. 124:3177-3184.

Wrana, et al. 2000. "Regulation of Smad activity," Cell 100:189-192.

Wrana, et al. 2000. "The Smad pathway," Cytokine & Growth Factor Reviews 11:5-13.

* cited by examiner

FIG. 1A

| | | |
|---|---|---|
| SMURF1 | 1 | MSNVVTRRGGSSIRVRLTVLCAKNLAKRD |
| hSMURF1 | - | ----GGSSIRLTVLCAKNLAKKP |
| PUB1 | 1 | MSNSAQSR----RIRVIIVADGLYKRD |
| | | |
| SMURF1 | 61 | KWNQHYDLYVGKMDSITISIWNHKKIHKK |
| hSMURF1 | 61 | KWNQHYDLYVGKTDSITISYWNHKKIHKK |
| PUB1 | 55 | YWNETFEVNVTDNSTIAHQMFDQKKFKKK |
| | | |
| SMURF1 | 121 | LNPTDNDAVRGQITVSLQTRDRIGTLGSV |
| hSMURF1 | 121 | LNPSDTDAVRGQIVVSLQTRQRIGTGSV |
| PUB1 | 114 | KKSNEKTVHGKIINLSTTAQSTLQVPS |
| | | |
| SMURF1 | 174 | CFMDEPAPYTDGPGAAGGGPGRLVESPG |
| hSMURF1 | 174 | CFMEEPARYTDSTGAAGGGNGRFVESPS |
| PUB1 | 174 | SRAGSPTRDNAPAASPASSEPRTESSFEP |
| | | |
| SMURF1 | 216 | VREHVQTPQ NRSHGF |
| hSMURF1 | 217 | VRGSLQTPQ NRPHGH |
| PUB1 | 234 | IRPNLSSVAGAAAAELHSSASSANVTEGV |
| | | |
| SMURF1 | 239 | YEQRTTVQGQVYFLHTQTGVSTWHDPR |
| hSMURF1 | 240 | YEQRTTVQGQVYFLHTQTGVSTWHDPR |
| PUB1 | 294 | WEQRYIPEGRPYFVDHNERTTWVDPRRQ |
| | | |
| SMURF1 | 288 | RTTVSGRIYFVDHNNRTTQFTDPRLHHI |
| hSMURF1 | 289 | RSTVSGRIYFVDHNNRTTQFTDPRLHHM |
| PUB1 | 354 | RLNTARVYFVDHNTKTITWDDPRLPSSL |

FIG. 1B

```
SMURF1    348  YERDLVQKLKVLRHELSLLQPQAGHCRVE
hSMURF1   348  YERDLVQKLKVLRHELSLLQPQAGHCRIE
PUB 1     389  YKRDFRRKLKYFLSQPALHRLPGQHIK

SMURF1    408  GEEGLDYGGVAREWLYLLCHEMLNPYYGL
hSMURF1   408  GEEGLDYGGVAREWLYLLCHEMLNPYYGL
PUB 1     448  GEDGLDYGGLSREYFLLSHEMFNPFYCL

SMURF1    468  RIMGLAVFHGHYINGGFTVPFYKQLLGKP
hSMURF1   468  RIMGLAVFHGHYINGGFTVPFYKQLLGKP
PUB 1     508  RVIGAIFHRRFVDAFEVMSFYKMILQKK

SMURF1    528  TFCVEHNAFGRLLQHELKPNGKNLQVTEE
hSMURF1   528  TECVEHNAFGRILQHELKPNGRNVPVTEE
PUB 1     568  TFSVEDNCFGEVVTIDLKPNGRNIEVTEE

SMURF1    588  LIPQHLLKPFEQKELELTIGGLDKLDISD
hSMURF1   588  LIPQHLLKPFDQKELELTIGGLDKIDLND
PUB 1     627  LIPQELLINVFDERELELLIGGISEIDMEQ

SMURF1    648  RARLLQFVTGSTRVPLQGFKALQGSTGAA
hSMURF1   648  RARLLQFVTGSTRVPLQGFKALQGSTGAA
PUB 1     687  KSRLLQFTIGTSRIPVNGFKDLQGSD

SMURF1    708  YESYEKLYEKLLTAVEETIS       731
hSMURF1   708  YEEKLYEKLLTAVEETCGFAVE     731
PUB 1     743  YTSKKDLDHKLSIAVEETIGFGQE   766
```

FIG. IC

```
VSREEIFEESYRQIMKRPKDLKKRLMVKFR 407
VSREEIFEESYRQIMKRPKDLKKRLMVKFR 407
VRRNHIFEDSIAEIMRQSATDLKKRLMIKFD 447

FQYSTDNIYTLQINPDSSINPDHLSYFHFVG 467
FQYSTDNIYMLQINPDSSINPDHLSYFHFVG 467
FEYSVDNYTLQINPHSGINPEHLNYFKFIG 507

IQLSDLESVDPELHKSLVWILENDITSVLDH 527
IQLSDLESVDPELHKSLVWILENDITPVLDH 527
VTLQDMESMDAEYYRSLVWILDNDLTGVLDL 567

NKKEYVRLYVNWRFMRGIEAQFLALQKGFNE 587
NKKEYVRLYVNWRFMRGIEAQFLALQKGFNE 587
NKREYVDLVTVWIQKRIEFQNAFHEGFSE 626

WKANTRLKHCLANSNIVQWFWQAVESFDEER 647
WKSNTRLKHCVADSNIVRWFWQAVETFDEER 647
WKKHKDYRSYSENDQIIKWFWELMDEWSNEK 686

GPRLFTIHLIDANTDNLPKAHTCFNRIDIPP 707
GPRLFTIHLIDANTDNCPKAHTCFNRIDIPP 707
GPRKFIIEKAGEPNKLPKAHTCFNRIDLPP 742
```

FIG. 1D

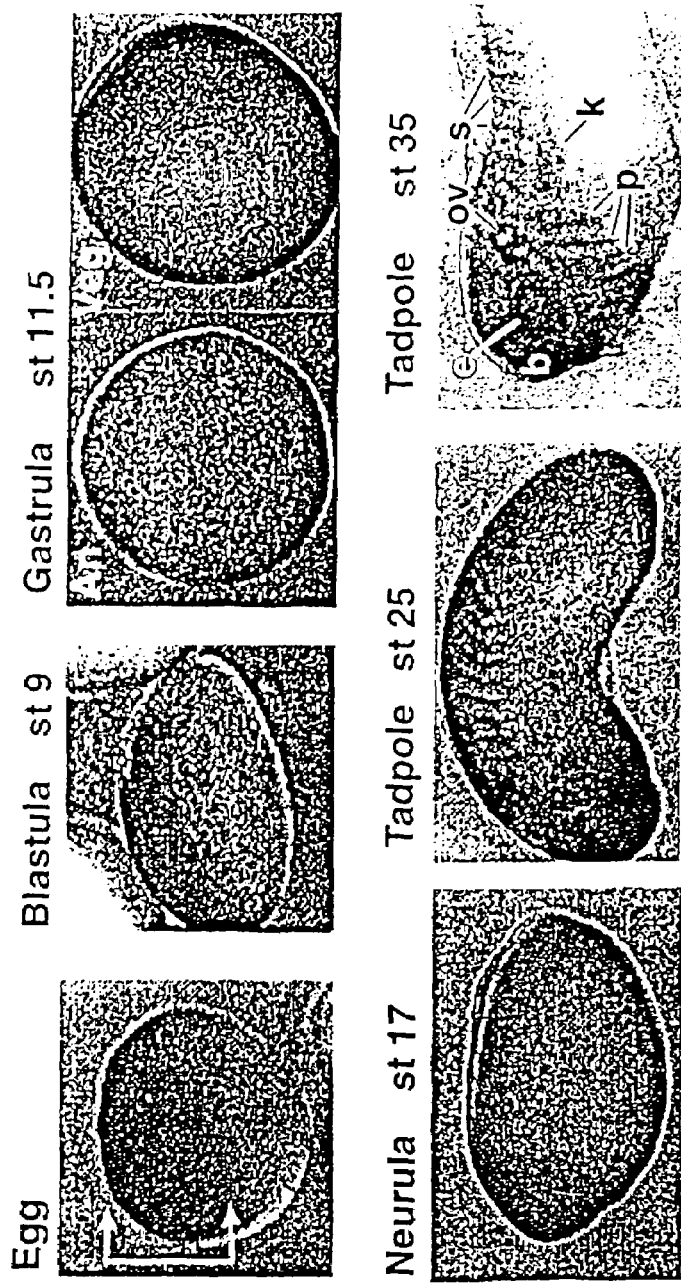

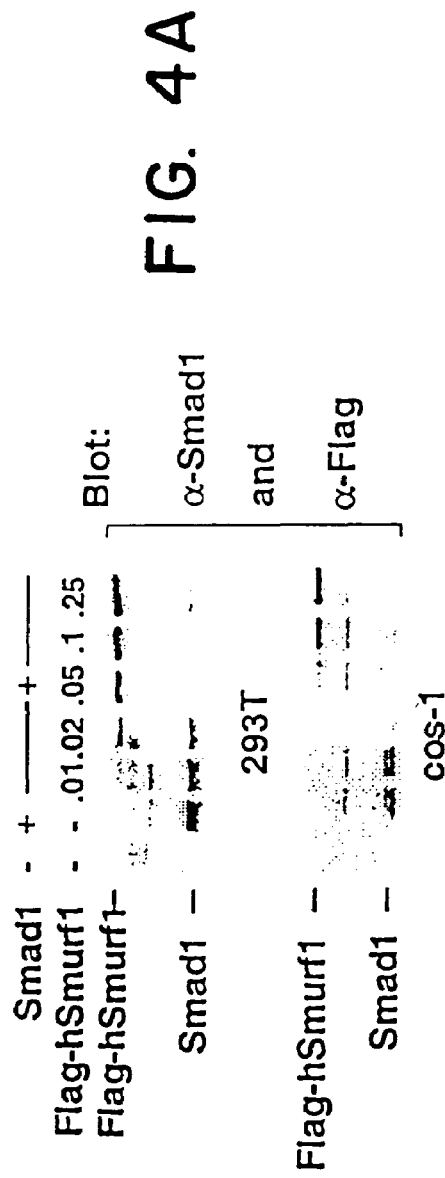

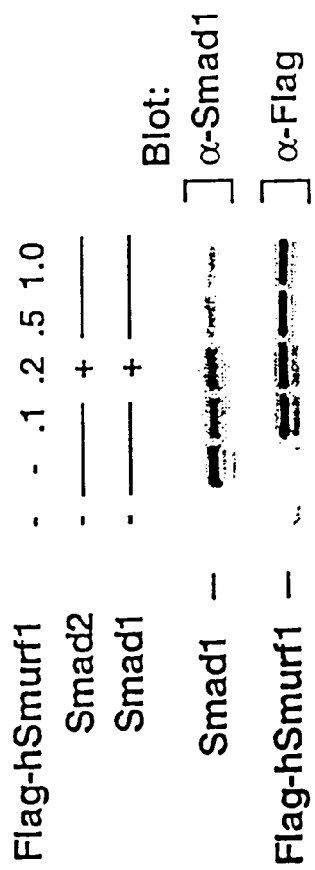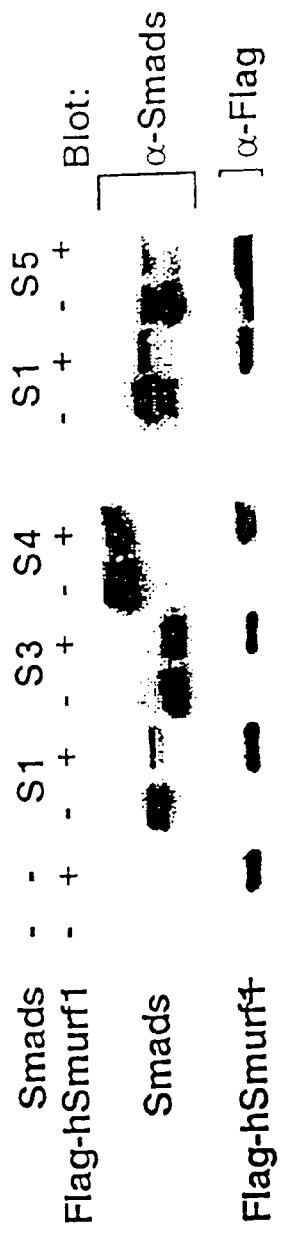
FIG. 4C
FIG. 4D

FIG. 9A

```
         10          20          30          40          50
          *           *           *           *           *
GGAGGCTCCA  GCATCAAGAT  CCGTCTGACA  GTGTTATGTG  CCAAGAACCT 60          70          80          90         100
          *           *           *           *           *
TGCAAAGAAA  GACTTCTTCA  GGCTCCCTGA  CCCTTTTGCA  AAGATTGTCG 110         120         130         140         150
          *           *           *           *           *
TGGATGGGTC  TGGGCAGTGC  CACTCAACCG  ACACTGTGAA  AAACACATTG 160         170         180         190         200
          *           *           *           *           *
GACCCAAAGT  GGAACCAGCA  CTATGATCTA  TATGTTGGGA  AAACGGATTC 210         220         230         240         250
          *           *           *           *           *
GATAACCATT  AGCGTGTGGA  ACCATAAGAA  AATTCACAAG  AAACAGGGAG 260         270         280         290         300
          *           *           *           *           *
CTGGCTTCCT  GGGCTGTGTG  CGGCTGCTCT  CCAATGCCAT  CAGCAGATTA 310         320         330         340         350
          *           *           *           *           *
AAAGATACCG  GATACCAGCG  TTTGGATCTA  TGCAAACTAA  ACCCCTCAGA 360         370         380         390         400
          *           *           *           *           *
TACTGATGCA  GTTCGTGGCC  AGATAGTGGT  CAGTTTACAG  ACACGAGACA
A─────────  ──  ──────  ──────────  ──  ──────  ─────────A
```

```
       410        420        430        440        450
        *          *          *          *          *
   GAATAGGAAC CGGCGGCTCG GTGGTGGACT GCAGAGGACT GTTAGAAAAT 460        470        480        490        500
        *          *          *          *          *
   GAAGGAACGG TGTATGAAGA CTCCGGGCCT GGGAGGCCGC TCAGCTGCTT 510        520        530        540        550
        *          *          *          *          *
   CATGGAGGAA CCAGCCCCTT ACACAGATAG CACCGGTGCT GCTGCTGGAG 560        570        580        590        600
        *          *          *          *          *
   GAGGGAATTG CAGGTTCGTG GAGTCCCCAA GTCAAGATCA AAGACTTCAG 610        620        630        640        650
        *          *          *          *          *
   GCACAGCGGC TTCGAAACCC TGATGTGCGA GGTTCACTAC AGACGCCCCA 660        670        680        690        700
        *          *          *          *          *
   GAACCGACCA CACGGCCACC AGTCCCCGGA ACTGCCCGAA GGCTACGAAC 710        720        730        740        750
```

```
B─────────────────────────────────────────────────────────────B
     *          *          *          *          *
AAAGAACAAC AGTCCAGGGC CAAGTTTACT TTTTGCATAC ACAGACTGGA 760        770        780        790        800
     *          *          *          *          *
GTTAGCACGT GGCACGACCC CAGGATACCA AGAGACCTTA ACAGTGTGAA 810        820        830        840        850
     *          *          *          *          *
CTGTGATGAA CTTGGACCAC TGCCGCCAGG CTGGGAAGTC AGAAGTACAG 860        870        880        890        900
     *          *          *          *          *
TTTCTGGGAG GATATATTTT GTAGATCATA ATAACCGAAC AACCCAGTTT 910        920        930        940        950
     *          *          *          *          *
ACAGACCCAA GGTTACACCA CATCATGAAT CACCAGTGCC AACTCAAGGA 960        970        980        990       1000
     *          *          *          *          *
GCCCAGCCAG CCGCTGCCAC TGCCCAGTGA GGGCTCTCTG GAGGACGAGG 1010       1020       1030       1040       1050
     *          *          *          *          *
AGCTTCCTGC CCAGAGATAC GAAAGAGATC TAGTCCAGAA GCTGAAAGTC 1060       1070       1080       1090       1100
     *          *          *          *          *
CTCAGACACG AACTGTCGCT TCAGCAGCCC CAAGCTGGTC ATTGCCGCAT
C─────────────────────────────────────────────────────────────C
```

```
    1110        1120        1130        1140        1150
     *           *           *           *           *
CGAAGTGTCC  AGAGAAGAAA  TCTTTGAGGA  GTCTTACCGC  CAGATAATGA 1160        1170        1180        1190        1200
     *           *           *           *           *
AGATGCGACC  GAAAGACTTG  AAAAAACGGC  TGATGGTGAA  ATTCCGTGGG 1210        1220        1230        1240        1250
     *           *           *           *           *
GAAGAAGGTT  TGGATTACGG  TGGTGTGGCC  AGGGAGTGGC  TTTACTTGCT 1260        1270        1280        1290        1300
     *           *           *           *           *
GTGCCATGAA  ATGCTGAATC  CTTATTACGG  GCTCTTCCAG  TATTCTACGG 1310        1320        1330        1340        1350
     *           *           *           *           *
ACAATATTTA  CATGTTGCAA  ATAAATCCGG  ATTCTTCAAT  CAACCCCGAC 1360        1370        1380        1390        1400
     *           *           *           *           *
CACTTGTCTT  ATTTCCACTT  TGTGGGGCGG  ATCATGGGGC  TGGCTGTGTT 1410        1420        1430        1440        1450
     *           *           *           *           *
```

| CCATGGACAC | TACATCAACG | GGGGCTTCAC | AGTGCCCTTC | TACAAGCAGC |
|---|---|---|---|---|
| 1460 | 1470 | 1480 | 1490 | 1500 |
| * | * | * | * | * |
| TGCTGGGGAA | GCCCATCCAG | CTCTCAGATC | TGGAATCTGT | GGACCCAGAG |
| 1510 | 1520 | 1530 | 1540 | 1550 |
| * | * | * | * | * |
| CTGCATAAGA | GCTTGGTGTG | GATCCTAGAG | AACGACATCA | CGCCTGTACT |
| 1560 | 1570 | 1580 | 1590 | 1600 |
| * | * | * | * | * |
| GGACCACACC | TTCTGCGTGG | AACACAACGC | CTTCGGGCGG | ATCCTGCAGC |
| 1610 | 1620 | 1630 | 1640 | 1650 |
| * | * | * | * | * |
| ATGAACTGAA | ACCCAATGGC | AGAAATGTGC | CAGTCACAGA | GGAGAATAAG |
| 1660 | 1670 | 1680 | 1690 | 1700 |
| * | * | * | * | * |
| AAAGAATACG | TCCGGTTGTA | TGTAAACTGG | AGGTTTATGA | GAGGAATCGA |
| 1710 | 1720 | 1730 | 1740 | 1750 |
| * | * | * | * | * |
| AGCCCAGTTC | TTAGCTCTGC | AGAAGGGGTT | CAATGAGCTC | ATCCCTCAAC |
| 1760 | 1770 | 1780 | 1790 | 1800 |
| * | * | * | * | * |
| ATCTGCTGAA | GCCTTTTGAC | CAGAAGGAAC | TGGAGCTGAT | CATAGGCGGC |

```
   1810        1820        1830        1840        1850
    *           *           *           *           *
CTGGATAAAA  TAGACTTGAA  CGACTGGAAG  TCGAACACGC  GGCTGAAGCA 1860        1870        1880        1890        1900
    *           *           *           *           *
CTGTGTGGCC  GACAGCAACA  TCGTGCGGTG  GTTCTGGCAA  GCGGTGGAGA 1910        1920        1930        1940        1950
    *           *           *           *           *
CGTTCGATGA  AGAAAGGAGG  GCCAGGCTCC  TGCAGTTTGT  GACTGGGTCC 1960        1970        1980        1990        2000
    *           *           *           *           *
ACGCGAGTCC  CGCTCCAAGG  CTTCAAGGCT  TTGCAAGGTT  CTACAGGCGC 2010        2020        2030        2040        2050
    *           *           *           *           *
GGCAGGGCCC  CGGCTGTTCA  CCATCCACCT  GATAGACGCG  AACACAGACA 2060        2070        2080        2090        2100
    *           *           *           *           *
ACCTTCCGAA  GGCCCATACC  TGCTTTAACC  GGATCGACAT  TCCACCATAT 2110        2120        2130        2140        2150
    *           *           *           *           *
GAGTCCTATG  AGAAGCTCTA  CGAGAAGCTG  CTGACAGCCG  TGGAGGAGAC 2160        2170
    *           *
CTGCGGGTTT  GCTGTGGAGT  AA
```

FIG. 10A

```
         10         20         30         40         50
         *          *          *          *          *
GGSSIKIRLT VLCAKNLAKK DFFRLPDPFA KIVVDGSGQC HSTDTVKNTL
         60         70         80         90        100
         *          *          *          *          *
DPKWNQHYDL YVGKTDSITI SVWNHKKIHK KQGAGFLGCV RLLSNAISRL
        110        120        130        140        150
         *          *          *          *          *
KDTGYQRLDL CKLNPSDTDA VRGQIVVSLQ TRDRIGTGGS VVDCRGLLEN
        160        170        180        190        200
         *          *          *          *          *
EGTVYEDSGP GRPLSCFMEE PAPYTDSTGA AAGGNCRFV ESPSQDQRLQ
        210        220        230        240        250
         *          *          *          *          *
AQRLRNPDVR GSLQTPQNRP HGHQSPELPE GYEQRTTVQG QVYFLHTQTG
```

```
         260        270        280        290        300
          *          *          *          *          *
VSTWHDPRIP RDLNSVNCDE LGPLPPGWEV RSTVSGRIYF VDHNNRTTQF
         310        320        330        340        350
          *          *          *          *          *
TDPRLHHIMN HQCQLKEPSQ PLPLPSEGSL EDEELPAQRY ERDLVQKLKV
         360        370        380        390        400
          *          *          *          *          *
LRHELSLQQP QAGHCRIEVS REEIFEESYR QIMKMRPKDL KKRLMVKFRG
         410        420        430        440        450
          *          *          *          *          *
EEGLDYGGVA REWLYLLCHE MLNPYYGLFQ YSTDNIYMLQ INPDSSINPD
         460        470        480        490        500
          *          *          *          *          *
HLSYFHFVGR IMGLAVFHGH YINGGFTVPF YKQLLGKPIQ LSDLESVDPE
```

FIG. 10C

```
         510        520        530        540        550
          *          *          *          *          *
    LHKSLVWILE NDITPVLDHT FCVEHNAFGR ILQHELKPNG RNVPVTEENK
         560        570        580        590        600
          *          *          *          *          *
    KEYVRLYVNW RFMRGIEAQF LALQKGFNEL IPQHLLKPFD QKELELIIGG
         610        620        630        640        650
          *          *          *          *          *
    LDKIDLNDWK SNTRLKHCVA DSNIVRWFWQ AVETFDEERR ARLLQFVTGS
         660        670        680        690        700
          *          *          *          *          *
    TRVPLQGFKA LQGSTGAAGP RLFTIHLIDA NTDNLPKAHT CFNRIDIPPY
         710        720
          *          *
    ESYEKLYEKL LTAVEETCGF AVE*
```

FIG. 11A

```
            10         20         30         40         50
            *          *          *          *          *
ATGTCTAACC CCGGACGCCG GAGGAACGGG CCCGTCAAGC TGCGCCTGAC 60         70         80         90        100
            *          *          *          *          *
AGTACTCTGT GCAAAAAACC TGGTGAAAAA GGATTTTTTC CGACTTCCTG 110        120        130        140        150
            *          *          *          *          *
ATCCATTTGC TAAGGTGGTG GTTGATGGAT CTGGGCAATG CCATTCTACA 160        170        180        190        200
            *          *          *          *          *
GATACTGTGA AGAATACGCT TGATCCAAAG TGGAATCAGC ATTATGACCT 210        220        230        240        250
            *          *          *          *          *
GTATATTGGA AAGTCTGATT CAGTTACGAT CAGTGTATGG AATCACAAGA 260        270        280        290        300
            *          *          *          *          *
AGATCCATAA GAAACAAGGT GCTGGATTTC TCGGTTGTGT TCGTCTTCTT
```

FIG. 11B

```
         310        320        330        340        350
          *          *          *          *          *
    TCCAATGCCA TCAACCGCCT CAAAGACACT GGTTATCAGA GGTTGGATTT 360        370        380        390        400
          *          *          *          *          *
    ATGCAAACTC GGGCCAAATG ACAATGATAC AGTTAGAGGA CAGATAGTAG 410        420        430        440        450
          *          *          *          *          *
    TAAGTCTTCA GTCCAGAGAC CGAATAGGCA CAGGAGGACA AGTTGTGGAC 460        470        480        490        500
          *          *          *          *          *
    TGCAGTCGTT TATTGATAA CGATTTACCA GACGGGCTGGG AAGAAAGGAG 510        520        530        540        550
          *          *          *          *          *
    AACCGCCTCT GGAAGAATCC AGTATCTAAA CCATATAACA AGAACTACGC 560        570        580        590        600
          *          *          *          *          *
    AATGGGAGCG CCCAACACGA CCGGCATCCG AATATTCTAG CCCTGGCAGA
```

FIG. IIC

```
          610        620        630        640        650
           *          *          *          *          *
     CCTCTTAGCT GCTTTGTTGA TGAGAACACT CCAATTAGTG GAACAAATGG
          660        670        680        690        700
           *          *          *          *          *
     TGCAACATGT GGACAGTCTT CAGATCCCAG GCTGGCAGAG AGGAGAGTCA
          710        720        730        740        750
           *          *          *          *          *
     GGTCACAACG ACATAGAAAT TACATGAGCA GAACACATTT ACATACTCCT
          760        770        780        790        800
           *          *          *          *          *
     CCAGACCTAC CAGAAGGCTA TGAACAGAGG ACAACGCAAC AAGGCCAGGT
          810        820        830        840        850
           *          *          *          *          *
     GTATTTCTTA CATACACAGA CTGGTGTGAG CACATGGCAT GATCCAAGAG
          860        870        880        890        900
           *          *          *          *          *
     TGCCCAGGGA TCTTAGCAAC ATCAATTGTG AAGAGCTTGG.TCCATTGCCT
```

FIG. IID

```
     910        920        930        940        950
      *          *          *          *          *
CCTGGATGGG AGATCCGTAA TACGGCAACA GGCAGAGTTT ATTTCGTTGA 960        970        980        990       1000
      *          *          *          *          *
CCATAACAAC AGAACAACAC AATTTACAGA TCCTCGGCTG TCTGCTAACT 1010       1020       1030       1040       1050
      *          *          *          *          *
TGCATTTAGT TTTAAATCGG CAGAACCAAT TGAAAGACCA ACAGCAACAG 1060       1070       1080       1090       1100
      *          *          *          *          *
CAAGTGGTAT CGTTATGTCC TGATGACACA GAATGCCTGA CAGTCCCAAG 1110       1120       1130       1140       1150
      *          *          *          *          *
GTACAAGCGA GACCTGGTTC AGAAACTAAA AATTTTGCGG CAAGAACTTT 1160       1170       1180       1190       1200
      *          *          *          *          *
CCCAACAACA GCCTCAGGCA GGTCATTGCC GCATTGAGGT TTCCAGGAA
```

FIG. 11E

```
       1210       1220       1230       1240       1250
         *          *          *          *          *
GAGATTTTTG AGGAATCATA TCGACAGGTC ATGAAAATGA GACCAAAAGA 1260       1270       1280       1290       1300
         *          *          *          *          *
TCTCTGGAAG CGATTAATGA TAAAATTTCG TGGAGAAGAA GGCCTTGACT 1310       1320       1330       1340       1350
         *          *          *          *          *
ATGGAGGCGT TGCCAGGGAA TGGTTGTATC TCTTGTCACA TGAAATGTTG 1360       1370       1380       1390       1400
         *          *          *          *          *
AATCCATACT ATGGCCTCTT CCAGTATTCA AGAGATGATA TTTATACATT 1410       1420       1430       1440       1450
         *          *          *          *          *
```

FIG. 11F

```
GCAGATCAAT CCTGATTCTG CAGTTAATCC GGAACATTTA TCCTATTTCC
        1460       1470       1480       1490       1500
           *          *          *          *          *
ACTTTGTTGG ACGAATAATG GGAATGGCTG TGTTTCATGG ACATTATATT
        1510       1520       1530       1540       1550
           *          *          *          *          *
GATGGTGGTT TCACATTGCC TTTTTATAAG CAATTGCTTG GGAAGTCAAT
        1560       1570       1580       1590       1600
           *          *          *          *          *
TACCTTGGAT GACATGGAGT TAGTAGATCC GGATCTTCAC AACAGTTTAG
        1610       1620       1630       1640       1650
           *          *          *          *          *
TGTGGATACT TGAGAATGAT ATTACAGGTG TTTTGGACCA TACCTTCTGT
        1660       1670       1680       1690       1700
           *          *          *          *          *
GTTGAACATA ATGCATATGG TGAAATTATT CAGCATGAAC TTAAACCAAA
        1710       1720       1730       1740       1750
           *          *          *          *          *
TGGCAAAAGT ATCCCTGTTA ATGAAGAAAA TAAAAAAGAA TATGTCAGGC
```

FIG. 11G

```
        1760       1770       1780       1790       1800
          *          *          *          *          *
TCTATGTGAA CTGGAGATTT TTACGAGGCA TTGAGGCTCA ATTCTTGGCT 1810       1820       1830       1840       1850
          *          *          *          *          *
CTGCAGAAAG GATTTAATGA AGTAATTCCA CAACATCTGC TGAAGACATT 1860       1870       1880       1890       1900
          *          *          *          *          *
TGATGAGAAG GAGTTAGAGC TCATTATTTG TGGACTTGGA AAGATAGATG 1910       1920       1930       1940       1950
          *          *          *          *          *
TTAATGACTG GAAGGTAAAC ACCCGGTTAA AACACTGTAC ACCAGACAGC 1960       1970       1980       1990       2000
          *          *          *          *          *
AACATTGTCA AATGGTTCTG GAAAGCTGTG GAGTTTTTTG ATGAAGAGCG 2010       2020       2030       2040       2050
          *          *          *          *          *
ACGAGCAAGA TTGCTTCAGT TTGTGACAGG ATCCTCTCGA GTGCCTCTGC
```

FIG. 11H

```
         2060       2070       2080       2090       2100
          *          *          *          *          *
     AGGGCTTCAA AGCATTGCAA GGTGCTGCAG GCCCGAGACT CTTTACCATA
         2110       2120       2130       2140       2150
          *          *          *          *          *
     CACCAGATTG ATGCCCTGCAC TAACAACCTG CCGAAAGCCC ACACTTGCTT
         2160       2170       2180       2190       2200
          *          *          *          *          *
     CAATCGAATA GACATTCCAC CCTATGAAAG CTATGAAAAG CTATATGAAA
         2210       2220       2230       2240
          *          *          *          *
     AGCTGCTAAC AGCCATTGAA GAAACATGTG GATTGCTGT GGAATGA
```

FIG. 12

```
MSNPGRRRNGPVKLRLTVLCARNLVKKDFFRLPDFFAKVVVDGSGQCHS      49
TDTVKNTLDPKWNQHYDLYIGKSDSVTISVWNHKKIHKKQGAGFLGCVR      98
LLSNAINRLKDTGYQRLDLCKLGPNDNDTVRGQIVVSLQSRDRIGTGGQ     147
VVDCSRLFDNDLPDGWEERRTASGRTQMENHTTRTIQWERPTRPASEYS     196
                   WW1
SPGRPLSCFVDENTPISGTNGATCGQSSDPRLAERRVRSQRHRNYMSRT     245
HLHTPPDLPEGYEQRLTQQGQVYFLHLQTGVSTWEDPRVPRDLSNINCE     294
               WW2
ELGPLPPGWEERNTATGRVVFVDHNNRTLQETDPRLSANLHLVLNRQNQ     343
         WW3
LKDQQQQQVVSLCPDDTECLTVPRYKRDLVQKLKILRQELSQQQPQAGH     392
CRIEVSREEIFEESYRQVMKRPKDLWKRLMIKFRGEEGLDYGGVAREW      441
LYLLSHEMLNPYYGLFQYSRDDIYTLQINPDSAVNPEHLSYFHFVGRIM     490
GMAVFHGHYIDGGFTLPFYKQLLGKSITLDDMELVDPDLHNSLVWILEN     539
DITGVLDHTFCVEHNAYGEIIQHELKPNGKSIPVNEENKKEYVRLYVNW     588
RFLRGIEAQFLALQKGFNEVIPQHLLKTFDEKELELICGLGKIDVNDW      637
KVNTRLKHCTPDSNIVKWFWKAVEFFDEERRARLLQFVTGSSRVPLQGF     686
KALQGAAGPRLFTIHQIDACTNNLPKAHTCFNRIDIPPYESYEKLYEKL     735
LTALEETCGFAVE      748
```

FIG. 15E

Smad7 ...²⁰⁴LESPPPPYSRY²¹⁴...
Smad7(Y211A) ... LESPPPPASRY ...
Smad7ΔPY ... LES-----SRY ...

Smad7: - WT YA ΔPY
Flag-Smurf2: ——WT——

Blot:
Smad7-HA [ ▪▪▪▪ ] anti-Smad7

Flag-Smurf2 — ▪▪▪▪ ] anti-Flag

IP: anti-Flag

Smad7-HA [ ▪▪▪ ] anti-HA

Totals

FIG. 15F

Smurf2: - WT ΔWW1 ΔWW2 ΔWW3
Smad7-HA: - ——— + ——— Blot:

Smad7-HA — ▪▪ ] anti-HA

Flag-Smurf2 [ ▪ — ▪ ▪ ] anti-Flag

IP: anti-Flag

Smad7-HA — ▪▪▪▪ ] anti-HA

Totals

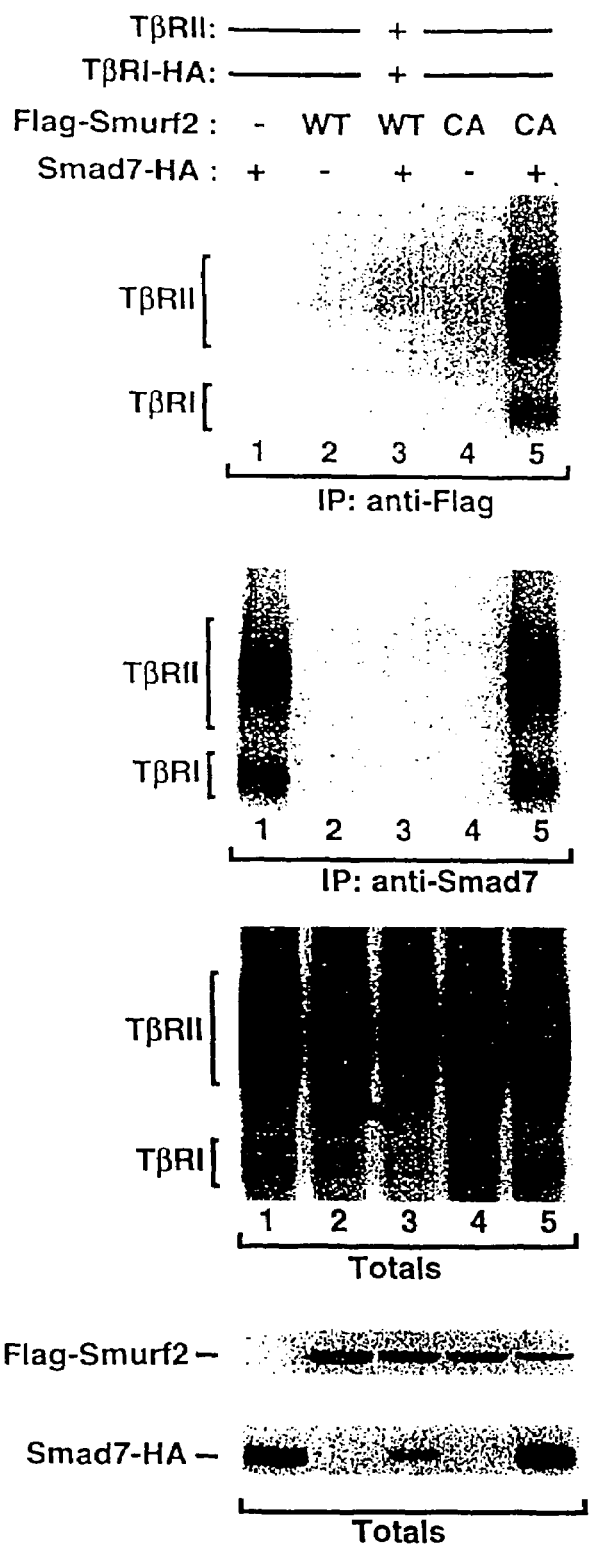

FIG. 17C1
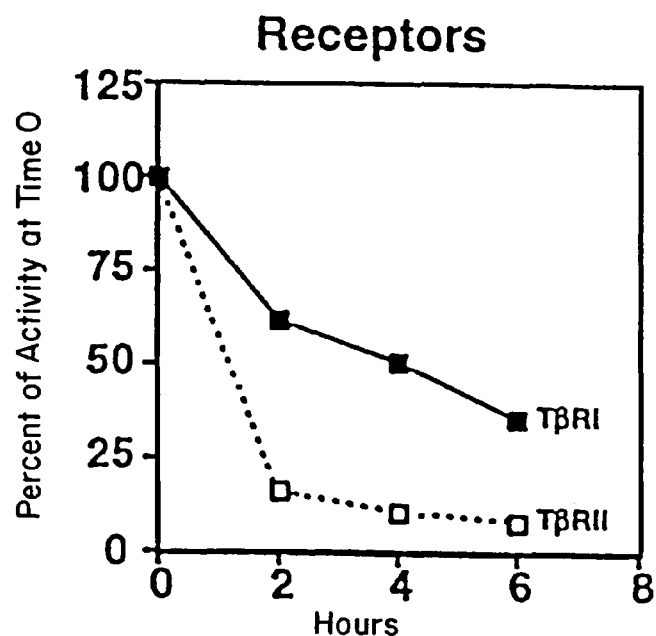
FIG. 17C2
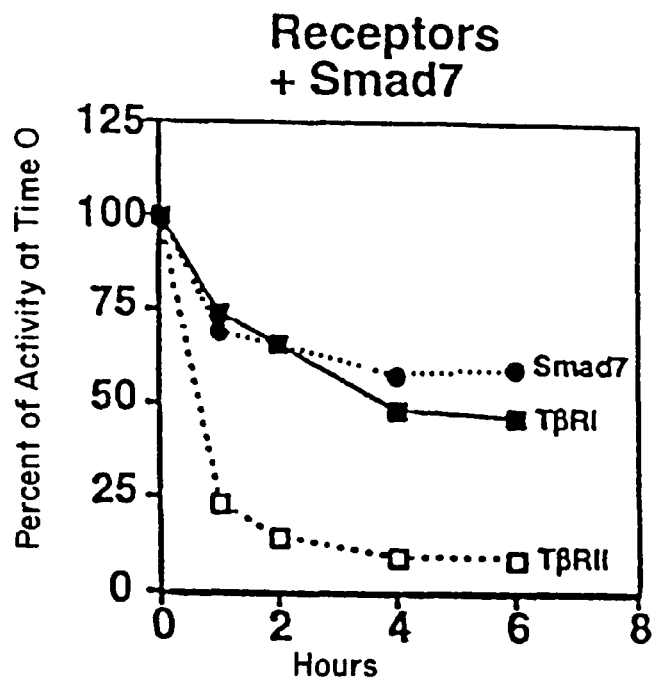

FIG. 17C3
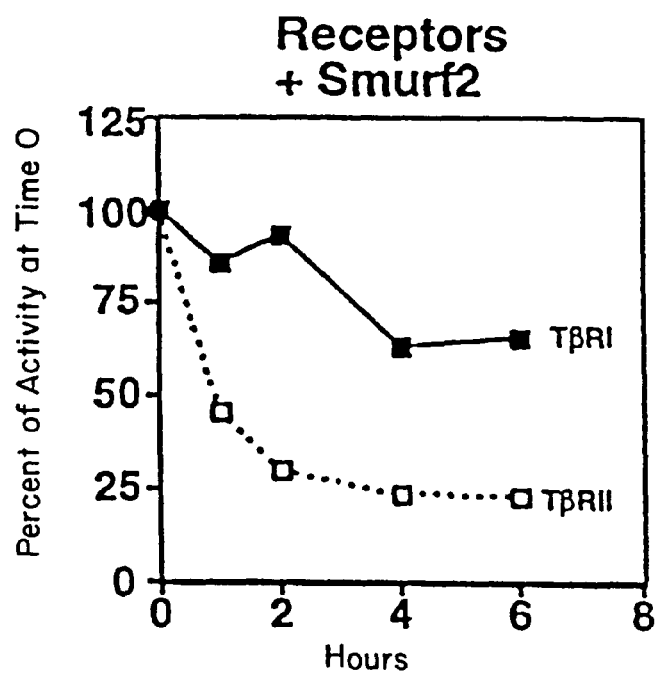
FIG. 17C4
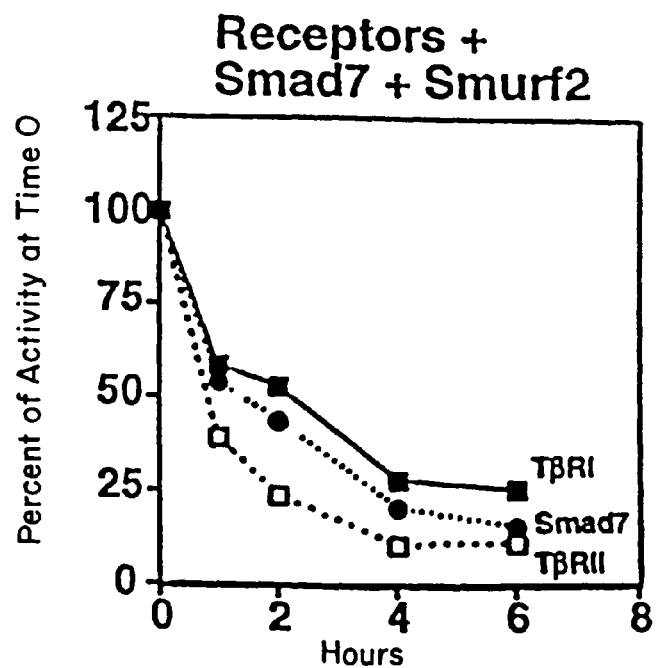

MODULATORS OF SMURF AND BMP/TGFβ SIGNALING PATHWAYS

This application claims priority to PCT International Application No. PCT/US00/16250, filed on Jun. 12, 2000, and also claims priority to U.S. provisional Application No. 60/138,969, filed on Jun. 11, 1999, the contents of each of which are incorporated herein by reference in their entirety.

The research leading to this invention was supported in part by The National Institute of Health Grant No. 5R01HD3242902. Thus, the United States Government has certain rights in the invention.

BACKGROUND OF THE INVENTION

In virtually all animal phyla, critical steps in embryonic development are regulated by cell-to-cell, or inductive, signals mediated by secreted growth factors. In particular, members of the transforming growth factor β (TGFβ) superfamily regulate a myriad of cellular and developmental processes, such as mitosis, cell differentiation, embryonic pattern formation and organogenesis. In vertebrate embryos, a variety of TGFβ signals affect germ layer specification, body patterning, cell growth and differentiation (1-4). In embryos of the amphibian *Xenopus*, distinct TGFβ members induce different cell fates, e.g., activin, Vg1 and nodal induce mesoderm characteristic of the dorsal part of the embryo, such as notochord and muscle. Vg1 and activin also induce endoderm characteristics. In contrast, Bone Morphogenetic Proteins (BMPs) specify mesoderm, such as blood and mesenchyme, and regulate epidermal and neural cell differentiation in the ectoderm (see (5) for a review).

Cells respond to ligands in the TGFβ family by transducing signals directly from cell surface receptor complexes to nuclear DNA targets via the Smad family of proteins (see (4), (6), (7), and (52) for a review).

Smads are related to *Drosophila* Mad (mothers against decapentaplegic [dpp]) and proteins encoded by three related nematode genes Sma 2, Sma 3, and Sma 4. The terms Sma and Mad have been fused as Smad to unify the nomenclature. There are eight members in the Smad family. Phosphorylated Smads 1, 5 and 8 are functional mediators of BMP family signaling in partnership with Smad 4. Smads 2 and 3 are signal transducers for actions of TGFβ and activins. Smad 6 and Smad 7 function as antagonists to inhibit TGFβ/BMP superfamily signaling. Interestingly, Smad7 is localized in the nucleus and accumulates in the cytoplasm in response to TGFβ signalling (73). Furthermore, expression of both Smad6 and Smad7 is regulated by TGFbs, BMPs, growth factors and cytokines thereby providing for negative feedback regulation of the Smad signalling pathway (53-58). Phosphorylated Smad 1 forms a heteromeric complex with Smad 4 when entering the nucleus and activates transcription of early response genes. The BMP receptors may also signal via the mitogen activated protein kinase. It is likely that BMPs regulate cell cycle progression and thus govern differentiation of mesenchymal stem cells.

Signal transduction in two major pathways, BMP and activin/TGFβ, have been described in detail. Two distinct receptor subunits, the Type I and II transmembrane serine/threonine kinases, form activated complexes upon ligand binding. In these complexes the Type II subunit activates the Type I subunit, which directly phosphorylates and activates particular receptor-regulated R-Smad proteins: BMP receptors target Smad1 and closely-related Smads 5 and 8, while activin and TGFβ receptors target Smad1 and closely-related Smads 2 and 3. Upon activation these R-Smads form a heteromeric complex with Smad4, the "common partner" Smad. This complex translocates to the nucleus, binds to promoters of target genes in cooperation with DNA binding proteins, and activates transcription by recruiting coactivators. A third class of inhibitory Smads (I-Smads), Smad6 and Smad7, function as inhibitors that block Smad-Smad complex formation or Smad-receptor interactions. I-Smads bind to the cytoplasmic domain of receptors or directly to Smad1. Mutations in components at all levels in this pathway are associated with embryonic defects and various cancers, underscoring the importance of this growth factor family in developmental and disease processes. (See, (4), (7) for reviews.) In particular, defects of Smad2 and Smad4 are associated with colon and lung cancer and defects in human Smad4 are associated with pancreatic cancer.

Smads do not have intrinsic enzymatic activity. Thus, the nature of the cellular response to Smad signaling is exquisitely sensitive to the level of Smad protein in the cell. Indeed, alternative cell fate determinations in *Xenopus* embryos can be achieved by relatively small changes in the amount of Smad protein expressed in the cell (8-11). Therefore, regulating the level of Smad protein in the cell can be used as one means of modulating morphogenetic signaling by the TGFβ superfamily.

Protein modification by covalent attachment of ubiquitin is recognized as a general signal to target proteins for degradation via the proteasome (see (12), and (13) for a review). Targets of selective ubiquitination include transcription factors, cell cycle regulators, signal transduction proteins, and membrane proteins (references in (12)). Selective ubiquitination and degradation of specific target proteins can function as an important mechanism to control cell cycle progression, programmed cell death, differentiation and embryonic development. Dysfunction of the ubiquitination pathway is associated with disease and abnormal development. Ubiquitin ligases are part of a multimeric complex that catalyzes the covalent attachment of ubiquitin, a 12.5 kD polypeptide, to target proteins. Attachment of ubiquitin to its target serves as a molecular "flag" that marks the ubiquitinated protein for proteolytic degradation via an organelle known as the 26S proteosome. There are at least three enzymes involved in conjugating ubiquitin to target proteins, namely, E1, E2 and E3. The E1 enzyme activates a ubiquitin molecule and conjugates it to the E2 enzyme which then either directly attaches ubiquitin onto a target protein, or passes it to the E3 ubiquitin ligase. The E3 recognizes a particular substrate and directs it ubiquitination.

A few examples of developmental regulation by the ubiquitination system have been described in *Dictyostelium* (14-16) and *Drosophila* (17-21). Conjugation of ubiquitin to receptors is used in diverse systems to control endocytosis and signalling, as well as receptor steady state levels by both proteasome- and lysosome-mediated degradation (59-60). Direct ubiquitination of membrane receptors has been characterized in a number of systems, although in some cases ubiquitin-dependent regulation does not appear to involve direct conjugation of ubiquitin to the receptor (61-62). Although many cell surface receptors are regulated by ubiquitin-dependent pathways, few E3 ubiquitin ligases that bind to membrane proteins and target them for ubiquitination have been defined. Nedd4, a C2-WW-HECT domain E3 ubiquitin ligase, can regulate the turnover of the amiloride-sensitive sodium channel by binding directly to a PPXY motif present in the carboxy-terminus of the channel (63-66). Furthermore, the RING finger protein, c-cbl, has recently been shown to function as an E3 ubiquitin ligase that binds to the EGF receptor to mediate ubiquitination and downregulation of the receptor complex (67-68). In these examples, ubiquitination of the membrane proteins appears to involve direct interactions between the E3 ligase and the target protein. Whether adaptor proteins might also function to recruit E3 ligases to specific receptor complexes is unknown. The mechanism and targets of ubiquitination in the control of patterning have heretofore remained elusive.

References that are cited throughout the specification by number are listed at the end of the Example. All references cited herein are incorporated by reference.

SUMMARY OF THE INVENTION

The present invention advantageously provides a class of regulatory proteins that are involved in BMP and TGFβ-mediated activation. In particular, these proteins regulate Smad proteins and/or promote degradation of TGFβ receptor complexes in the presence of Smad proteins. By manipulating the activity of the proteins of the invention, the skilled artisan can up or down regulate cellular activation, e.g., via BMP or TGFβ.

Thus, in a first aspect, the invention provides an isolated Smurf protein, and particularly a human Smurf protein. In one embodiment, it is a Smurf1 protein. In an alternative embodiment, it is a Smurf2 protein. In specific embodiments, exemplified infra, a human Smurf1 has the amino acid sequence depicted in FIG. 10 (SEQ ID NO:2), and a human Smurf2 has the amino acid sequence depicted in FIG. 12 (SEQ ID NO:4). Smurf proteins of the invention may contain at least about 5 and preferably at least about 10 contiguous amino acids from the sequences depicted in SEQ ID NO:2 and 4.

The invention further provides an antibody that specifically binds to Smurf protein.

The invention further provides a nucleic acid encoding the Smurf proteins of the invention. In specific embodiments, the nucleic acid has a nucleotide sequence as depicted in SEQ ID NO:1 or SEQ ID NO:3.

The invention further provides an oligonucleotide or nucleic acid that specifically hybridizes under highly stringent conditions to a nucleic acid having a sequence encoding Smurf, or the complementary sequence thereof. Such hybridizable nucleic acids include probes (i.e., they may be labeled), primers (e.g., for PCR amplification), anti-sense nucleic acids, ribozymes, and triple-helix forming nucleic acids.

The invention further provides a vector comprising the nucleic acid encoding Smurf, e.g., under control of an expression control sequence. Also provided are host cells, harboring such a vector, and methods for producing Smurf by culturing such host cells under conditions that permit expression of Smurf protein from the vector.

Also contemplated is a transgenic non-human animal that expresses a human Smurf protein and non-human animals in which endogenous Smurf protein is deleted.

The invention further provides a method for inhibiting a bone morphogenic protein or transforming growth factor-beta activation pathway in a cell. This method comprises permitting the cell to grow under conditions that permit expression of Smurf from a vector of introduced into the cell. Alternatively, the invention provides a method for promoting a bone morphogenic protein or transforming growth factor-beta activation pathway in a cell, which method comprises suppressing expression of endogenous Smurf in the cell.

In addition, the present discoveries permit screening for a modulator of Smurf activity. Screens of the invention comprise detecting modulation of Smurf activity in the host cell in the presence of a test compound relative to Smurf activity of the host cell in the absence of the test compound. As shown in the examples, one such activity is ubiquitination of Smad proteins. Another activity is the enhancement of TGFβ receptor degradation.

DESCRIPTION OF THE DRAWINGS

FIGS. 1A-D. Smurf1 encodes an E3 ubiquitin ligase. Protein sequence of *Xenopus* and human Smurf1 compared to yeast (*S. pombe*) pub1, given as SMURF1, hSMURF1 and PUB1, respectively in the figure. Identical amino acids are shaded dark gray and conservative substitutions are shaded light gray. Based on primary structure, Smurf1 and pub1 are members of the Hect family of E3 ubiquitin ligases and display several conserved features of the family: A lipid/Ca2+ binding domain is located at the N-terminus (residues 22-37), two WW protein interaction domains at 236-271 and 282-311 (indicated by thick lines), and a catalytic Hect domain beginning at residue 347 and extending to the C-terminus. Alignment was by CLUSTALW analysis (MacVector).

FIGS. 3A and 3B. Developmental expression of *Xenopus* Smurf1.

Figure 2A:
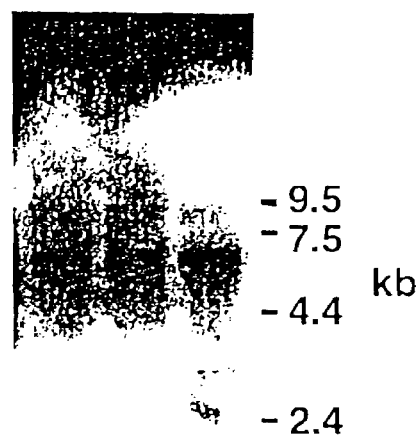
FIGS. 2A and 2B. Northern blots of mSmurf1 expression in embryonic and adult mouse tissues. Equal amounts of PolyA+ mRNA from indicated stages and tissues were analyzed. (2A) Embryonic tissue—In this blot, embryonic days post coitum are indicated. (2B) Adult tissues shown are T, testes; K, kidney; M, skeletal muscle; L, lung; Sp, spleen; Br, brain; H, heart.

(A) RT-PCR on staged embryonic cDNA revealed that *Xenopus* Smurf1 is a maternal mRNA, present at highest levels in egg, blastula and early gastrula stages. Zygotic Smurf1 mRNA levels decline at gastrulation but maintain steady expression into swimming tadpole stages. Numbers above each lane correspond to Nieuwkoop and Faber stages: 7 and 9, blastula; 11 and 13, gastrula; 15 and 20, neurula; 25 and 35, tadpole. Ornithine decarboxylase (ODC) mRNA, ubiquitously expressed in cells, was assayed to normalize for RNA recovery. RT-PCR on mock cDNA (no reverse transcriptase).

(B) Whole-mount in situ hybridization of Smurf1 in developing *Xenopus* embryos. In egg and blastula stages Smurf1 transcripts are localized to the animal pole half (bracket in egg). Expression is diffuse throughout the ectoderm and involuting marginal zone of the gastrula; views from, animal pole (an) and vegetal pole (Veg). There is some enrichment of transcripts in the neural folds at neurula stage 17. At tadpole stages 25 and 35 Smurf1 expression includes the brain (b), eye (e), otic vesicle (o), somites (s), pharyngeal pouches (p) and developing kidney (k).

FIGS. 4A, 4B, 4C, and 4D. Smurf1 leads to a selective decrease in steady-state level of Smad1 and Smad5 in mammalian cell lines. Cells were transiently transfected with the indicated expression vectors (DNA quantities in μg) and two days later an aliquot representing approximately 0.4% of total cell lysates were subjected to SDS-PAGE and immunoblotting. To determine the steady-state level of the Smads, the blots were probed with the appropriate Smad antibody as shown. Flag-hSmurf1 expression level was confirmed by probing blots of total cell lysates with the anti-Flag monoclonal antibody.

(A) COS-1 or 293T-cells were transfected with a constant amount of pCMV5-Smad1 and increasing concentrations of pCMV5-Flag-hSmurf1 as indicated. To determine Smad1 steady-state level and the expression of hSmurf1, Western blots of total cell lysates from both cell lines were probed with α-Smad1 and α-Flag antibodies (α-Smad1 and α-Flag blot).

(B) 293T cells were transiently transfected with pCMV5-Smad1, wild type or activated (Q203D) pCMV5-ALK6-HA, and increasing amounts of pCMV5-Flag-hSmurf1 as indicated. Smad1 steady-state levels were examined by immunoblotting total cell lysates in Western blots with α-Smad1 antibody (α-Smad1). hSmurf1 and wild type or activated ALK6 expression levels were determined by immunoblotting the total cell lysates with α-Flag (α-Flag) or α-HA (α-HA) antibody, respectively.

(C) 293T cells were transfected with a constant amount of pCMV5-Smad1 or pCMV5-Smad2 along with the indicated concentrations of pCMV5-Flag-hSmurf1. Smad1 (α-Smad1 blot), Smad2 (α-Smad2 blot) and Flag-hSmurf1 (α-Flag blot) steady-state protein levels were determined in cell lysates, as above.

(D) 293T cells were transfected with Smad1, Smad3, Smad4 or Smad5 in pCMV5 in the absence or presence of pCMV5-Flag-hSmurf1. The steady-state level of the Smads in total cell lysates was determined by incubating the Western blots with α-Smad1 antibody for Smad1 and Smad5, α-Smad3 antibody for Smad3, and α-Smad4 antibody for Smad4 detection (α-Smads blot). Equivalent hSmurf1 expression was confirmed as described above (α-Flag blot).

FIGS. 5A, 5B, 5C, and 5D. hSmurf1 regulates Smad1 turnover and ubiquitination: hSmurf1 enhances Smad1 turnover.

Figure 5A:
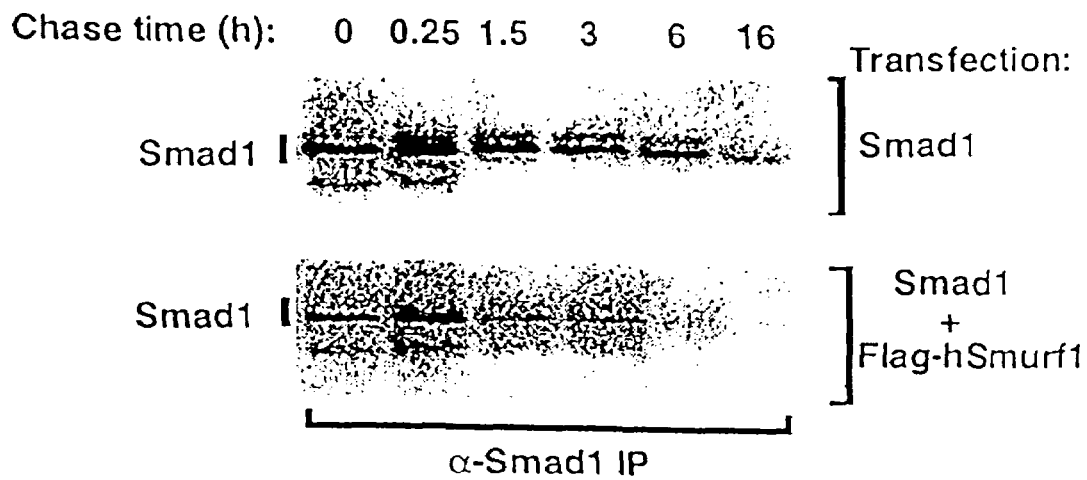
Figure 5B:
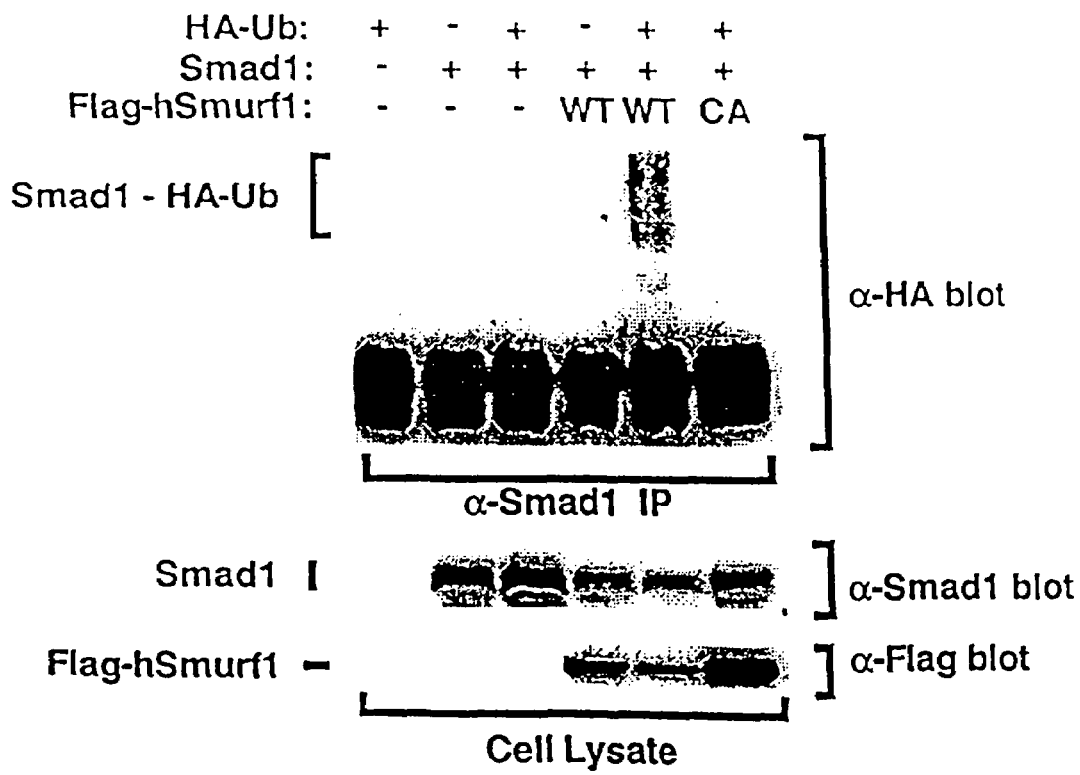
Figure 5C:
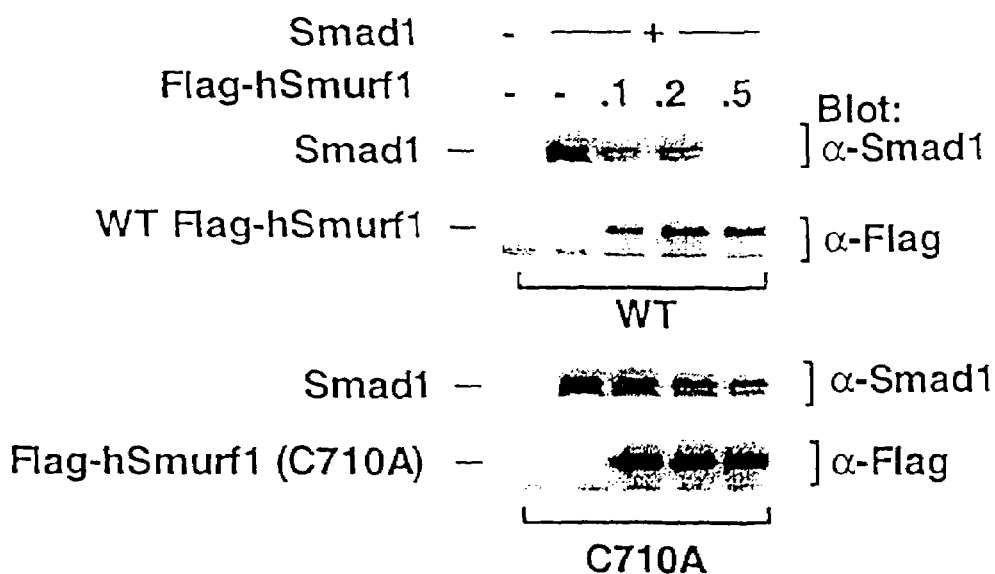
Figure 5D:
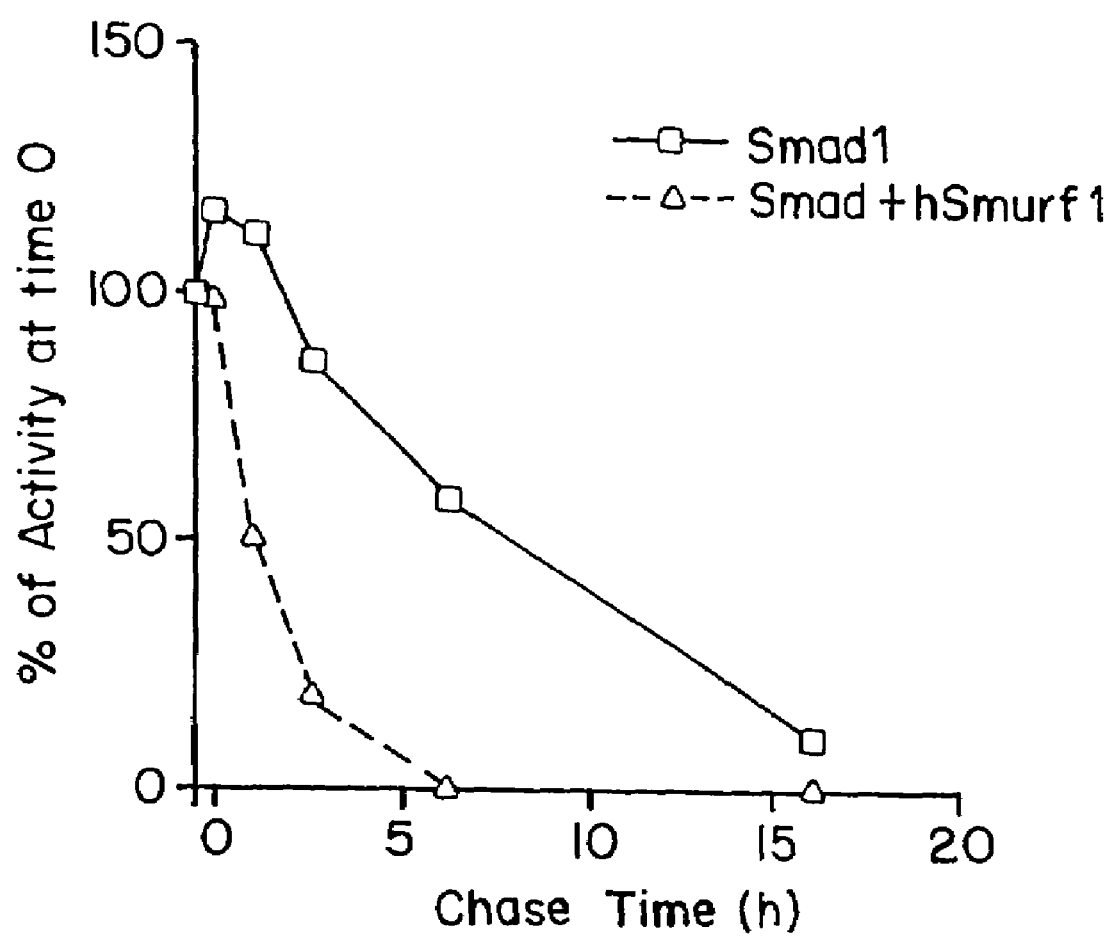

(A) and (D) COS-1 cells were transiently transfected with pCMV5-Smad1 alone or with FLAG-tagged hSmurf1 (F/hSmurf1) using LIPOFECTAMINE. Two days later, transfectants were subjected to pulse-chase analysis using [$^{35}$S] methionine. At the indicated time during the chase, cells were lysed and subjected to an α-Smad1 immunoprecipitation. The immunoprecipitates were resolved by SDS-PAGE and visualized by autoradiography (FIG. 5A). Radiolabelled Smad1 was also quantitated by phosphoimaging, and the results are plotted as the amount of [$^{35}$S] methionine-labelled Smad1 present at each time point relative to the level at time 0 (FIG. 5D).

(B) Ubiquitination of Smad1 in 293T cells. Cells were transiently transfected with indicated combinations of HA-tagged ubiquitin (HA-Ub), pCMV5-Smad1 and either wild type (WT) or the ubiquitin ligase mutant (CA) of Flag-tagged hSmurf1. Two days post-transfection, lysates were subjected to an α-Smad1 immunoprecipitation (α-Smad1 IP) followed by SDS-PAGE and immunoblotting with an α-HA monoclonal antibody (α-HA blot). Protein bands displaying immunoreactivity to α-HA are marked by the square bracket. Expression of Smad1 or Flag-hSmurf1 was confirmed by subjecting total cell lysates to immunoblotting with an α-Smad1 polyclonal antibody (α-Smad1 blot) or an α-Flag monoclonal antibody (α-Flag blot), respectively.

(C) Loss in Smad1 steady-state level by hSmurf1 requires an intact ubiquitin ligase activity of the Hect domain. 293T cells were transfected with Smad1 and increasing amounts of the wild type (WT) or the ubiquitin ligase mutant (C710A). Total cell lysates were analyzed for Smad1, hSmurf1 or hSmurf1 (C710A) protein by immunoblotting total cell lysates with the appropriate antibody, as described in FIG. 3.

Figure 6A:
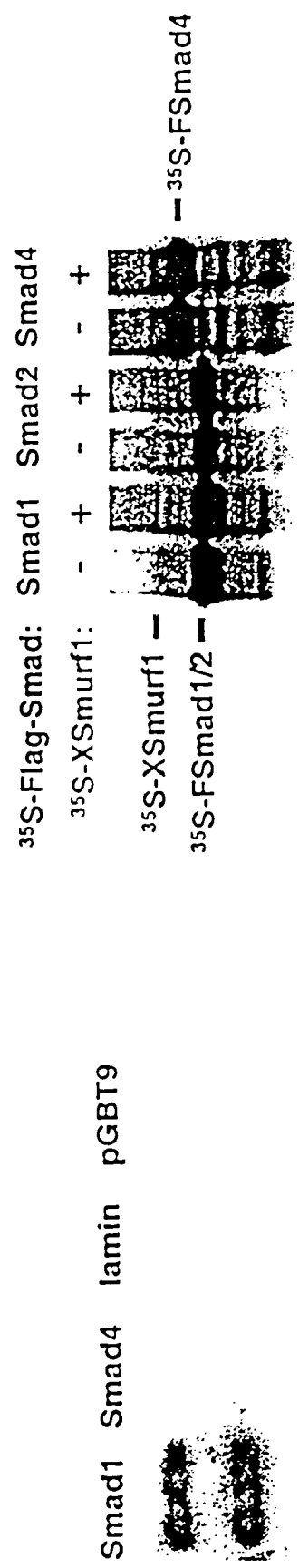
Figure 6B:
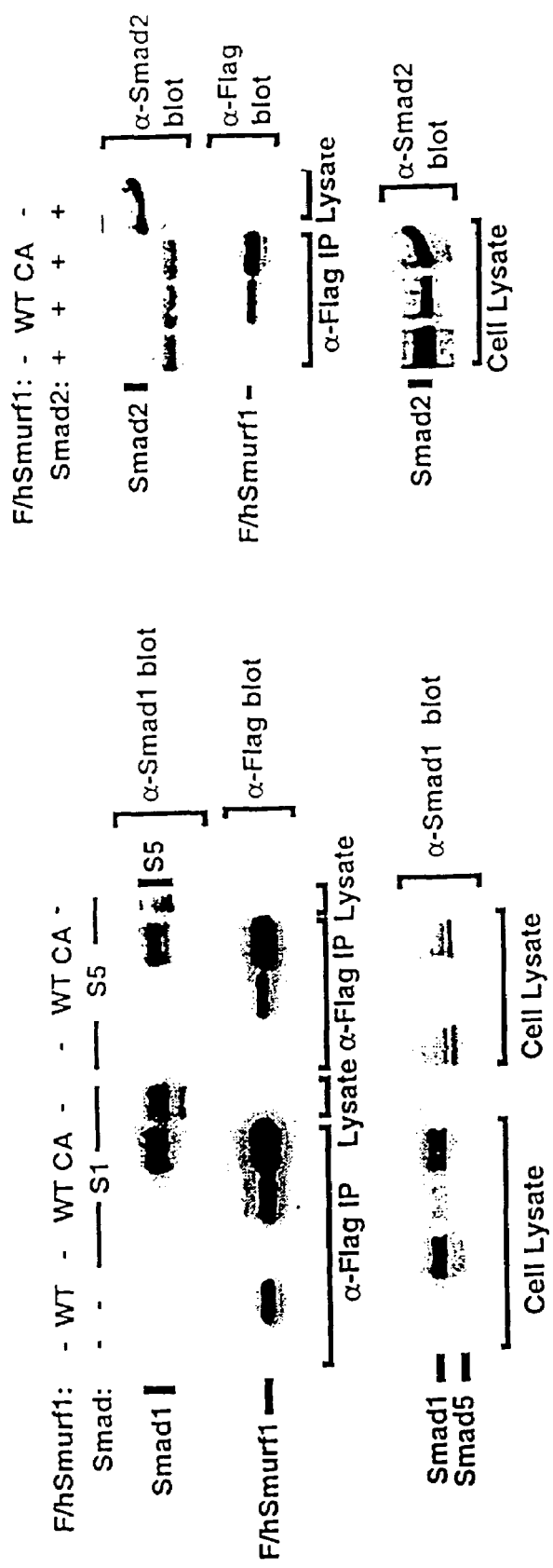
Figure 6C:
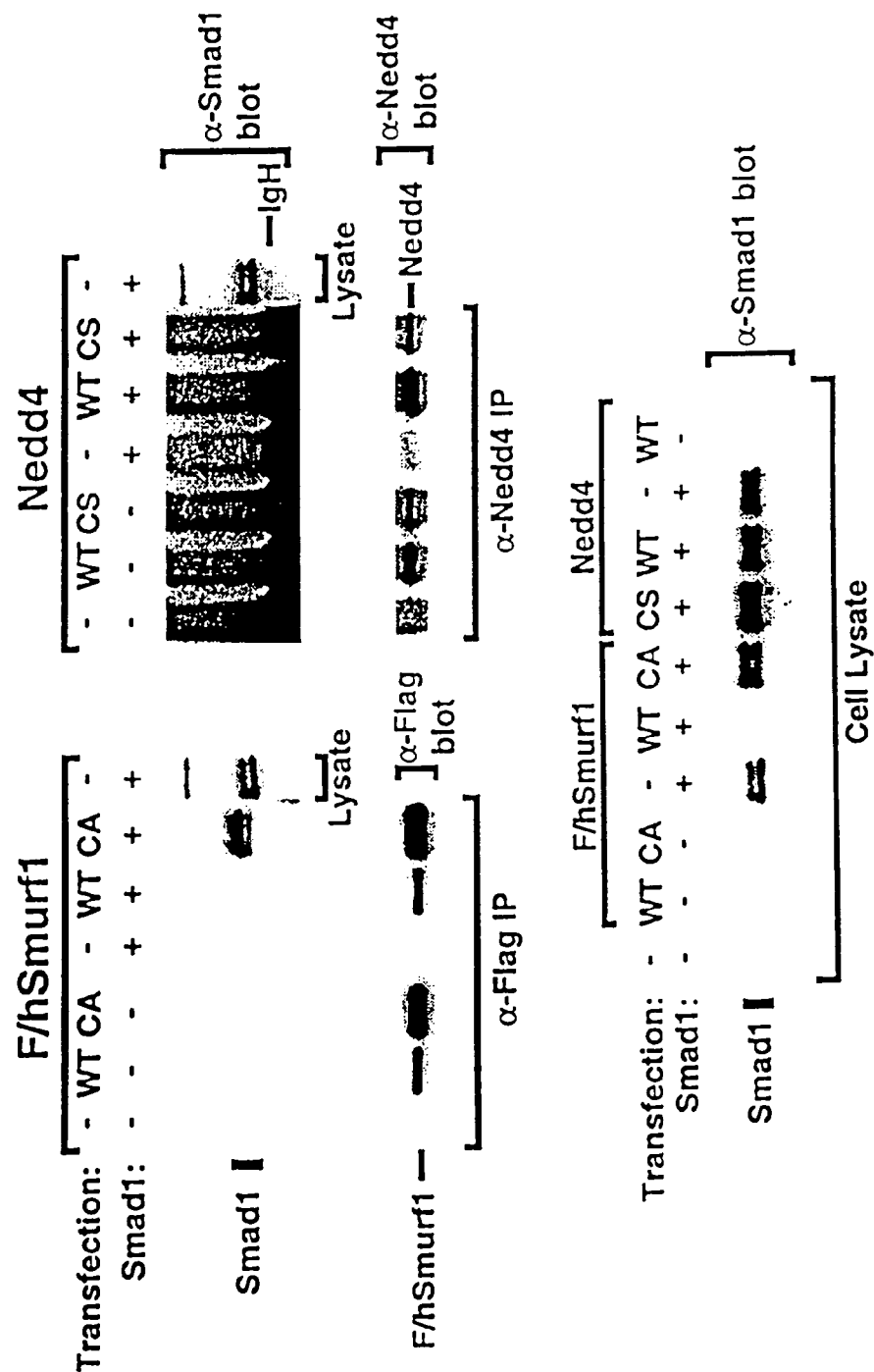

FIGS. 6A, 6B, and 6C. Interaction of Smurf1 and Smads.

(A) Smurf1 interacts with Smad1. Yeast two-hybrid assays were done on yeast co-transformed with combinations of Xenopus Smurf1 (Xsmurf) together with Smad1, Smad2, lamin or vector alone. Only the combination of Smad1 and Smurf1 exhibited significant β-galactosidase activity (left panel, photograph of stained yeast colonies assayed in duplicate). Co-immunoprecipitation on in vitro translated proteins was done by incubating 35S-labelled Smurf1 together with in vitro translated, 35S-Met trace-labelled Flag-tagged Smad1 (35S-F/Smad1), Smad2 (35S-F/Smad2) or Smad4 (35S-F/Smad4) immobilized on anti-Flag affinity gel matrices. After washing, bound proteins were eluted and analyzed by SDS-PAGE (right panel).

(B) hSmurf1 interacts selectively with both Smad1 and Smad5. 293T cells were transiently transfected with the pCMV5 expression vectors containing Smad1 (S1), Smad5 (S5) or Smad2 either alone, with wild type (WT) or the ubiquitin ligase mutant (CA) Flag-tagged hSmurf1 (F/hSmurf1). To examine Smad1 or Smad5 interaction with hSmurf1, blots of α-Flag immunoprecipitates were probed with α-Smad1 polyclonal antibody (α-Smad1 blot). To examine Smad2 interaction with hSmurf1, blots of α-Flag immunoprecipitates were probed with α-Smad2 polyclonal antibody (α-Smad2 blot). The level of hSmurf1 in the immunoprecipitates and Smad1, Smad5 and Smad2 in the total cell lysates, are shown in the lower two panels.

(C) Specificity of hSmurf1 actions on Smad1. Nedd4, a ubiquitin ligase related to hSmurf1, does not interact with and does not reduce the steady-state level of Smad1. 293T cells were transiently co-transfected with Smad1 and either Flag-tagged hSmurf1 (WT or CA) or Nedd4, (WT) or ligase mutant (CS) as indicated. Smad1 coimmunprecipitation with hSmurf1 (left panels) was determined as described above. To determine Smad1 interaction with Nedd4, cell lysates were subjected to immunoprecipitation using a-Hect-Nedd4 polyclonal antibody (α-Nedd4 IP) followed by immunoblotting with α-Smad1 polyclonal antibody (α-Smad1 blot), right panels. To determine the level of expression of Nedd4 in the samples, the respective blots were reprobed with a-WW2 Nedd4 polyclonal antibody (α-Nedd4 blot). Smad1 levels in total cell lysates of these assays are shown by western blot in the bottom panel.

Figure 7B:
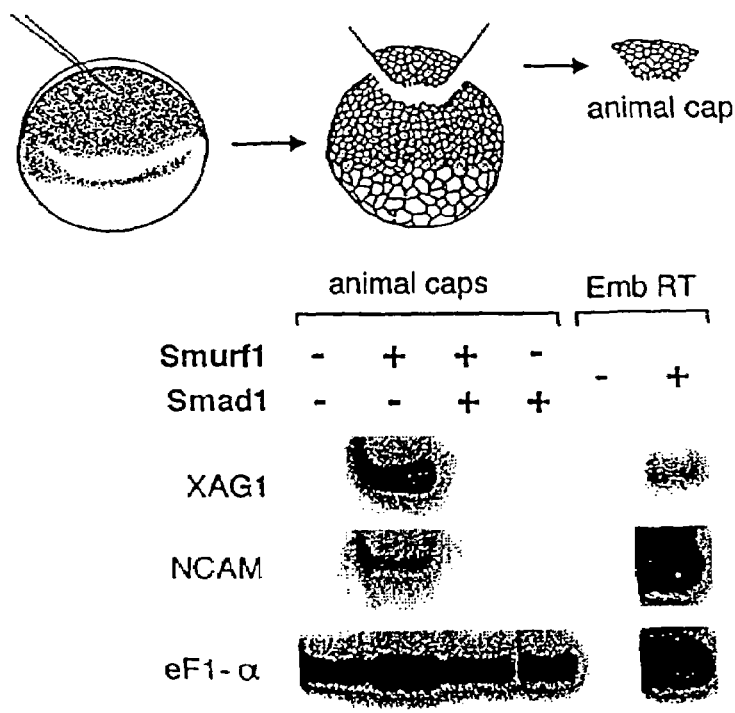
Figure 7A:
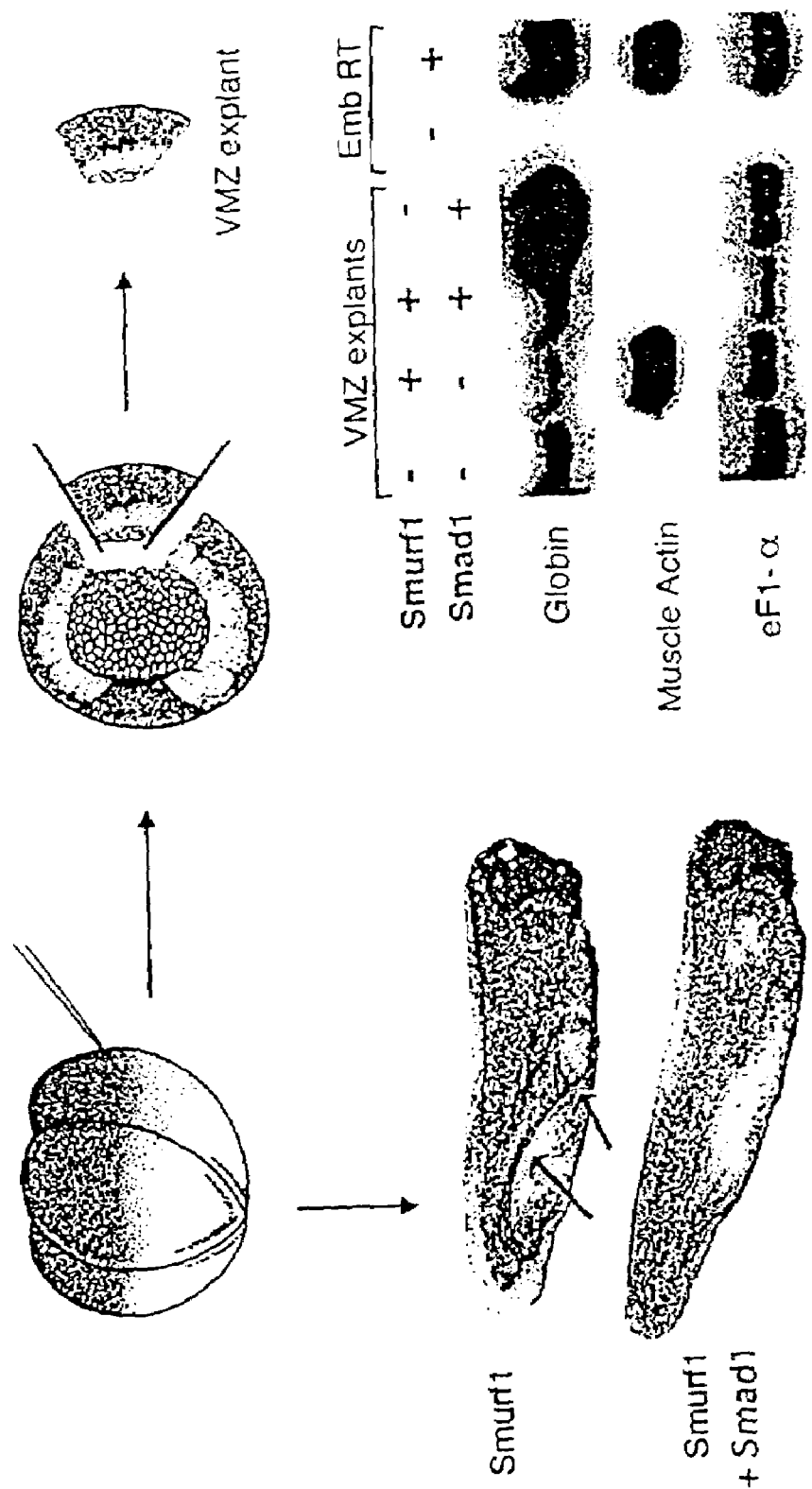

FIGS. 7A and 7B. Smurf1 dorsalizes prospective ventral mesoderm and neuralizes ectoderm.

(A) Four cell Xenopus blastulae were injected with Xenopus Smurf mRNA in the marginal zone of two ventral blastomeres (50 pg Smurf1 mRNA per cell). Tadpoles that developed from injected embryos formed ectopic, dorsal axial structures (lower left panel, arrows). Co-injection of 100 pg Smad1 together with 50 pg of Smurf1 mRNA rescued the ectopic axial structures in all cases (lower tadpole). At early gastrulation ventral marginal zone (VMZ) pieces were explanted from another set of wild-type embryos, or embryos injected in the VMZ at the four cell stage with Smurf1 mRNA alone, or Smurf1 co-injected with Smad1. The VMZ explants were excised at early gastrulation, as depicted, then cultured until control embryos reached mid-tadpole, stage 28, when total VMZ RNA was prepared then assayed by RT-PCR for the expression of erythrocyte-specific α-globin, muscle-specific actin, and general cellular mRNA, eF1-a, as a control for RNA recovery (lower right panel). Control PCR reactions were done on total embryonic RNA with or without reverse-transcription.

(B) Fertilized egg animal poles were injected with Smurf1 and/or Smad1 mRNA, or were not injected. Animal caps were explanted at blastula stage 8, cultured to mid-gastrula stage 11, then total RNA was prepared and assayed by RT-PCR to detect expression of the cement gland marker, XAG, and a general neural marker, NCAM. Controls were as above.

Figure 8A:
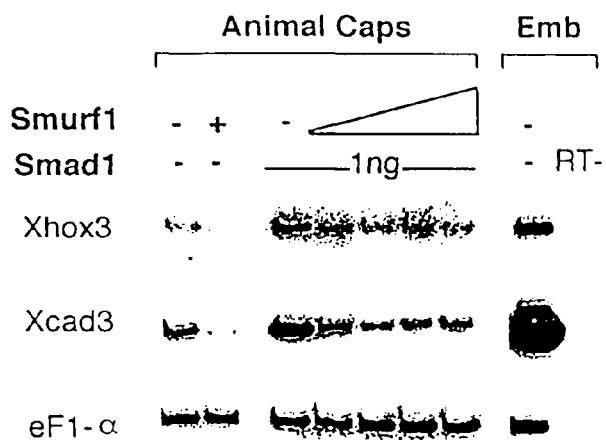
Figure 8B:
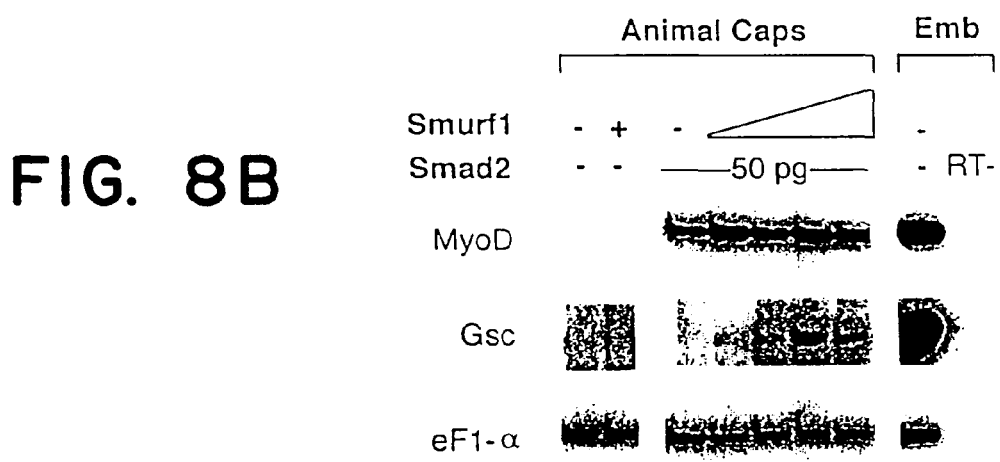
Figure 8C:
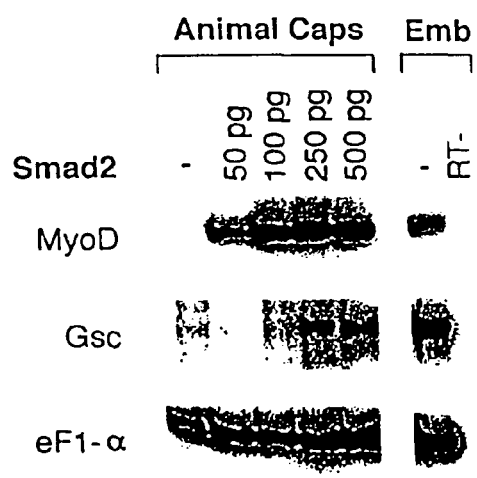

FIGS. 8A, 8B, and 8C. Smurf1 alters embryonic cell competence to respond to Smad1 and Smad2.

(A) Smurf1 blocks ventral mesoderm induction by Smad1. A constant amount (1 ng) of Smad1 mRNA was injected alone, or together with an increasing amount of Smurf1, into fertilized egg animal poles and ventral mesoderm induction in animal cap explants was assayed by RT-PCR with primers for the Xhox3 and Xcad3 homeodomain genes. In lanes from left to right, respectively, animal caps were not injected or injected with Smurf1 mRNA at doses of 100, 0, 25, 50, 100, and 200 pg.

(B) Smurf1 enhances dorsal mesoderm induction by Smad2. A constant amount (50 pg) of Smad2 mRNA was injected alone, or together with an increasing amount of Smurf1, and dorsal mesoderm induction was monitored by expression of myoD, which marks muscle, and goosecoid, a homeodomain gene expressed in the most dorsal type of mesoderm, the Spemann Organizer. Note that goosecoid expression was triggered from undetectable levels, as the dose of Smurf1 was increased. Animal caps were injected as in panel a.

(C) Dose-response of animal caps to Smad2. Animal caps were injected with synthetic mRNAs for Smad2. At 50 pg Smad2 MyoD was induced and reached maximal levels at 100 pg or more injected Smad2. Goosecoid was induced at a minimum Smad2 dose of 250 pg. The level of goosecoid induced by 250 pg Smad2 alone was equivalent to the level of goosecoid induced by a combination of 50 pg of Smad2 and 100 pg of Smurf1 (panel b).

In all panels the far right two lanes correspond to PCR on wildtype embryonic RNA, with (RT+) and without (RT−) reverse transcription, respectively. eF1-a controls in all panels were as in FIG. 7.

FIGS. 9A-F. cDNA sequence of human Smurf1 [SEQ ID NO:1].

FIGS. 10A-C. Protein sequence of human Smurf1 [SEQ ID NO:2].

FIGS. 11A-H. cDNA sequence of human Smurf2 [SEQ ID NO:3].

FIG. 12. Protein sequence of human Smurf2 [SEQ ID NO: 4].

Smurf2 is member of the HECT E3 ubiquitin-ligase family. The C2 (overline), WW (shaded) and HECT (double overline) domains and the Cys716Ala mutation (boxed) are shown.

Figure 13:
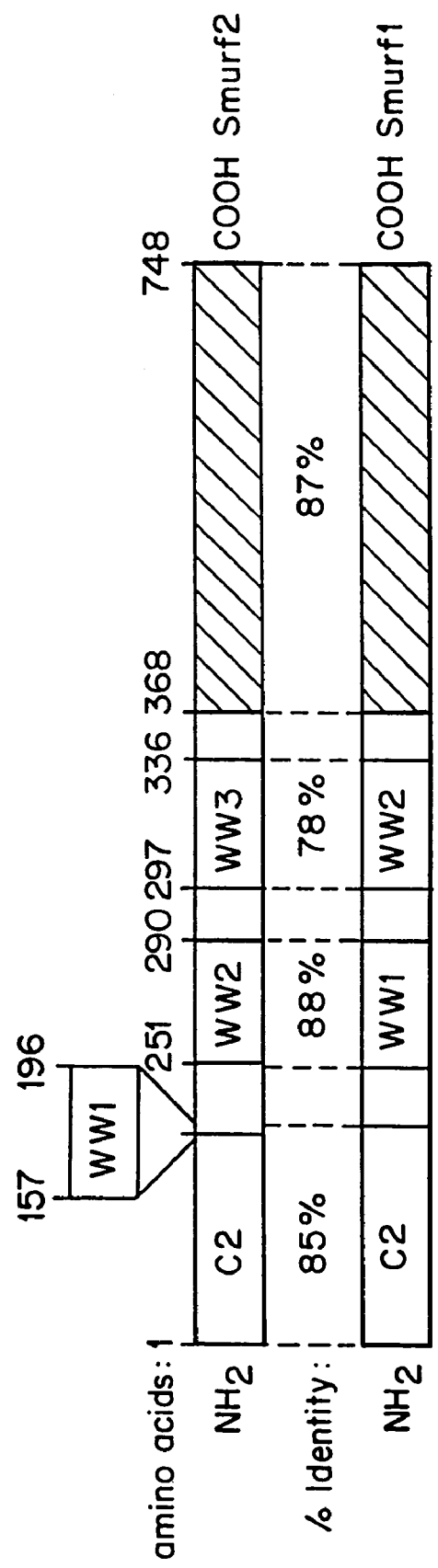

FIG. 13. Comparison of Smurf1 and Smurf2 proteins.

Schematic representation of Smurf1 and Smurf2. The degree of amino acid identity (%) between the C2, WW and HECT domains is shown.

Figure 14A:
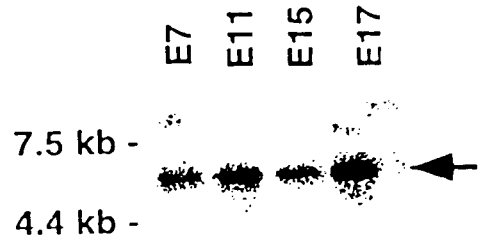
Figure 14B:

FIGS. 14A and 14B. Smurf2 is expressed in mouse tissues.

(A) Smurf2 is expressed throughout mouse embryogenesis. A 1 kb XhoI/NotI fragment encompassing the 3'UTR of mouse Smurf2 was used to probe a mouse embryonic Northern Blot (Clontech).

(B) Expression of Smurf2 in adult mouse tissues. A multiple tissue northern blot (Clontech) was probed with a fragment of mouse Smurf2 as in A.

FIGS. 15A, 15B, 15C, 15D, 15E and 15F. Smurf2 interacts with Smad7.

Figure 15A:
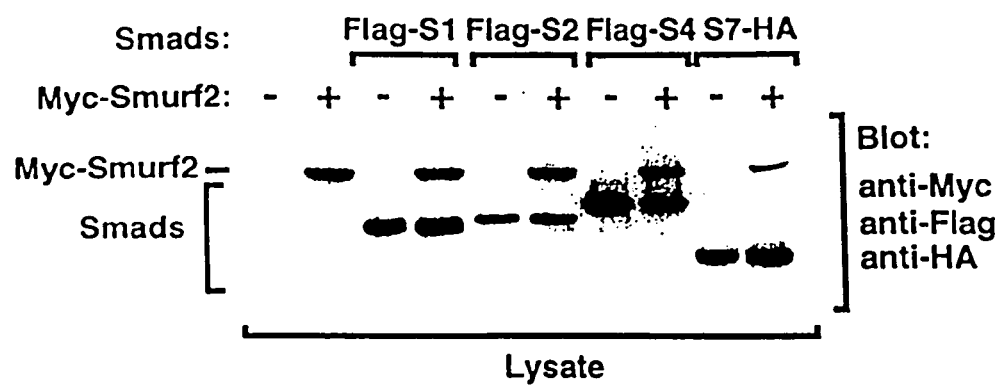
Figure 15B:

(A and B) Expression of Smurf2 does not decrease steady-state levels of the Smads. 293T cells were transfected with Flag-tagged Smad1, Smad2, Smad4 or HA-tagged Smad7 either alone or together with the Myc-tagged Smurf2. Aliquots of total cell lysates were immunoblotted to detect expression of Smurf2 and the Smads (FIG. 15A) or were subjected to immunoprecipitation with anti-Myc antibody followed by anti-Flag or anti-HA immunoblotting to detect any coprecipitating Smads (FIG. 15B). The migration of the anti-Myc heavy chain (IgH) is marked.

(C) Expression of Smurf2 does not alter Smad7 turnover. COS-1 cells, transfected with either Smad7-HA alone or together with Flag-Smurf2, were pulse-labelled with [$^{35}$S]-methionine and then chased for the indicated times in media containing unlabelled methionine. [$^{35}$S]-labelled Smad7-HA in anti-HA immunoprecipitates was quantified by phosphorimaging and the levels in control cells (squares) and Smurf2 expressing cells (circles) was plotted relative to the amount present at time 0. Data represents the average of two experiments +/−SD.

(D) In vitro interaction of bacterially-expressed Smurf2 and Smad7. Bacterially-produced His-Smad7-HA protein was incubated with $Ni^{2+}$-NTA, GST and GST-Smurf2. Bound material was visualized by SDS-PAGE and immunoblotting with anti-HA antibody. Levels of GST proteins were determined by Coomassie staining (bottom panel).

(E) The PY motif in Smad7 is an important determinant for mediating interaction with Smurf2. 293T cells were transfected with Flag-Smurf2 either alone or together with wild type (WT) or mutant Y211A (YA) or ΔPYversions of Smad7-HA. Cell lysates were subjected to anti-Flag immunoprecipitation and coprecipitating Smurf2 proteins were detected by immunoblotting with anti-Smad7 antibody. Smad7 expression was confirmed by immunoblotting aliquots of total cell lysates (bottom panel).

(F) The WW domains of Smurf2 are necessary for binding to Smad7. 293T cells were transfected with Smad7-HA and either wild type (WT) or mutant (ΔWW1, ΔWW2 or ΔWW3) versions of Flag-Smurf2. Cell lysates were subjected to anti-Flag immunoprecipitation, and coprecipitating Smad7 was detected by immunoblotting with anti-HA antibody. Smad7 expression was confirmed by immunoblotting aliquots of total cell lysates (bottom panel).

Figure 16B:
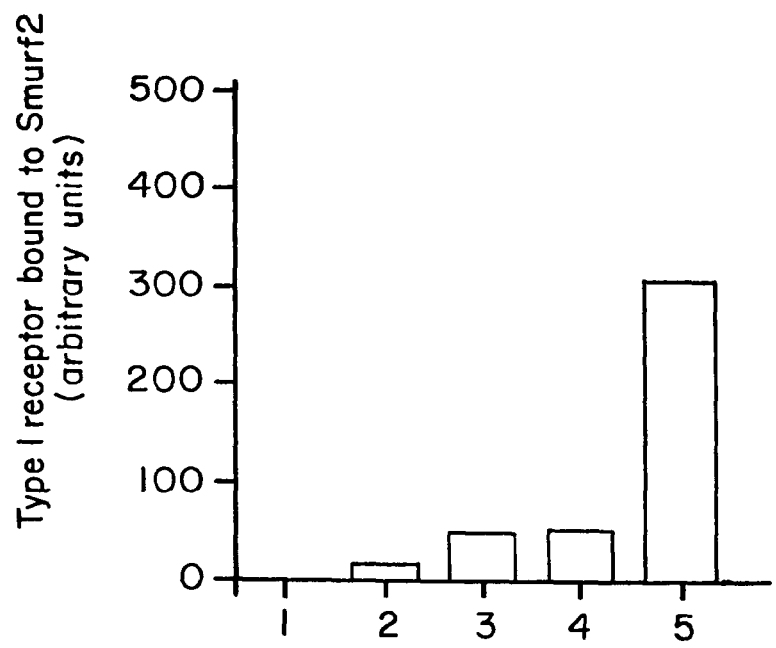
Figure 16C:
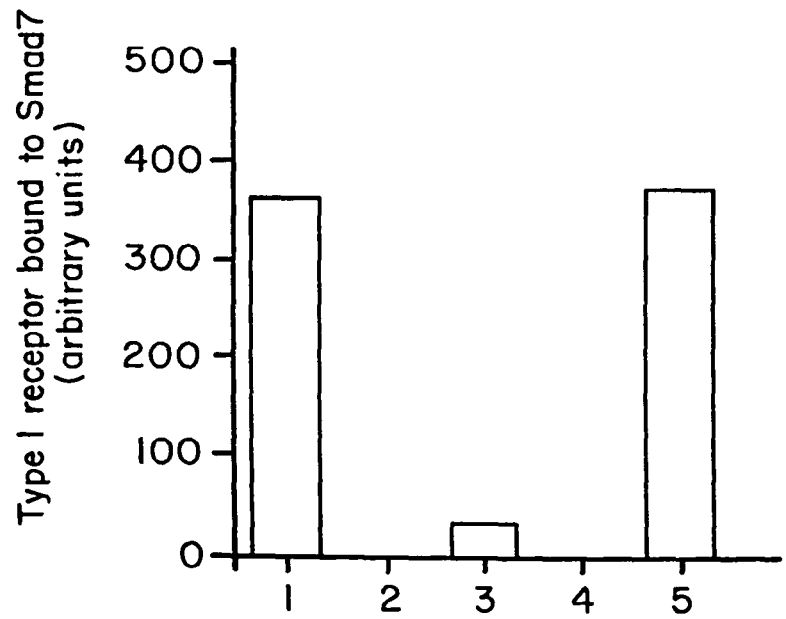

FIG. 16. Smad7 recruits Smurf2 to the TGFβ receptor complex.

COS-1 cells were transfected with various combinations of TβRII, TβRI-HA, Smad7-HA and wild type (WT) or mutant (C716A) Flag-Smurf2 as indicated. Cells were affinity-labelled with [$^{125}$I]TGFβ and lysates immunoprecipitated with anti-Flag or anti-Smad7 antibodies. Coprecipitating receptor complexes were visualized by SDS-PAGE and autoradiography. The amount of coprecipitating TβRI was quantified by phosphorimaging (right panels). Receptor expression was confirmed by visualizing aliquots of total cell lysates by autoradiography. Smurf2 and Smad7 levels were confirmed by immunoblotting aliquots of total cell lysates with anti-Flag and anti-HA antibodies, respectively.

FIGS. 17A, 17B, 17C, 17D and 17E. Smurf2 induces degradation of TGFβ receptors and Smad7.

(A) Smurf2 expression in the absence of Smad7 does not decrease receptor steady-state levels. 293T cells were transfected with various combinations of TβRII-HA, TβRI-HA and varying amounts of Flag-Smurf2 (plasmid DNA in micrograms) is indicated. Expression levels of proteins were determined by immunoblotting aliquots of total cell lysates using the appropriate antibodies as shown.

(B) Smurf2 in the presence of Smad7 causes a decrease in steady-state receptor levels. 293T cells were transfected with Smad7-HA, either TβRII-HA and TβRI-HA (left panels) or with a constitutively active type I receptor, TβRI-HA (T204D) (right panels) together with increasing amounts of wild type (WT) or mutant Flag-Smurf2 (C716A). Steady-state levels of the receptors, Smad7 and Smurf2 were determined by anti-HA or anti-Flag immunoblotting as indicated.

(C) Smurf2 increases the turnover rate of the receptor complex. COS-1 cells transfected with TGFβ receptors (TβRII-HA and TβRI-HA) alone or together with Smad7-HA, FLAG-Smurf2 or both were pulse-labelled with [$^{35}$S]-methionine and then chased for the indicated times in media containing unlabelled methionine. Cell lysates were subjected to anti-HA immunoprecipitation and the amount of labelled receptors and Smad7 was quantified by phosphorimaging and is plotted relative to the amount present at time 0 (FIGS. C1-4).

(D) Proteasome and lysosome inhibitors block Smurf2-induced degradation of the receptor complex. COS-1 cells transfected with TGFβ receptors (TβRII-HA and TβRI-HA), Smad7-HA and Flag-Smurf2 were pulse-labelled with [$^{35}$S]-methionine and then chased either in absence of inhibitors or in the presence of 30 mM lactacystin, or 0.4 mM chloroquine for the indicated times. Cell lysates were subjected to anti-HA immunoprecipitation and receptor and Smad7 levels were visualized by SDS-PAGE and autoradiography.

(E) Smurf2 induces the ubiquitination of Smad7 in the presence of the receptors. 293T cells were transfected with HA-tagged ubiquitin together with various combinations of Smad7, TβRII, TβRI-Flag, and wild type (WT) or mutant (C716A) Myc-Smurf2 as indicated. Cell lysates were subjected to a double immunoprecipitation with anti-Smad7 antibodies followed by immunoblotting with anti-HA antibodies. Protein expression in aliquots of total cell lysates was confirmed by immunoblotting.

FIGS. 18A, 18B, 18C and 18D. Association of Smurf2 with Smad7 enhances the Smad7 inhibitory activity.

(A) Smad7(Y211A) binds to TGFβ receptors but has a reduced ability to recruit Smurf2 to the receptor complex. COS-1 cells were transfected with TGFβ receptors (TβRII and TβRI-HA) and either wild type (WT) or mutant (Y211A) Smad7/HA in the absence or presence of Flag-Smurf2(C716A). Cells were affinity-labelled with [$^{125}$I] TGFβ and lysates immunoprecipitated with anti-Smad7 or anti-Flag antibodies. Coprecipitating receptor complexes were visualized by SDS-PAGE and autoradiography. Total receptor expression was determined by autoradiography and Smad7 and Smurf2 protein levels were confirmed by anti-HA or anti-Flag immunoblotting of aliquots of total cell lysates.

(B and C) Smad7(Y211A) is not as effective as wild type Smad7 in inhibiting TGFb-dependent activation of transcription. HepG2 cells were transfected with the 3TP-Lux reporter alone or together with varying concentrations of wild type (WT) or mutant (Y211A) Smad7-HA. In (B), 0.3 ng/ml of each Smad7 plasmid was used. Cells were incubated in the presence or absence of TGFβ1, and luciferase activity was normalized to b-galactosidase activity and is plotted as the mean +/−SD of triplicates from representative experiments.

(D) A model for Smad7 and Smurf2-mediated degradation of the TGFβ receptor complex. Smad7 binds directly to Smurf2 and associates with the TGFβ receptor complex. Thus, Smad7 functions as an adaptor protein that mediates degradation of the TGFβ receptor complex.

DETAILED DESCRIPTION OF THE INVENTION

The present invention is directed to a family of genes encoding E3 ubiquitin ligases, called Smurf proteins, and includes full length, or naturally occurring forms, and any functionally active or antigenic fragments thereof, from any animal, particularly mammal or amphibian, and more particularly from a human source. In specific embodiments, the E3 ubiquitin ligases called Smurf1 and Smurf2 are characterized.

This invention is based, in part, on the surprising discovery that two novel members of the Hect family of ubiquitin ligases interact with Smads. These ligases have been named Smurf1 and Smurf2. One of these, Smurf1, specifically targets BMP pathway-specific Smads, thereby acting as an antagonist or negative regulator of BMP signaling. Smurf1 directly interacts with Smads1 and 5 and regulates their ubiquitination, turnover, and activity. In amphibian embryos, Smurf1 inhibits endogenous BMP signals, resulting in altered pattern formation and cell fate in the mesoderm and ectoderm. Thus, the invention provides a unique regulatory protein link between the ubiquitination pathway and the control of cell fate, e.g., during embryonic development. The invention further provides a nucleic acid encoding Smurf1 [SEQ ID NO: 1], in addition to the Smurf1 protein, [SEQ ID NO: 2], and mutant variants thereof.

The other novel member of the Hect family of ubiquitin ligases is Smurf2. Smurf2, a C2-WW-HECT domain E3 ubiquitin ligase is related to Smurf1. Smurf2 does not interact with Smad1, 2 or 4, nor does Smurf2 alter steady state levels of Smad 1, 2 or 4. Smurf2, however, does interact with Smad 7, binding directly to a PPXY motif in Smad7. Smurf2 is involved with TGFβ receptor degradation acting in partnership with Smad7 as an antagonist or negative regulator of TGFβ signaling. Activation of TGFβ signalling results in Smad7-dependent recruitment of Smurf2 to the TGFβ receptor complex. In the absence of activated TGFβ receptor complex, Smurf2 does not alter the steady state level and turnover of Smad7. Recruitment of Smurf2 to the TGFβ receptor by Smad7 promotes the degradation of the Smad7-TGFβ receptor complex by both proteasomal and lysosomal pathways. The studies described herein demonstrate that Smad7 functions as an adaptor protein that recruits Smurf2 to the TGFβ receptor complex to promote its degradation and thereby down-regulate activated TGFβ receptor complexes. Regulation of Smad 7 localization to the nucleus and interaction with Smurf2 may be used to control the inhibitory activity of the Smad 7-Smurf2 complex.

The invention further provides a nucleic acid encoding Smurf2 [SEQ ID NO: 3], in addition to the Smurf 2 protein [SEQ ID NO: 4] and variants thereof.

E3 ubiquitin ligases display very selective substrate specificity, as is evident in the findings discussed herein. For example, Smurf1 binds BMP pathway-specific Smads. Moreover, Smurf1 is a unique signaling protein of the BMP pathway because it binds only to Smad1 and Smad5 and has little affinity for Smad 2 (specific for TGFβ and activin receptor pathways), and no affinity for Smad4 (common Smad signaling partner). As a result of this substrate specificity, Smurf1 can effectively interfere or regulate biological responses to BMPs without consequence to activin pathways, i.e., effects on other TGFβ signaling pathways are limited, or non-existent.

BMPs/TGFβ signalling pathway functions in tissue differentiation, morphogenesis, and cell growth control (e.g., (52)). As an antagonist to the signal transduction pathway mediated by the TGFβ family, Smurf1 will inhibit the BMP pathway in vivo or in vitro. As an integral component of regulatory system for degradation of TGFβ receptors, Smurf2 will inhibit the TGFβ signalling pathway. As a result, the Smurfs will block chondrogenesis, osteogenesis, blood differentiation, cartilage formation, neural tube patterning, retinal development, heart induction and morphogenesis, hair growth, tooth formation, gamete formation and a wide variety of tissue and organ formation processes, and hinder the regeneration, growth, maintenance, etc., of bone and other tissues that are dependent on the BMP pathway.

In one embodiment, mutant forms of a Smurf protein or small molecule antagonists of Smurf, described infra, can be used to prevent ubiquitination of proteins, e.g., Smads or TGFβ receptor, and therefore to preserve the signal transduction pathway mediated by BMPs. In addition, fragments of Smads can be generated that bind to either the Hect domain of a Smurf protein, which domain has the catalytic activity needed for ubiquitination of Smads, or to the WW domains that interact with the PPXY domains of Smads, thus precluding Smurf1 from binding and ubiquitinating Smads. These fragments can also be used in screening assays for small molecule inhibitors of Smurf-Smad interaction, e.g., in an inhibition binding assay. Variants of a Smurf protein and fragments of Smads can be used to improve defective BMP and/or TGFβ/activin signaling as a result of overexpressed or increased Smurf activity, which may contribute to a disease state.

BMPs control bone differentiation and growth, and are already in clinical tests and applications related to bone growth and connective tissue repair. Smurf proteins represent a novel target for the discovery of drugs that can influence its function, thereby affecting cellular responses to BMPs, and thus having clinical applications. Therefore, a Smurf protein can be used for screening for various drugs and/or antibodies that can either enhance the BMP pathway, or inhibit it by antagonizing or mimicking the activity of the protein, respectively. For example, since Smurf1 is highly specific for binding Smads1 and 5, it can be used to screen for drugs that block or activate the BMP pathway, and selectively affect cellular responses to BMPs without consequence to other members of the TGFβ superfamily.

Smurf proteins operate within cells, at the level of Smad signal transduction, and therefore provide an alternative means to affect BMP and TGFβ/activin signals. However, because Smurf proteins are intracellular proteins, any manipulations aimed at directly altering Smurf activity must operate intracellularly. Such manipulations include antisense and ribozyme technology, and intracellular antibody technology.

Smurf may be delivered to cells in gene therapy regimens to block excessive signaling by particular growth factor pathways controlled by Smads, e.g., Smads that are targets for Smurf1 or Smurf2. The examples herein show that simply increasing the expression levels of Smurf1 in cells antagonizes the Smad signaling pathway. Thus overexpression of Smurfs by gene therapy may be used to correct clinical conditions that result from excessive Smad signaling. These may include, for example, hyperplasia of bone, tendon or cartilage tissues, or formation of other tissues, that are regulated by signals from receptors (such as BMP receptors) that utilize Smad1 or Smad5 for signal transduction.

Smurf nucleic acids or partial sequences thereof (such as PCR probes) would be useful as molecular probes for identification of defective Smurf genes in the human genome, particularly where a mutation of a Smurf gene is found in association with a particular disease. Smurf proteins may be used as reagents for in vitro assays to identify proteins in cells that are targets for ubiquitination. Purified Smurfs may be reconstituted with purified ubiquitination enzymes (i.e. E1 and E2 components) and utilized in functional (ubiquitination) assays that are aimed at identifying novel target proteins introduced into the assays (as purified proteins or translated cDNAs of unknown identity).

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

If appearing herein, the following terms shall have the definitions set out below.

The term "about" or "approximately" means within 20%, preferably within 10%, and more preferably within 5% of a given value or range.

As used herein, the term "isolated" means that the referenced material is free of components found in the natural environment in which the material is normally found. In particular, isolated biological material is free of cellular components. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules can be inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

A "gene" is used herein to refer to a portion of a DNA molecule that includes a polypeptide coding sequence operatively associated with expression control sequences. In one embodiment, a gene can be a genomic or partial genomic sequence, in that it contains one or more introns. In another embodiment, the term gene refers to a cDNA molecule (i.e., the coding sequence lacking introns).

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Expression control sequences", e.g., transcriptional and translational control sequences, are regulatory sequences that flank a coding sequence, such as promoters, enhancers, suppressors, terminators, and the like, and that provide for the expression of a coding sequence in a host cell. In eukaryotic cells, polyadenylation signals are control sequences. On mRNA, a ribosome binding site is an expression control sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if it contains introns) and translated into the protein encoded by the coding sequence.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

A "vector" is a recombinant nucleic acid construct, such as plasmid, phage genome, virus genome, cosmid, or artificial chromosome to which another DNA segment may be attached. In a specific embodiment, the vector may bring about the replication of the attached segment, e.g., in the case of a cloning vector. A segment of DNA is inserted into a vector at specific restriction sites. The segment of DNA encodes a polypeptide of interest and the segment and restriction sites are designed to ensure insertion of the segment in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a Smurf1 or Smurf2 gene is heterologous to the plasmid vector DNA in which it is inserted for cloning or expression, and it is heterologous to a non-human host cell in which it is expressed, e.g., a CHO cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix.

Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The invention provides antisense nucleic acids (including ribozymes), which may be used to inhibit expression of Smurf1, particularly to enhance the BMP pathway via Smads1 and 4. Thus, antisense nucleic acids corresponding to the Smurf1 gene, or a fragment thereof, can be used to alter BMP pathways. The invention also provides antisense nucleic acids to inhibit expression of Smurf2, to enhance the TGFβ signalling pathway. An "antisense nucleic acid" is a single stranded nucleic acid molecule which, upon hybridizing with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

As used herein, the term "oligonucleotide" refers to a nucleic acid, generally of at least 10, preferably at least 15, and more preferably at least 20 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of Smurf1 or Smurf2, or to detect the presence of nucleic acids encoding Smurf1 or Smurf2. In a further embodiment, an oligonucleotide of the invention can form a triple helix with a Smurf1 or Smurf2 DNA molecule. In still another embodiment, a library of oligonucleotides arranged on a solid support, such as a silicon wafer or chip, can be used to detect various polymorphisms of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific examples of synthetic oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$).

U.S. Pat. No. 5,677,437 describes heteroaromatic oligonucleoside linkages. Nitrogen linkers or groups containing nitrogen can also be used to prepare oligonucleotide mimics (U.S. Pat. No. 5,792,844 and No. 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

As used herein, the term "homologous" in all its grammatical forms and spelling variations refers to the relationship between proteins that possess a "common evolutionary origin," including proteins from superfamilies (e.g., the TGFβ superfamily) and homologous proteins from different species (e.g., Smad (human), Mad (*Drosophila*), etc.) (Reeck et al., Cell 50:667, 1987). Such proteins, and their encoding genes, have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 70-75%, and most preferably at least about 80-85% of the nucleotides match over the defined length of the DNA sequences. An example of such a sequence is an allelic or species variant of a Smurf gene of the invention. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 70% of the amino acids are identical, or greater than about 90% are similar (functionally similar). Preferably, the similar or homologous sequences are identified by alignment using, for example, the GCG (Genetics Computer Group, Program Manual for the GCG Package, *Version* 7, Madison, Wis.) pileup program, BLAST, and Clustal W analysis (MacVector). Sequence comparison algorithms can also be found at www.nwfsc.noaa.gov/bioinformatics.html.

The term "corresponding to" is used herein to refer similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A nucleic acid coding a protein of the Smurf family, e.g., Smurf1 or Smurf2, whether genomic DNA or cDNA, can be isolated from any source, particularly from a human or *Xenopus* cDNA or genomic library. Methods for obtaining genes are well known in the art, as described above (see, e.g., Sambrook et al., 1989, supra). In a specific embodiment, the invention provides cDNA sequences for human Smurf1 (hSmurf1) and Smurf2 (hSmurf2) genes [SEQ ID NO: 1 and SEQ ID NO: 3].

Accordingly, any animal cell can potentially serve as the nucleic acid source for the molecular cloning of a Smurf gene. The DNA may be obtained by standard procedures known in the art from cloned DNA (e.g., a DNA "library"), including EST libraries and cDNA libraries prepared from tissues with high level expression of the protein (e.g., a *Xenopus* Stage 9 (blastula) cDNA library—these are the cells that evidence the highest levels of expression of Smurf1). Other cell lines that may express Smurf1 or Smurf2 are frog blastula and gastrula ectoderm, mesoderm, and endoderm; mouse embryonic stem cells; and various mammalian cells, such as NIH3T3, PC12, 293T, Hela, and COS. DNA encoding a Smurf protein can also be obtained by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Identification of a specific DNA fragment containing a desired Smurf gene can be accomplished in various ways known in the art. For example, a portion of a Smurf gene exemplified below can be purified and labeled to prepare a labeled probe, and the generated DNA may be screened by nucleic acid hybridization to the labeled probe (Benton and Davis, Science 196:180, 1977; Grunstein and Hogness, Proc. Natl. Acad. Sci. U.S.A. 72:3961, 1975). Those DNA fragments with substantial homology to the probe, such as an allelic variant from another individual, will hybridize. In a specific embodiment, high stringency hybridization conditions are used to identify a homologous Smurf1 or Smurf2 gene.

The present invention also relates to cloning vectors containing genes encoding analogs and derivatives of a Smurf gene of the invention, e.g., Smurf1 or Smurf2, that have similar or homologous functional activity. The production and use of derivatives and analogs related to Smurf1 and Smurf2 are within the scope of the present invention. For example, a truncated form of Smurf1 or Smurf2 can be provided. Such a truncated form includes Smurf1 or Smurf2 with a deletion. In a specific embodiment, the derivative or analog is functionally active, i.e., capable of exhibiting one or more functional activities associated with a full-length, wild-type Smurf1 or Smurf2 of the invention. Such functions include binding to a Smad protein, e.g., Smad1, Smad5 or Smad7, and catalyzing the ubiquitination of the bound Smad, of the activated TGFβ receptor/Smad complex, or another protein in a TGFβ/activin pathway. In another embodiment, the fragment has binding affinity but lacks or has reduced catalytic capacity.

A Smurf derivative can be made by altering encoding nucleic acid sequences by substitutions, additions or deletions that provide for functionally equivalent molecules. Alternatively, non-functional mutant forms of the Smurf proteins, that may for example compete with the wild-type Smurf protein in the BMP pathway, but which are less effective in ubiquitination of Smads, can be prepared for use in treating disorders associated with compromised BMP signaling pathways as described above. In a specific embodiment, infra, the mutation is C710A, described further in the Examples. In another specific embodiment, with respect to Smurf 2, the mutation is C716A.

Further selection can be carried out on the basis of the properties of the gene, e.g., if the gene encodes a protein product having the isoelectric, electrophoretic, amino acid composition, partial or complete amino acid sequence, antibody binding activity, or ligand binding profile of a Smurf protein as disclosed herein. Thus, the presence of the gene may be detected by assays based on the physical, chemical, immunological, or functional properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as determined for Smurf1, or Smurf2.

The present invention also relates to analogs, and derivatives of a Smurf protein, homologs from other species, and mutant variants, which have the same or a homologous functional activity. The production and use of derivatives, analogs, and mutant variants related to a Smurf protein are within the scope of this invention. In a specific embodiment, the derivative or analog is functionally active, i.e., capable of exhibiting one or more functional activities associated with a full-length, wild-type Smurf1 or Smurf2 protein of the invention.

Smurf derivatives can be made by altering nucleic acid sequences by substitutions, additions or deletions that provide for functionally equivalent molecules. Preferably, derivatives are made that have enhanced functional activity relative to a native Smurf. e.g., Smurf1 or Smurf2, or that lack a functional activity, such as catalytic activity in the Hect ubiquitin-ligase domain in the C-terminal portion of the Smurf proteins. In one specific embodiment, mutant hSmurf1 having a point mutant at C710A is provided which disrupts the catalytic activity of the Hect domain thereby precluding ubiquitination of Smads1 and 4. In another specific embodiment, mutant hSmurf2 having a point mutation at C716A is provided which disrupts the catalytic activity of the Hect domain, precluding proteolytic degradation of the TGFβ receptor-Smad 7 complex. Alternatively, Smurf protein derivatives may encode soluble fragments of a Smurf protein domain, e.g., WW domain, that have the same or greater affinity for the natural ligands, e.g. Smads1, 5 or 7. Such soluble derivatives may be potent inhibitors of ligand (i.e., Smads1, 5 or 7) binding to the Smurf proteins.

In another specific embodiment, derivatives or fragments of Smads 1 and 4 can be made that bind Smurf1 and preclude the E3 ligase from further binding cellular Smad and preventing its ubiquitination. In another embodiment, derivatives or fragments of Smad 7 can be made that reduce the association of Smurf2 to both Smad 7 and the TGFβ receptor. Thus, in one embodiment the invention contemplates use of peptides containing the linker region of R-Smads having a PPXY sequence, which is a conserved motif recognized by WW domains (see, Rotin, Curr. Topics Microbiol. Immunol., 228:115-133, 1998 and (33)) such as those found in Smurf1 or Smurf2, and corresponding nucleic acid sequences.

Due to the degeneracy of nucleotide coding sequences, other DNA sequences which encode substantially the same amino acid sequence as a Smurf gene may be used in the practice of the present invention. These include but are not limited to allelic genes, homologous genes from other species, and nucleotide sequences comprising all or portions of Smurf genes which are altered by the substitution of different codons that encode the same amino acid residue within the sequence, thus producing a silent change. Likewise, Smurf derivatives of the invention include, but are not limited to, those containing, as a primary amino acid sequence, all or part of the amino acid sequence of a Smurf protein, including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point. Particularly preferred substitutions include:

Lys for Arg and vice versa such that a positive charge may be maintained;

Glu for Asp and vice versa such that a negative charge may be maintained;

Ser for Thr such that a free —OH can be maintained; and

Gln for Asn such that a free $CONH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces b-turns in the protein's structure.

The genes encoding Smurf derivatives and analogs of the invention can be produced by various methods known in the art. The manipulations which result in their production can occur at the gene or protein level. For example, a cloned Smurf1 or Smurf2 gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a Smurf, care should be taken to ensure that the modified gene remains within the same translational reading frame as the gene, uninterrupted by translational stop signals, in the gene region where the desired activity is encoded.

Additionally, a Smurf-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated Smurf gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479-488; Oliphant et al., 1986, Gene 44:177; Hutchinson et al., 1986, Proc. Natl. Acad. Sci. U.S.A. 83:710), use of TAB" linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pMal-c, pFLAG, pGBT9, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2µ plasmid.

Expression of Smurf Polypeptides

The nucleotide sequence coding for a Smurf protein, or antigenic fragment, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a Smurf protein of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a Smurf protein and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. The host cell containing the recombinant vector comprising the nucleic acid encoding a Smurf protein of the invention is cultured in an appropriate cell culture medium under conditions that provide for expression by the cell. Useful host cells for expression of Smurf include $C_2C_{12}$, 293T, CHO, COS, HEK, Hela, HepG2, NIH3T3, PC12, P19 and other cell lines, and kidney, brain, and bone cells.

A recombinant Smurf protein of the invention, or functional fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a Smurf protein may be controlled by any promoter/enhancer element known in the art, but these regulatory elements must be functional in the host selected for expression. Promoters which may be used to control Smurf gene expression include, but are not limited to, the SV40 early promoter region (Benoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987, Cell 48:703-712), myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31-40), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences, and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen (195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991)). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and b-gal selection), pMJ601 (SalI, SmaI, AflI, NarI, BspMII, BamHI, ApaI, NheI, SacII, KpnI, and HindIII cloning site; TK- and b-gal selection), and pTKgptF1S (EcoRI, PstI, SalI, AccI, HindIII, SbaI, BamHI, and Hpa cloning site, TK or XPRT selection).

Yeast expression systems can also be used according to the invention to express Smurf1. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant Smurf DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification of proteins. Appropriate cell lines or host systems can be chosen to ensure the desired modification and processing of the foreign protein expressed. For example, expression in a bacterial system can be used to produce a nonglycosylated core protein product, while expression in yeast can produce a glycosylated product. Expression in eukaryotic cells can increase the likelihood of "native" folding of a heterologous mammalian protein. Moreover, expression in mammalian cells can provide a tool for reconstituting, or constituting, Smurf activity. Furthermore, it is known in the art that different vector/host expression systems may affect processing reactions (e.g., proteolytic cleavages) to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Analysis of Gene Expression Mediated by Smurf Functional Activity

In one embodiment, oligonucleotide array technology can be used, e.g., to evaluate gene expression, after binding of Smurf1 to Smads1 or 5, or binding of Smurf2 to Smad7, and to identify gene expression that correlates with, or is distinct from, gene expression in TGFβ or BMP treated cells or cells of injured and/or healing tissue, tissue having cells in a tumorigenic state, and during cellular and developmental processes, such as mitosis, cell differentiation, embryonic pattern formation and development and organogenesis. For example, one could compare gene expression in TGFβ or BMP treated cells in the presence or absence of Smurf expression. GeneChip expression analysis (Affymetrix, Santa Clara, Calif.) generates data for the assessment of gene expression profiles and other biological assays. Oligonucleotide expression arrays simultaneously and quantitatively interrogate thousands of mRNA transcripts (genes or ESTs), simplifying large genomic studies. Each transcript can be represented on a probe array by multiple probe pairs to differentiate among closely related members of gene families. Each probe cell contains millions of copies of a specific oligonucleotide probe, permitting the accurate and sensitive detection of low-intensity mRNA hybridization patterns. Differential expression data can provide a clear understanding of cellular pathways.

After hybridization intensity data is captured, e.g., using a Hewlett-Packard GeneArray™ scanner. Software can be used to automatically calculate intensity values for each probe cell. Probe cell intensities can be used to calculate an average intensity for each gene, which directly correlates with mRNA abundance levels. Expression data can be quickly sorted on any analysis parameter and displayed in a variety of graphical formats for any selected subset of genes. Standard and custom GeneChip expression probe arrays are available today for human, mouse, yeast and other organisms. The GeneChip product line will expand to include expression arrays for the analysis of additional organisms and application areas such as toxicology and pharmacogenomics.

Transgenic Vectors

Smurf can be introduced into cells to treat a disorder associated with excess BMP or TGFβ activation, such as cancer. Smurf activity can be evaluated by introducing a Smurf vector into a cell and monitoring the cell upon Smurf expression. This can be done in vitro or in vivo, or in vitro followed by transplantation in vivo, also termed ex vivo. Alternatively, as discussed above, Smurf or a Smurf inhibitor (antisense, ribozyme, or intracellular antibody) can be delivered by a vector in modulate Smads, e.g., to prevent Smurf regulation of Smads where BMP or TGFβ activity is desired, such as in bone regeneration, or to study Smurf regulated processes in vivo.

Smurf activity can be inhibited by various means, including by delivery of a vector encoding a dominant-negative Smurf derivative (e.g., a Cys710 to Ala mutant) to cells, by antisense nucleic acids (including ribozymes and triple-helix-forming oligonucleotides; these are described in detail supra), and by expression of anti-Smurf intracellular antibodies, e.g., single chain Fv antibodies (see generally Chen, Mol. Med. Today, 3: 160-167, 1997; Spitz et al., Anticancer Res., 16:3415-3422, 1996; Indolfi et al., Nat. Med., 2:634-635, 1996; Kijima et al., Pharmacol. Ther., 68:247-267, 1995).

As discussed above, a vector is any means for the transfer of a nucleic acid according to the invention into a host cell. These include viral vectors, such as lentiviruses, retroviruses, herpes viruses, adenoviruses and adeno-associated viruses. Thus, a gene encoding a functional or mutant Smurf protein or polypeptide domain fragment thereof can be introduced in viva, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art [see, e.g., Miller and Rosman, BioTechniques 7:980-990 (1992)]. Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector [Kaplitt et al., Molec. Cell. Neurosci., 2:320-330 (1991)], defective herpes virus vector lacking a glyco-protein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest., 90:626-630, 1992; see also La Salle et al., Science, 259:988-990, 1993]; and a defective adeno-associated virus vector [Samulski et al., J. Virol., 61:3096-3101, 1987; Samulski et al., J. Virol., 63:3822-3828, 1989; Lebkowski et al., Mol. Cell. Biol., 8:3988-3996, 1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-g (IFN-g), or anti-CD4 antibody, can be administered to block humoral or cellular immune responses to the viral vectors [see, e.g., Wilson,

*Nature Medicine* (1995)]. In addition, it is advantageous to employ a viral vector that is engineered to express a minimal number of antigens.

Adenovirus vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see WO94/26914). Those adenoviruses of animal origin which can be used within the scope of the present invention include adenoviruses of canine, bovine, murine (example: Mav1, Beard et al., Virology 75 (1990) 81), ovine, porcine, avian, and simian (example: SAV) origin. Preferably, the adenovirus of animal origin is a canine adenovirus, more preferably a CAV2 adenovirus (e.g. Manhattan or A26/61 strain (ATCC VR-800), for example).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (WO95/02697), the E2 region (WO94/28938), the E4 region (WO94/28152, WO94/12649 and WO95/02697), or in any of the late genes L1-L5.

In a specific embodiment, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO95/02697 and WO96/22378, the contents of which are incorporated herein by reference. In still another preferred embodiment, the adenoviral vector has a deletion in the E1 region into which the E4 region and the nucleic acid sequence are inserted (see FR94 13355, the contents of which are incorporated herein b) reference).

The replication defective recombinant adenoviruses according to the invention can be prepared by any technique known to the person skilled in the art (Levrero et al., Gene 101:195 1991; EP 185 573; Graham, EMBO J. 3:2917, 1984). In particular, they can be prepared by homologous recombination between an adenovirus and a plasmid which carries, inter alia, the DNA sequence of interest. The homologous recombination is effected following cotransfection of the said adenovirus and plasmid into an appropriate cell line. The cell line which is employed should preferably (i) be transformable by the said elements, and (ii) contain the sequences which are able to complement the part of the genome of the replication defective adenovirus, preferably in integrated form in order to avoid the risks of recombination. Examples of cell lines which may be used are the human embryonic kidney cell line 293 (Graham et al., J. Gen. Virol. 36:59 1977) which contains the left-hand portion of the genome of an Ad5 adenovirus (12%) integrated into its genome, and cell lines which are able to complement the E1 and E4 functions, as described in applications WO94/26914 and WO95/02697. Recombinant adenoviruses are recovered and purified using standard molecular biological techniques, which are well known to one of ordinary skill in the art.

Adeno-associated viruses. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions which carry the encapsidation functions: the left-hand part of the genome, which contains the rep gene involved in viral replication and expression of the viral genes; and the right-hand part of the genome, which contains the cap gene encoding the capsid proteins of the virus.

The use of vectors derived from the AAVs for transferring genes in vitro and in vivo has been described (see WO 91/18088; WO 93/09239; U.S. Pat. No. 4,797,368, U.S. Pat. No. 5,139,941, EP 488 528). These publications describe various AAV-derived constructs in which the rep and/or cap genes are deleted and replaced by a gene of interest, and the use of these constructs for transferring the said gene of interest in vitro (into cultured cells) or in vivo, (directly into an organism). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus vectors. In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; EP 453242, EP178220; Bernstein et al. Genet. Eng. 7 (1985) 235; McCormick, BioTechnology 3 (1985) 689; International Patent Publication No. WO 95/07358, published Mar. 16, 1995, by Dougherty et al.; and Kuo et al., 1993, Blood 82:845. The retroviruses are integrating viruses which infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed which contains the LTRs, the encapsidation sequence and the coding sequence. This construct is used to transfect a packaging cell line, which cell line is able to supply in trans the retroviral functions which are deficient in the plasmid. In general, the packaging cell lines are thus able to express the gag, pol and env genes. Such packaging cell lines have been described in the prior art, in particular the cell line PA317 (U.S. Pat. No. 4,861,719); the PsiCRIP cell line (WO90/02806) and the GP+envAm-12 cell line (WO89/07150). In addition, the recombinant retroviral vectors can contain modifications within the LTRs for suppressing transcriptional activity as well as extensive encapsidation sequences which may include a part of the gag gene (Bender et al., J. Virol. 61 (1987) 1639). Recombinant retroviral vectors are purified by standard techniques known to those having ordinary skill in the art.

Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Lentivirus vectors. In another embodiment, lentiviral vectors are can be used as agents for the direct delivery and sustained expression of a transgene in several tissue types, including brain, retina, muscle, liver and blood. The vectors can efficiently transduce dividing and nondividing cells in these tissues, and maintain long-term expression of the gene of interest.

Lentiviruses contain at least two regulatory genes, tat and rev, that are essential for replication, and four accessory genes that encode critical virulence factors. [For a review, see Naldini, L., Curr. Opin. Biotechnol., 9:457-63, 1998]. The viral sequences non-essential for transduction are eliminated thereby improving the biosafety of this particular vector. Self-inactivating HIV-1 vectors are known, which have a deletion in the 3' long terminal repeat (LTR) including the TATA box, and significantly improve the biosafety of HIV-derived vectors by reducing the likelihood that replication-competent retroviruses will originate in the vector producer and target cells (Zufferey, et al., J. Virol., 72:9873-80, 1998). In addition, the deletion improves the potential performance of the vector by removing LTR sequences previously associated with transcriptional interference and suppression in vivo and by allowing the construction of more-stringent tissue-specific or regulatable vectors.

Lentiviral packaging cell lines are available and known generally in the art. They facilitate the production of high-titer lentivirus vectors for gene therapy. An example is a tetracycline-inducible VSV-G pseudotyped lentivirus packaging cell line which can generate virus particles at titers greater than 10(6) IU/ml for at least 3 to 4 days (Kafri, et al., J. Virol., 73: 576-584, 1999). The vector produced by the inducible cell line can be concentrated as needed for efficiently transducing nondividing cells in vitro and in vivo.

Non-viral vectors. Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al. Proc. Natl. Acad. Sci. U.S.A., 84:7413-7417, 1987; see Mackey, et al., Proc. Natl. Acad. Sci. U.S.A., 85:8027-8031, 1988; Ulmer et al., Science, 259:1745-1748, 1993]. The use of cationic lipids may promote encapsulation of negatively charged nucleic acids, and also promote fusion with negatively charged cell membranes [Felgner and Ringold, Science, 337:387-388, 1989]. Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., J. Biol. Chem., 267:963-967, 1992; Wu and Wu, J. Biol. Chem., 263:14621-14624, 1988; Hartmut et al., Canadian Patent Application No. 2,012,311, filed Mar. 15, 1990; Williams et al., Proc. Natl. Acad. Sci. USA, 88:2726-2730, 1991]. Receptor-mediated DNA delivery approaches can also be used [Curiel et al., Hum. Gene Ther., 3:147-154, 1992; Wu and Wu, J. Biol. Chem., 262:4429-4432, 1987]. U.S. Pat. No. 5,580,859 discloses delivery of exogenous DNA sequences, free of transfection facilitating agents, in a mammal.

Antibodies Against Smurf Proteins

According to the invention, a Smurf polypeptide produced recombinantly or by chemical synthesis, and fragments, variants, or other derivatives or analogs thereof, including fusion proteins, may be used as an immunogen to generate antibodies that recognize a Smurf polypeptide. Such antibodies include but are not limited to polyclonal, monoclonal, chimeric, single chain, Fab fragments, and a Fab expression library. Such an antibody is specific for Smurf proteins; it may recognize a mutant form of a Smurf, or wild-type Smurf. These antibodies can be used to alter the BMP pathway by inhibiting a Smurf protein (e.g., anti-Smurf intracellular antibodies) or for diagnostic purposes.

Various procedures known in the art may be used for the production of polyclonal antibodies to a Smurf polypeptide or derivative or analog thereof. For the production of antibody, various host animals can be immunized by injection with a Smurf polypeptide, or a derivative (e.g., fragment or fusion protein) thereof, including but not limited to rabbits, mice, rats, sheep, goats, etc. In one embodiment, a Smurf polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward a Smurf polypeptide, or fragment, analog, or derivative thereof, any technique that provides for the production of antibody molecules by continuous cell lines in culture may be used. These include but are not limited to the hybridoma technique originally developed by Kohler and Milstein (Nature 256:495-497, 1975), as well as the trioma technique, the human B-cell hybridoma technique (Kozbor et al., Immunology Today 4:72, 1983; Cote et al., Proc. Natl. Acad. Sci. U.S.A. 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690, published 28 Dec. 1989). In fact, according to the invention, techniques developed for the production of "chimeric antibodies" (Morrison et al., J. Bacteriol. 159:870, 1984; Neuberger et al., Nature 312:604-608, 1984; Takeda et al., Nature 314:452-454, 1985) by splicing the genes from a mouse antibody molecule specific for a Smurf polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

In accordance with the invention, techniques described for the production of single chain antibodies (U.S. Pat. Nos. 5,476,786 and 5,132,405 to Huston; U.S. Pat. No. 4,946,778) can be adapted to produce a Smurf polypeptide-specific single chain antibodies. An additional embodiment of the invention utilizes the techniques described for the construction of Fab expression libraries (Huse et al., Science 246:1275-1281, 1989) to allow rapid and easy identification of monoclonal Fab fragments with the desired specificity for a Smurf polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Smurf activity can also be inhibited by expression of anti-Smurf intracellular antibodies, e.g., single chain Fv antibodies, using techniques known in the art (see generally Chen, Mol. Med. Today 3:160-167, 1997; Spitz, et al., Anticancer Res. 16:3415-3422, 1996; Indolfi et al., Nat. Med. 2:634-635, 1996; Kijima et al., Pharmacol. Ther. 68:247-267, 1995).

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a Smurf polypeptide, one may assay generated hybridomas for a product which binds to a Smurf polypeptide fragment containing such epitope. For selection of an antibody specific to a Smurf polypeptide from a particular species of animal, one can select on the basis of positive binding with a Smurf polypeptide expressed by or isolated from cells of that species of animal.

The foregoing antibodies can be used in methods known in the art relating to the localization and activity of a Smurf polypeptide, e.g., for Western blotting, imaging a Smurf polypeptide in situ, measuring levels thereof in appropriate physiological samples, etc., using any of the detection techniques mentioned above or known in the art. Such antibodies can also be used in assays for ligand binding, e.g., as described in U.S. Pat. No. 5,679,582.

In a specific embodiment, antibodies that agonize or antagonize the activity of a Smurf polypeptide can be generated. Such antibodies can be tested using the assays described infra for identifying ligands.

Screening

According to the present invention, nucleotide sequences derived from the gene encoding a Smurf, and peptide sequences derived therefrom, are useful targets to identify drugs that are effective in treating disorders mediated by the BMP signaling pathway, as discussed above (see, Schmitt et al., J. Orthopedic Res., 17:269, 1999) can be used to agonize or antagonize a Smurf protein. Drug targets include without limitation (i) isolated nucleic acids derived from the gene encoding a Smurf and (ii) isolated peptides and polypeptides derived from Smurf polypeptides.

In particular, identification and isolation of a Smurf protein provides for development of screening assays, particularly for high throughput screening of molecules that up- or down-regulate the activity of a Smurf, e.g., by permitting expression of a Smurf protein in quantities greater than can be isolated from natural sources, or in indicator cells that are specially engineered to indicate the activity of a Smurf protein expressed from a gene after transfection or transformation of the cells. Accordingly, the present invention contemplates methods for identifying specific ligands of a Smurf protein using various screening assays known in the art.

Any screening technique known in the art can be used to screen for agonists or antagonists of a Smurf protein. The present invention contemplates screens for small molecule ligands or ligand analogs and mimics, as well as screens for natural ligands that bind to and agonize or antagonize a Smurf protein in vivo. For example, natural products libraries can be screened using assays of the invention for molecules that agonize or antagonize Smurf activity.

Knowledge of the primary sequence of Smurf1 and Smurf2, and the similarity of that sequence with proteins of known function, provides one having ordinary skill in the art with useful information to determine inhibitors or antagonists of a Smurf protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, Science 249:386-390, 1990; Cwirla, et al., Proc. Natl. Acad. Sci., 87:6378-6382, 1990; Devlin et al., Science, 49:404-406, 1990), very large libraries can be constructed ($10^6$-$10^8$ chemical entities). A second approach uses primarily chemical methods, of which the Geysen method (Geysen et al., Molecular Immunology 23:709-715, 1986; Geysen et al. J. Immunologic Method 102:259-274, 1987; and the method of Fodor et al. (Science 251:767-773, 1991) are examples. Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700-4, 1993; Ohlmeyer et al., Proc. Natl. Acad. Sci. USA 90:10922-10926, 1993; Lam et al., International Patent Publication No. WO 92/00252; Kocis et al., International Patent Publication No. WO 9428028) and the like can be used to screen for Smurf ligands according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (NC), or are readily producible. Additionally, natural and synthetically produced libraries and compounds are readily modified through conventional chemical, physical, and biochemical means (Blondelle et al., Tib Tech, 14:60, 1996).

In Vitro Screening Methods

In one series of embodiments, an isolated nucleic acid comprising a Smurf gene is tested in vitro for its ability to bind test compounds in a sequence-specific manner. The methods comprise:

(i) providing a nucleic acid containing a particular sequence corresponding to all or portions of a Smurf protein;

(ii) contacting the nucleic acid with a multiplicity of test compounds under conditions appropriate for binding; and (iii) identifying those compounds that bind selectively to the nucleic acid sequence.

Selective binding as used herein refers to any measurable difference in any parameter of binding, such as, e.g., binding affinity, binding capacity, etc.

In one series of embodiments, an isolated peptide or polypeptide, or fragments thereof, comprising a Smurf protein is tested in vitro for its ability to bind test compounds in a sequence-specific manner. The screening methods involve:

(i) providing a peptide or polypeptide, or fragment thereof, corresponding to Smurf protein or a fragment thereof;

(ii) contacting the peptides with a multiplicity of test compounds under conditions appropriate for binding; and (iii) identifying those compounds that bind selectively to the peptides.

In preferred embodiments, high-throughput screening protocols are used to survey a large number of test compounds for their ability to bind the genes or peptides disclosed above in a sequence-specific manner.

In Vivo Screening Methods

Intact cells or whole animals expressing variants of a gene encoding a Smurf protein can be used in screening methods to identify candidate drugs. The following methods can be applied to normal or wild-type Smurf.

In one series of embodiments, a permanent cell line is established from an individual exhibiting expression of a variant Smurf gene. Alternatively, cells (including without limitation mammalian, mammalian, insect, yeast, and bacterial cells) are programmed to express a gene comprising one or more variant Smurf sequences by introduction of suitable vector. Identification of candidate compounds can be achieved using any suitable assay, including without limitation (i) assays that measure selective binding of test compounds to particular variant of a Smurf, (ii) assays that measure the ability of a test compound to modify (i.e., inhibit or enhance) a measurable activity or function of the Smurf; and (iii) assays that measure the ability of a compound to modify (i.e., inhibit or enhance) the transcriptional activity of sequences derived from the promoter (i.e., regulatory) regions of a Smurf gene.

In another series of embodiments, transgenic animals are created in which (i) a human Smurf, having one or more mutations is stably inserted into the genome of the transgenic animal; and/or (ii) endogenous Smurf genes are inactivated and replaced with a variant human Smurf gene. See, e.g., Coffman, Semin. Nephrol. 17:404, 1997; Esther et al., Lab. Invest. 74:953, 1996; Murakami et al., Blood Press. Suppl. 2:36, 1996. A preferred method for creating such a transgenic animal is so called "knock-in" technology, where a human gene can be inserted to replace an endogenous gene under expression control of the endogenous genes' regulatory elements (see, Rodriguez et al., Cell, 97:199, 1999). Such animals can be treated with candidate compounds and monitored for any alteration in the BMP and TGFβ/activin pathways.

Furthermore, populations that are not amenable to an established treatment for tissue and bone degeneration (e.g., osteoporosis) or enhancing regeneration can be selected for testing of alternative treatments. Moreover, treatments that are not as effective in the general population, but that are highly effective in the selected population, may be identified that otherwise would be overlooked. This is an especially powerful advantage of the present invention, since it eliminates some of the randomness associated with clinical trials.

High-Throughput Screen

Agents according to the invention may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time. Such high-throughput screening methods are particularly preferred. The use of high-throughput screening assays to test for agents is greatly facilitated by the availability of large amounts of purified polypeptides, as provided by the invention.

Reporter Genes

Smad proteins have been identified as mediators of intracellular signal transduction by members of the transforming growth factor-beta (TGF-beta) superfamily, which affect cell proliferation, differentiation, as well as pattern formation during early vertebrate development. Following receptor activation, Smads are assembled into heteromeric complexes consisting of a pathway-restricted Smad and the common Smad4 that are subsequently translocated into the nucleus where they are thought to play an important role in gene transcription. Smad Binding Elements (SBEs) containing the sequence CAGACA in the promoter of the JunB gene, is an immediate early gene that is potently induced by TGF-beta, activin, and bone morphogenetic protein (BMP) 2 (Jonk et al., J. Biol. Chem., 273:21145, 1998). Two JunB SBEs are arranged as an inverted repeat, which is transactivated in response to Smad3 and Smad4 co-overexpression and shows inducible binding of a Smad3- and Smad4-containing complex in nuclear extracts from TGF-beta-treated cells. Smad proteins bind directly to the SBE. Multimerization of the SBE creates a powerful TGF-beta-inducible enhancer that is also responsive to activin and BMPs (see, e.g., Kim et al., Nature, 388:304, 1997).

Reporter gene expression can be tied to expression or activation of any component of the BMP signaling pathway. Any reporter gene known in the art can be used. Thus, nucleotide sequences having the SBE sequence can be isolated using techniques known in the art and operably linked to a reporter gene to determine whether a Smurf, derivatives, and variants thereof, alter the activity of such promoter. In addition, other known genes in the BMP signaling pathway, such as T1x2 or Smad7, which have promoters that are regulated by Smad1 and 5 can be operably linked to a reporter gene. In these assays, candidate compounds can be tested for their ability to alter BMP of TGFβ signaling in cells that express Smad1, Smad5, Smad7, Smurf1 or Smurf2, or derivatives or variants thereof.

Various reporter gene assays are known and can be used to evaluate the effects of a Smurf on a BMP or TGFβ/activin signaling pathway. Reporter genes include luciferase, β-galactosidase (β-gal or lac-Z), chloramphenicol acetyltransferase (CAT), horseradish peroxidase, and alkaline phosphatase. In addition, expression of almost any protein can be detected using a specific antibody. For example, a green fluorescent protein (GFP) expression assay permits evaluation of Smad-induced SBE activity. GFP has been modified to produce proteins that remain functional but have different fluorescent properties. Several U.S. patents teach use of GFP to visualize signaling pathways linked to the reporter gene by an inducible promoter. For example, see U.S. Pat. No. 5,625,048 (modified GFP resulting in amino-acid changes provides visibly distinct colors and increased intensities of emission), WO96/23898 (construct encoding a modified GFP which also contains an enzyme recognition site), WO97/11094 (fluorescent proteins with increased intensity), WO97/266333 (humanized GFP protein optimized to provide higher levels of expression in mammalian cells), WO97/42320 (modified GFP having increased intensity of fluorescence, WO98/06737 (modified GFP easily distinguished from green and blue fluorescent proteins), WO98/21355 (GFP mutants excitable using blue and white light).

Screening Kits

The components required to practice the screening methods described above can be prepared in kit form, for the convenience of the user. Such kits are preferably adapted for use in an automated screening apparatus.

Identification of Smurf1 Binding Partners

In still another embodiment, the present invention provides for identification of Smurf binding partners, in addition to Smad1, Smad7 and Smad5, which can then be analyzed for mutations that lead to diseases mediated by the BMP or TGFβ/activin pathways. One method for identifying such binding partners is a yeast two hybrid assay system, preferably using a hematopoietic stem cell library with yeast that are transformed with a recombinant Smurf. Alternatively, a Smurf protein can be used to affinity purify proteins from cell preparations, e.g., using cells that endogenously produce Smurfs. Partially purified preparations can be probed with a labeled Smurf protein to identify specific binding partners, e.g., in a Western-type or other antibody-assay type of system (see the description above of antibodies for examples of such assays; naturally, any protein can be labelled as an antibody and its binding to a binding partner evaluated).

EXAMPLES

The present invention may be better understood by reference to the following examples, which are not intended to limit the invention.

Example 1

Smurf1 targets the BMP pathway and affects embryonic pattern formation. The TGFβ superfamily regulates diverse biological processes including cell growth, differentiation and pattern formation. Any misregulation of TGFβ signals may cause disease. Signals from activated TGFβ receptors are directly transduced from receptor to nucleus by Smad proteins. Currently, a few links have been established between ubiquitin-mediated degradation and the modulation of morphogenic signaling during development. This Example describes a new E3 ubiquitin ligase, Smurf1, that selectively interacts with BMP pathway-specific Smads to trigger their ubiquitination, degradation and loss of activity. In amphibian embryos, Smurf1 specifically blocked BMP signals and affected pattern formation. Thus, targeted ubiquitination of Smads may function to control both embryonic development and a wide variety of cellular responses to TGFβ signals.

Methods

Yeast two-hybrid screen. A *Xenopus* Smad1 cDNA (36) was cloned into the pGBT9 vector and used to screen a *Xenopus* oocyte cDNA library (Clonetech) by the yeast two-hybrid method (46) using *Xenopus* Smad1 as the bait protein. A partial cDNA was isolated and used to screen a *Xenopus* Stage9 (blastula) cDNA library to obtain a full length Smurf1 cDNA [SEQ ID NO: 1]. A human Smurf1 cDNA encoding all but the first 8 amino acids was identified in the EST database (AA292123), and was used to construct human Smurf1. The first 8 amino acids were reconstituted using the corresponding *Xenopus* Smurf1 cDNA sequence. hSmurf cDNA was FLAG tagged at its N-terminus. The ubiquitin ligase mutant version of hSmurf1 was generated by replacing cysteine 710 with alanine using a PCR-based approach and the mutation was confirmed by sequencing.

Co-immunoprecipitation. For immunoprecipitation assays, *Xenopus* Smad1 (36), mouse Smad4, and human Smad2 (47), were FLAG-tagged at their C-termini and translated in vitro (rabbit reticulocyte extracts; Promega) in the presence of $^{35}$S-Met. The FLAG-tagged Smads were bound to anti-FLAG antibody-conjugated beads (Kodak), washed in co-IP buffer (10 mM TRIS (tris(Hydroxymethyl) aminomethane), pH 7.5, 90 mM NaCl, 1 mM EDTA, 1% TRITON X-100, 10% glycerol, 1 mM phenylmethylsulfonylfluoride) then incubated with $^{35}$S-Met-labelled Smurf1 in the same buffer. After washing in co-IP buffer and elution in gel loading buffer, proteins were separated by SDS-PAGE and visualized by autoradiography.

Embryo methods and RT-PCR. Embryo production, preparation and injection of synthetic mRNA into embryos, animal cap and ventral marginal zone assays, embryonic RNA isolation, embryo fixation and whole mount in situ hybridization, and developmental RT-PCR were performed as described (36, 48). Primers for Smurf1 RT-PCR were 5'-GTCCTGTGACTGGAACCC-3' (sense) [SEQ ID NO: 5] and 5'-.GAGGACTGCTAGACAAT-3' (antisense) [SEQ ID NO: 6], whose 5' ends are respectively located at positions 482 and 726 in the Smurf1 cDNA.

mSmurf1. Northern blots were performed of mSmurf1 expression in embryonic and adult mouse tissues. Equal amounts of PolyA+ mRNA from embryonic tissue 7, 11 and 15 days post coitum and tissue samples from testes, kidney, skeletal muscle, lung, spleen, brain and heart were analyzed. Cytoskeletal actin expression was assayed on the same blot and verified that mRNA loading was equal in all lanes. Whole-mount in situ hybridization on mouse embryos were also performed.

Immunoprecipitations and Immunoblotting. COS-1 and 293T cells were transiently transfected using lipofectAMINE (GibroBRL) and calcium phosphate precipitation methods, respectively (49). Immunoprecipitations and immunoblotting were performed as described previously (50) using anti-Flag M2 monoclonal antibody (Sigma), anti-Smad1/5 polyclonal antibody (50) or anti-WW2 Nedd4 (51) polyclonal antibody. Detection was achieved using the appropriate HRP conjugated goat anti-mouse or goat anti-rabbit secondary antibodies and enhanced chemiluminescence (Amersham).

Pulse Chase Analysis. COS-1 cells were transfected as indicated above. Two days post-transfection, the cells were labelled for 10 min. at 37° C. with 50 µCi [$^{35}$S]-methionine/ml in methionine-free DMEM (Pulse). Cell layers were then washed two times and incubated in DMEM+10% FCS for the indicated time periods (Chase). At each time point of the chase, cell lysates prepared in TNTE lysis buffer (50 mM TRIS/HCL, pH 7.4, 150 mM NaCl, 0.5% TRITON X-100 and 1 mM EDTA) containing protease and phosphatase inhibitors were subjected to immunoprecipitations using an anti-Smad1 polyclonal antibody. Immune complexes were resolved by SDS-PAGE and visualized by autoradiography. A phosphorimager (Molecular Dynamics) was used to quantitate the amount of metabolically labelled Smad1 present at each time point.

Ubiquitination Assay. 293 T cells were transfected with HA-tagged ubiquitin, untagged-Smad1, and either FLAG-hSmurf1 or FLAG-hSmurf1 (C710A) as indicated above. Two days post-transfection, cells were lysed and subjected to a Smad1 immunoprecipitation. The immunoprecipitates were then washed sequentially two times each in TNTE+ 0.1% TRITON X-100, SDS-RIPA (TNTE lysis buffer, 0.1% sodium dodecyl sulfate and 1% deoxycholate), and 500 mM LiCl, 50 mM TRIS/HCL, pH 7.4 and 0.1% TRITON X-100. The presence of HA-ubiquitinated Smad1 in the immune complexes was visualized by SDS-PAGE followed by immunoblotting with the monoclonal anti-HA 12CA5. Protein levels of untagged Smad1, FLAG-hSmurf1 and FLAG-hSmurf1 (C710A) were analyzed by immunoblotting aliquots of total cell lysates with the appropriate antibodies.

Results

Isolation of an E3 ubiquitin ligase that interacts with the BMP signal transducer Smad1. To isolate factors that interact with and potentially regulate Smad1 we performed a yeast two hybrid screen using *Xenopus* Smad1 as the bait protein. Several overlapping cDNAs were isolated that encoded a protein with significant homology to the Hect subclass of E3 ubiquitin ligases (22). This novel gene and a closely related human homolog, Smurf1 and hSmurf1, respectively (for Smad ubiquitination regulatory factor-1), are proteins of 731 amino acids in length, share 91% sequence identity and contain a Hect ubiquitin-ligase domain in the C-terminal portion of the molecule. This domain is characteristic of a specific class of E3 ubiquitin ligases (22) that include in mammals, E6-AP and Nedd4 and in yeast, RSP5p and Pub1 (23-26).

Identification of human Smurf1 genomic location. The human Smurf1 genomic clone is located in PAC clone DJ0808A01, from chromosomal region 7q21.1-q31.1, located from nucleotides 2669 . . . 53763. A computer prediction of intron/exon splicing products generated a single conceptual mRNA with open reading frame directly corresponding to the actual cloned human cDNA.

E3 ubiquitin ligases function together with E1 and E2 enzymes to conjugate ubiquitin to specific protein substrates, which targets the protein for subsequent degradation by the proteasome (12). E1 enzymes recruit and activate ubiquitin, which is then transferred to E2, a ubiquitin conjugating enzyme. The E2 in turn attaches ubiquitin either directly to the protein to be modified, or transfers ubiquitin to the E3 ubiquitin ligase, which confers substrate selectivity to the ubiquitination complex. By functioning to recruit specific target proteins to the conjugation machinery, E3 activity provides selectivity to the ubiquitination process. E3 activity can be provided by structurally and functionally diverse proteins. For instance, E3s may exist as multimeric protein complexes that facilitate substrate recognition, but may or may not possess direct ligase activity. Examples of this include the N-end rule E3s, and the Skp1/Cullin/F-box (SCF) complexes (27-29). In the case of the Hect family of E3 ubiquitin ligases, of which Smurf1 is a member, a single protein provides both substrate specificity and catalytic activity (22, 30).

Figure 1B:
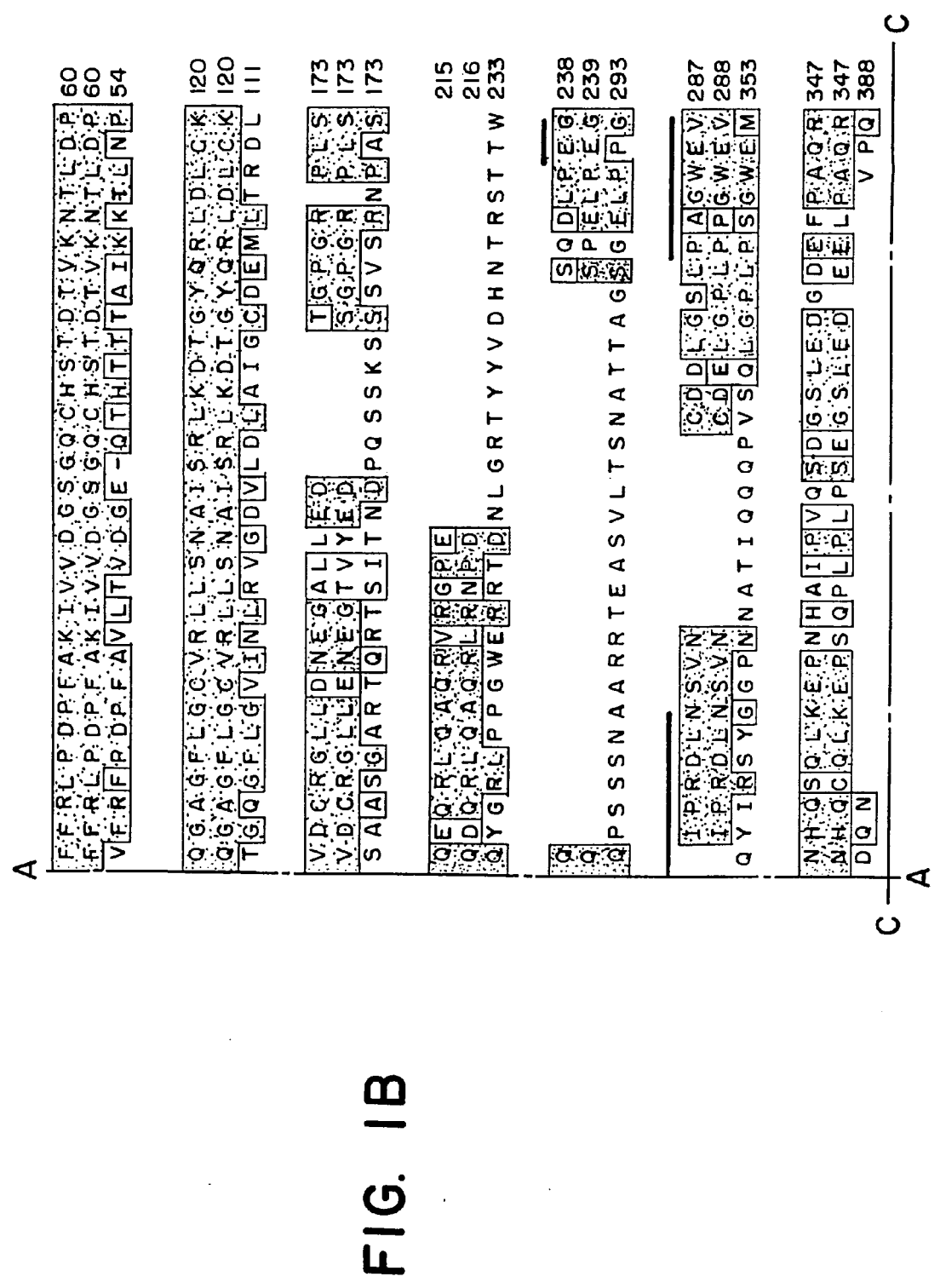

Smurf1 also displays several other structural features characteristic of RSP5, Nedd4 and Pub1 ubiquitin ligases. This includes an amino-terminal phospholipid and calcium binding C2 domain, as well as two WW domains, which facilitate protein-protein interactions by binding to PPXY motifs on partner proteins (31-33). Overall, Smurf1 is most closely related to Pub1 (FIG. 1), a ubiquitin ligase from *Sacromyces pombe* that regulates mitosis by targeting cdc25 for proteosomal degradation (23).

Figure 2B:

Expression of mSmurf1 in embryonic and adult tissue. Northern blots of mSmurf1 showed that a transcript of about 6 kb was the predominant form of Smurf1 expressed in embryos (FIG. 2A). In tissues, major transcripts of 3.0 and 6.0 kb were observed (FIG. 2B). Cytoskeletal actin expression was assayed on the same blot and verified that mRNA loading was equal in all lanes. In the mouse, mSmurf1 was present in very early development, from at least embryonic day 7 onward. In adults, mSmurf1 was expressed in most tissues assayed, but there were differences in the abundance of the transcripts. We did not observe detectable mSmurf1 transcripts in the skeletal muscle, and the kidney and spleen expressed low levels of the large transcript. The small transcript was very abundant in the testes, and it was very weakly or not at all expressed in the kidney, lung, spleen, brain and heart. Both blots were prepared by loading equal amounts of polyA+ RNA in each lane, but to account for any variation in RNA loading and transfer, we probed the blot with a tubulin probe, and found no substantial differences among lanes. Thus, the variation seen in the blots reflected the relative expression of mSmurf1 in embryos and tissues.

Whole-mount in situ hybridization on mouse embryos revealed Smurf1 expression in the nervous system, eye, branchial arches, axial mesoderm (notochord), somites, and limb buds from days p.c. 10-14.

Localization of *Xenopus* Smurf1 to the egg animal pole and embryonic ectoderm. In *Xenopus* embryonic development, Smurf1 mRNA was found expressed from egg through swimming tadpole stages, with maximum levels observed early in development at egg, blastula, and gastrula stages. Smurf1 levels declined sharply near the end of gastrulation, yet zygotic expression persisted at a reduced level into late swimming tadpole stages (FIG. 3A). Whole mount in situ hybridization (FIG. 3B) revealed that maternal Smurf1 transcripts were localized to the animal pole half of eggs and cleaving blastulae, which was confirmed by a northern blot analysis on RNA isolated from animal and vegetal halves of middle blastula stage embryos (not shown). At gastrulation, Smurf1 expression became more widespread in the embryo, coincidentally with the decline in its transcript levels observed by RT-PCR. During neural plate closure, however, Smurf1 expression was localized to the developing nervous system, and by tadpole stages it was highly expressed in the central nervous system, eye, pharyngeal pouches and somites. The embryonic expression pattern of Smurf1 partially overlaps with the expression of Smad1 and BMP-4 in the ectoderm at blastula and gastrula stages and the nervous system, eye, somites and pharyngeal pouches at tadpole stages (34-36).

Expression of hSmurf1 leads to selective reduction in the steady-state protein level of Smad1 and Smad5 in mammalian cells. Smurf1 contains a putative E3 ligase or Hect domain, and therefore was a candidate protein for interacting with Smad1. To investigate whether Smurf1 regulates steady-state levels of Smad1 protein, two mammalian cell lines, 293T and COS-1, were transfected with Smad1 alone or with increasing amounts of Flag-hSmurf1. The steady-state levels of Smad1 protein were then evaluated by immunoblots of whole cell lysates. Smad1 was readily detectable in the absence of hSmurf1 (FIG. 4A). However, expression of hSmurf1, even at low levels not readily detectable by Western blotting, produced a significant, dose-dependent decrease in Smad1 protein levels. At the highest levels of hSmurf1 expression there was no detectable Smad1 protein. Furthermore, co-expression of a constitutively activated form of the BMP type I receptor ALK6, which phosphorylates Smad1 (37, 38), did not alter hSmurf1-dependent decreases in Smad1 levels (FIG. 4B). Thus, expression of hSmurf1 causes dose-dependent decreases in steady-state levels of Smad1. This type of action can occur independently of activation of Smad1 by the type I BMP receptor.

To investigate whether Smurf1 activity is exclusive to Smad1, we investigated its effects on Smad2, a receptor regulated Smad that functions in TGFβ and activin signaling pathways. Unlike Smad1, which was sensitive to the lowest doses of hSmurf1, there was only a slight effect on steady-state levels of Smad2 protein, which occurred only at the highest levels of FLAG-hSmurf1 expression (FIG. 4C). Other Smads were tested, and FLAG-hSmurf1 had little or no effect on Smad3 or Smad4 protein levels, but it elicited a strong decrease in Smad5 protein, which is closely related to Smad 1 (FIG. 4D). Together these data demonstrate that hSmurf1 preferentially regulates the steady-state levels of Smad1 and Smad5, two receptor-regulated Smads that function in BMP signaling.

hSmurf1 regulates Smad1 degradation and ubiquitination. The inclusion of a putative E3 ligase or Hect domain supported the prediction that Smurf1 functions as an E3 ubiquitin ligase. To investigate whether Smurf1 regulates Smad degradation, studies focused on Smad1 (91% homology with Smad5). Analysis of Smad1 turnover by pulse-chase experiments revealed that in the absence of hSmurf1, Smad1 had a half life of approximately 6 hours. However, in the presence of hSmurf1, Smad1 turnover was significantly enhanced (half life of less than 2 hours) (FIG. 5A). Thus, hSmurf1 increases the rate of Smad1 turnover.

To determine the mechanism of hSmurf1-mediated turnover of Smad1, Smad1 ubiquitination in intact cells was assessed. To facilitate detection of ubiquitin, 293T cells were transfected with HA-tagged ubiquitin together with Smad1, in the presence or absence of FLAG-Smurf-1. In the absence of hSmurf1, Smad1 displayed little of no detectable ubiquitination. However, upon co-transfection with hSmurf1 we observed the appearance of a ladder of ubiquitin-conjugated Smad1 (FIG. 5B). To confirm that ubiquitination of Smad1 required the catalytic activity of the Hect domain in hSmurf1, a point mutant in hSmurf1 (hSmurf1 (C710A)) was constructed. This residue is critical for the catalytic activity of the Hect domain and the mutation is thought to target the cysteine residue that forms a thiolester bond with ubiquitin (22). In contrast to wildtype hSmurf1, expression of hSmurf1 (C710A) did not yield ubiquitinated Smad1. Moreover, hSmurf1 (C710A) did not affect Smad1 steady-state protein levels compared to wildtype hSurf1, despite efficient expression of the mutant protein (FIG. 5C). Together, these data suggest that hSmurf1 alters Smad steady-state levels by inducing ubiquitin-mediated degradation of Smad1 via its Hect domain.

Smurf1 interacts selectively in vivo with Smad1 and Smad5. The interaction of Smurf1 with Smad proteins was investigated to assess the basis for the selective targeting of Smad1 and 5 for degradation by Smurf1. The yeast 2-hybrid assay was first used to test the ability of *Xenopus* Smurf1 to interact with Smad1, Smad4 or the non-specific control protein nuclear lamin. Yeast co-transfected with Smurf1 and Smad1 exhibited significant β-galactosidase activity; yeast co-transfected with Smurf1 and either Smad4 or lamin did not demonstrate β-galactosidase activity (FIG. 6A, left). Smurf1 selectively bound to Smad1, but not to Smad2 or Smad4 (FIG. 6A, right) as demonstrated by the capacity of $^{35}$S-labelled Smurf1 to bind and immunoprecipitate Smads in vitro.

To test the capacity of $^{35}$S-labelled Smurf1 to bind and immunoprecipitate Smads in vitro, and to test the specificity of Smurf1-Smad interactions in intact cells, the association of hSmurf1 with various Smads in 293T cells was investigated. Wild type hSmurf1 did not detect interactions with Smad1. However, it is possible that in intact cells Smurf1-

Smad1 interactions are transient in nature, since demonstrating association between ubiquitin ligases and their substrates has proven difficult in other systems. Be examining Smad1 interaction with the ubiquitin-ligase mutant FLAG-hSmurf1 (C710A), association of the proteins could be detected (FIGS. 6B and 6C). Furthermore, this interaction was unaffected by coexpresssion of the constitutively active BMP-type I receptor, ALK2 (data not shown), and is consistent with the notion that hSmurf1 regulates Smad1 turnover independent of BMP signaling. hSmurf1 (C710A) also bound efficiently to Smad5, but analysis of association with Smad2 revealed little, if any, interaction (FIGS. 6A and 6B).

The linker regions of R-Smads contain a PPXY sequence, which is a conserved motif recognized by WW domains such as those found in Smurf1. Unlike wild type Smad1, a mutant of Smad1, in which the PY motif was deleted, associated only weakly with Smurf1 and was resistant to Smurf1-mediated degradation (data not shown). These results show that hSmurf1 associates specifically with Smad1 and Smad5, which interaction is mediated by binding between the PY motif in Smad1 and the WW domains of Smurf1.

The specificity of hSmurf1 as a ubiquitin ligase in targeting the Smads, was further tested by comparing it to Nedd4, a structurally related ubiquitin ligase. While Smad1 co-precipitated efficiently with hSmurf1 (C710A), it did not interact with the corresponding Nedd4 mutant. Consistent with this, overexpression of Nedd4 did not affect the steady-state level of Smad1 protein (FIG. 6C, lower panel). Together, these data indicate that both human and *Xenopus* Smurf1 proteins associate selectively with BMP-regulated Smad1 and Smad5, and that this interaction is specific to Smurf1 rather than a general feature of the Hect class of ubiquitin ligases.

Smurf1 antagonizes endogenous BMP signals in *Xenopus* embryos to dorsalize ventral mesoderm and neuralize ectoderm. In the *Xenopus* blastula, Smurf1 expression is localized to the animal pole ectoderm and partly overlaps the marginal zone, i.e., a belt of cells located at the equator of the blastula which forms the mesoderm. This pattern of expression, considered together with the ability of Smurf1 to interact with, ubiquitinate, and degrade BMP pathway-specific Smads, suggests that Smurf1 may function in ectodermal and mesodermal patterning by antagonizing BMP signals through Smad1 or Smad5.

Presently, naturally-occurring inhibitors of TGFβ activities have been described at the ligand level. Those factors, which include chordin, follistatin and noggin, act outside of cells by binding particular ligands, including BMPs and activin. During *Xenopus* mesoderm induction and patterning, BMP signals in the ventral part of the marginal zone specify development of tissues, such as blood and mesenchyme, that are characteristic of the ventral region of the tadpole. However, if BMP signaling is blocked by ligand antagonists such as chordin, follistatin, or noggin (which are secreted by the dorsal Spemann organizer), or by artificial inhibitors such as dominant negative BMP ligands or receptors, the prospective ventral mesoderm will differentiate into dorsal tissues such as muscle and notochord (a process referred to as "dorsalization") (5, 39).

Smurf1 has the potential to regulate BMP signals in the marginal zone, so ectopic Smurf1 expression was tested for interference with ventral tissue patterning. Smurf1 mRNA was microinjected into 4 cell blastula stage embryos in the ventral marginal zone (VMZ) to trigger the formation of ectopic secondary axial structures in the ventral region of 52% of tadpoles (n=25). These secondary axial structures induced by Smurf1 were characteristic of dorsalization caused by BMP inhibition. Their formation was rescued by co-expression of Smad1 together with Smurf1, demonstrating that the effect of Smurf1 was limited to interference with the BMP/Smad1 pathway (FIG. 7A). Furthermore, overexpression of Smurf1 in cells of the dorsal marginal zone (DMZ), which forms head and dorsal axial structures, had no effect (data not shown). This latter observation was consistent with previous findings of the invention that Smurf1 does not target Smad2 in cultured cells.

The dorsalizing effects of Smurf1 using VMZ explants was further characterized. In this case, Smurf1 expression caused reduced blood differentiation and concomitant muscle differentiation, consistent with the dorsalizing effect of Smurf1 (FIG. 7A, right panel). As in the axis formation assay, co-expression of Smad1 with Smurf1 reversed these dorsalizing effects and demonstrated BMP pathway specificity.

In the ectodermal germ layer, endogenous BMP expression specifies epidermis, but when BMP signals are reduced or eliminated the ectoderm differentiates into cement gland or neural tissue, respectively (40, 41). The localization of Smurf1 mRNA in the ectoderm of the *Xenopus* blastula and early gastrula suggested that Smurf1 may regulate ectodermal patterning by modulating BMP signaling. Therefore, Smurf1 was tested for its presence in ectodermal tissue. It was found that overexpression of Smurf1 in animal caps triggers neural and cement gland differentiation, which is characteristic of a reduction in BMP signaling. These effects were reversed by co-expression of Smad1 in the animal cap (FIG. 7B). Together these results demonstrate that Smurf1 can block BMP signals in the ectoderm and mesoderm, suggesting that Smurf1 decreases BMP signaling in these tissues to affect embryonic patterning.

Smurf1 inhibits Smad1 activity but potentiates Smad2 activity in embryonic cells. In cultured cells, Smurf1 triggers ubiquitination and degradation of BMP pathway-specific Smads, and in *Xenopus* embryos Smurf1 antagonizes endogenous BMP signals. In *Xenopus* animal caps overexpression of Smads mimics the effects of TGFβ factors that signal through specific R-Smads. Thus, Smad1 induces exclusively ventral/posterior mesoderm, like BMP ligands, while Smad2 induces dorsal (Spemann organizer) mesoderm, like activin, Vg1 and nodal. We therefore tested whether Smurf1 can directly antagonize the mesoderm induction activities of Smad1 or Smad2 by overexpressing each Smad together with various doses of Smurf1 in animal caps. We found that expression of Smad1 alone (1 ng mRNA) induced ventral mesoderm, as demonstrated by expression of the ventral/posterior mesodermal markers Xhox3 and Xcad1. However, co-expression of Smurf1 and Smad1 blocked induction of these markers at all Smurf1 doses tested (FIG. 8A), demonstrating that Smurf1 can antagonize Smad1 activity.

To determine whether Smurf1 can interfere with Smad2, a dose of Smad2 (50 pg mRNA) was used in an amount sufficient to induce myoD (a vertebrate muscle marker of dorsal/lateral mesoderm), but insufficient to induce goosecoid (a frog marker for dorsal mesoderm of the Spemann Organizer) (FIGS. 7B, C). When Smurf1 was co-expressed with Smad2 there was no inhibition of myoD induction at any of the Smurf1 doses tested (FIG. 8B). This was consistent with other findings that Smurf1 does not target Smad2. Interestingly, as the dose of Smurf1 was increased in the presence of this limiting amount (50 pg) of Smad2, induction of goosecoid gene expression was observed. This induction was dependent on Smad2 expression, since Smurf1 alone did not induce goosecoid. The response of cap cells to increasing amounts of Smurf1 in the presence of limiting Smad2 had similar effects to increasing the dose of Smad2 alone (FIG. 8C). Thus, a combination of 50 pg Smad2 and 100 pg Smurf1 induced goosecoid expression to a level equivalent to a 5-fold higher (250 pg) dose of Smad2 alone (FIG. 8C). Thus, rather than inhibit Smad2 activity, Smurf1 appears to enhance the sensitivity of the animal cap to Smad2. These experiments demonstrate that in addition to blocking the response of animal pole cells to the BMP pathway, Smurf1 enhances these cells' response to the activin pathway. Although the invention is not dependent on any particular mechanism, the inventors propose that the Smurf1-mediated shift in responsiveness of animal pole cell results from lowered endogenous BMP signaling caused by targeted ubiquitination of the Smurf1 substrates, Smads 1 and 5. Therefore, Smurf1 functions during development to alter the competence of cells to respond to multiple TGFβ ligands by selective inactivation of a particular Smad pathway.

Discussion

The findings of the inventors provide a clear role, pathway and mechanism for selective ubiquitination in regulating developmental patterning. The Example presented evidence that TGFβ signaling can be controlled by ubiquitination of Smad signal transduction molecules, and that this activity has developmental consequences. Specifically, it was shown that Smurf1, a Hect family E3 ubiquitin ligase, selectively and directly interacts with BMP pathway-specific Smads, Smad1 and Smad5, triggering their ubiquitination and degradation. Smurf1 does not, however, interact with or affect TGFβ/activin pathway-specific Smad2, nor the common partner in Smad signal transduction complexes, Smad4. Furthermore, targeting of Smads by Hect ubiquitin ligases is not a general characteristic of E3 ligases since Nedd4 does not interact with Smads. Interestingly, the results showed Smurf1-mediated turnover of Smads is not affected by BMP signaling, suggesting that activated forms of Smad1 or Smad5 are not required to serve as Smurf1 substrates. Thus, Smurf1 does not act downstream of activated Smads to turn off BMP signals, but rather controls the competence of cells to respond to BMPs by regulating the steady state level of Smad protein in the cell.

The mSmurf1 gene is expressed in early development, where we predict it will regulate the response of cells to BMP signals. Smurf1 is present in adult tissues implying mSmurf1 regulates late stage BMP signals. Perhaps these signals act in tissue stasis, or perhaps ongoing differentiation associated with growth. To a large degree the expression in developing mouse at neurula stage and thereafter is in good accord with the expression patterns seen in the frog embryo at similar stages.

The phenotypic effects of Smurf1 in Xenopus embryos point to selective ubiquitination as an important regulator of inductive signals during embryonic development. Smurf1 dorsalizes mesoderm and neuralizes ectoderm by interfering with BMP signals that control patterning of these germ layers in normal development. Presently, regulation of BMP-dependent patterning is considered to be accomplished by secreted BMP-binding proteins, such as chordin, noggin and follistatin, which inhibit BMP signals extracellularly by direct binding to BMP ligands. However, Smurf1 provides a new mechanism to regulate BMP signals, which acts at the level of signal transduction, and presumably functions cell autonomously because Smurf1 is an intracellular protein. Furthermore, unlike secreted BMP binding proteins, which have restricted ligand specificity, Smurf1 provides broad inhibitory activity for BMP pathways because many type I receptors (ALK1, ALK2, ALK3, and ALK6) signal through Smad1 and Smad5 (42). Thus, in the developing embryo Smurf1 cooperates with extracellular BMP inhibitors to specify pattern formation. Whether Smurf1 is regulated in some manner remains an open question.

Of particular interest is the localization of Smurf1 mRNA to the animal pole of the Xenopus egg and blastula. This region forms ectodermal tissues such as epidermis, cement gland and the nervous system, tissue fates which are controlled by the level of BMP signaling perceived by the cells. When animal pole ectoderm is deprived of endogenous BMP signals neural differentiation occurs spontaneously, but as the levels of BMP ligand applied to cells, or the amount of Smad1 expressed within cells, are gradually increased, a spectrum of cell fates are progressively specified from neuronal, through cement glad then epidermis. Furthermore, reduced BMP signaling in the prospective ventral mesoderm of Xenopus embryos causes that tissue to be re-specified as dorsal mesoderm. Since Smurf1 can regulate cell responsiveness to BMP signals it may function in both ectodermal and mesodermal fate specificity by controlling the level of Smad1 or Smad5. High Smurf1 levels may completely shut off the ability of a cell to respond to BMPs, but at intermediate or low levels Smurf1 may modulate the magnitude of the BMP signal through the control of Smad1 protein levels to alter the nature of the cellular response. Consequently, Smurf1 may control cell fate determination in response to BMPs by establishing an intracellular morphogenetic gradient of Smad1 activity. In a variety of animals maternal mRNAs localized in eggs function as determinants of cell fate (43). In Xenopus, mRNAs encoding Vg1 (a TGFβ member) and Brat/VgT are localized to the egg vegetal pole where they specify endoderm and mesoderm (44, 45). The results presented in this Example suggest that localized Smurf1 in the egg animal pole may function as a determinant of ectodermal cell fate.

An intriguing consequence of Smurf1 overexpression in Xenopus animal caps is altered cell competence to respond to Smad2, the activin/TGFβ pathway specific Smad. Smurf1 enhances the sensitivity of cells to a fixed level of ectopically expressed Smad2, so as Smurf1 levels increase, the mesoderm that is induced becomes progressively more characteristic of the Spemann organizer, the most dorsal type of mesoderm. This response mimics the effects of what happens when the levels of Smad2 alone are elevated in animal caps. Thus, Smurf1 can simultaneously change the competence of cells to respond to different TGFβ signals: it inhibits responses to the Smad1 pathway while stimulating responses to the Smad2 pathway. The distinct effects of Smurf1 on different TGFβ signaling pathways has important consequences for embryonic development, cell growth, tissue stasis and other biological functions regulated by the TGFβ superfamily.

Example 2

Characterization and Cloning of Human Smurf2

Human Smurf2 was identified and cloned using a Xenopus Smurf1 sequence in an EST database. Two overlapping EST clones corresponding to hSmurf2 were obtained and used to construct a full length sequence for hSmurf2. Smurf2 is closely related to Smurf1, displaying approximately 75% homology to the amino acid sequence of hSmurf1. Smurf2 contains a C2 domain at the amino-terminus, followed by three WW domains and a HECT ubiquitin ligase domain (FIG. 12). Smurf2 is closely related to Smurf1, but possesses an exra WW domain downstream of the C2 domain (FIG. 13). Smurf2 was found to be expressed throughout early development and was present in most adult tissues, with lower levels in spleen and skeletal muscle (FIGS. 14A and 14B). RT-PCR analysis further revealed that Smurf2 is expressed in a variety of cell lines that include P19, HepG2 and 293T.

Isolation of Human and mouse Smurf2. Several overlapping human clones displaying similarity to Smurf1 were identified from the expressed sequence tag (EST) database and a full-length version of Smurf2 was constructed by PCR using two overlapping EST clones. For northern blot analysis, a partial mouse Smurf2 cDNA clone encoding 225 amino acids of open reading frame including the stop codon and displaying 96% amino acid identity to human Smurf2 was identified in the EST database (I.M.A.G.E. clone ID 638876).

Construction of Plasmids. For mammalian expression constructs of Smurf2, the open reading frame was amplified by polymerase chain reaction (PCR) and was subcloned into pCMV5 in frame with an amino-terminal Flag or Myc tag (69). For Smurf2 WW domain deletions, amino acids 163-185 for DWW1, 257-279 for DWW2, and 303-325 for DWW3 were deleted. To generate the catalytically-inactive ubiquitin-ligase mutant of Smurf2, cysteine 716 was replaced with alanine. To generate the Smad7 PY mutants, tyrosine 211 was replaced with alanine (Y211A) or the PPPPY sequence between amino acid residues 206-212 was deleted (ΔPY). For TβRI-Flag, a Flag tag was introduced at the carboxy terminus of the receptor. All constructs were generated by PCR and confirmed by sequencing. The bacterial expression vectors, pET15-Smad7-HA and pGEX4T-1-Smurf2, were generated using convenient restriction sites.

Immunoprecipitation, Immunoblotting, and Affinity-labelling. For studies in mammalian cells, 293T and COS-1 cells were transiently transfected using calcium phosphate precipitation, or the DEAE-dextran method, respectively. Immunoprecipitation and immunoblotting were carried out using anti-HA monoclonal (12CA5, Boehringer), anti-HA rabbit polyclonal (Santa Cruz), anti Myc monoclonal (9E10 ascites, Developmental Studies Hybridoma Bank), anti-FLAG M2 monoclonal (Sigma) or anti-Smad7 rabbit polyclonal antibodies. For anti-Smad7 antibodies, rabbits were immunized with bacterially-produced GST-Smad7 encoding amino acids 202-260. After absorption of the antibody to either protein G or A-Sepharose, the precipitates were washed five times with TNTE 0.1% (50 mM TRIS, pH 7.4, 150 mM NaCl, 1 mM EDTA, 0.1% TRITON X-100), separated by SDS-PAGE, transferred to nitrocellulose and immunoblotted with the appropriate antibody. Detection was conducted using the appropriate horseradish peroxidase (HRP)-conjugated sheep anti-mouse or anti-rabbit secondary antibodies and enhanced chemiluminescence (Amersham). Bacterially-produced His-Smad7-HA was incubated with either $Ni^{2+}$-NTA beads (Qiagen) or with GST or GST-Smurf2-bound glutathione beads (Amersham), washed three times with TNTE (0.5% TRITON X-100) and precipitates were analyzed by immunoblotting with anti-HA antibodies. For affinity-labelling, transfected COS-1 cells were incubated with 250 pM [$^{125}$I]TGF-b1 at 4° C. for 1 h, and receptors were cross-linked to ligand with DSS as described (70). The amount of TβR1 bound to Smurf2 or Smad7 was quantified by phosphoroimaging (Molecular Dynamics).

Pulse-chase analysis and ubiquitination assay. COS-1 cells were transfected with the indicated constructs and two days post-transfection the cells were labelled for 15 min at 37° C. with 50 mCi/ml [$^{35}$S]-methionine (Trans [$^{35}$S]-label; FIG. 2B) or 150 mCi/ml [$^{35}$S]-methionine (FIGS. 5C and D) in methionine-free Dulbecco's Modified Eagle's Medium (DMEM). Cell layers were then washed two times and incubated in DMEM containing 10% fetal bovine serum in the presence or absence of 30 mM lactacystin (obtained from E. J. Corey, Harvard University) or 0.4 mM chloroquine for the indicated times. At each time point, cell lysates were immunoprecipitated with anti-HA monoclonal antibodies, resolved by SDS-PAGE and visualized by autoradiography. Metabolically-labelled proteins were quantified by phosphorimaging. For the ubiquitination assay, 293T cells were transfected with HA-tagged ubiquitin and combinations of receptors, Smad7 and Smurf2. Cell lysates were subjected to anti-Smad7 immunoprecipitation and immunoprecipitates were boiled in 1% SDS for 5 min, diluted with TNTE 0.1% and reprecipitated with anti-Smad7 antibodies before anti-HA immunoblotting.

Subcellular localization by Immunofluorescence Deconvolution Microscopy. Mv1Lu cells, plated on gelatin-coated PERMANOX CHAMBER SLIDES (Nunc), were transfected with the indicated constructs by the calcium phosphate precipitation method. The cells were fixed, permeabilized, and reacted with the primary and secondary antibodies as described (69). Images were obtained using the OLYMPUS 1×70 inverted microscope equipped with fluorescence optics and DELTAVISION deconvolution microscopy software (Applied Precision).

Transcriptional Response Assay. HepG2 cells were transiently transfected using the calcium phosphate DNA precipitation method with CMV-βgal, 3TP-Lux reporter construct and Smad7-HA constructs as indicated. Total DNA was kept constant by the addition of pCMV5 empty vector. The next day, cells were incubated overnight with or without 100 μM TGFβ. Luciferase activity was measured using the luciferase assay system (Promega) in a BERTHOLD LUMAT LB 96V luminometer and was normalized to β-galactosidase activity.

Results

Figure 15D:
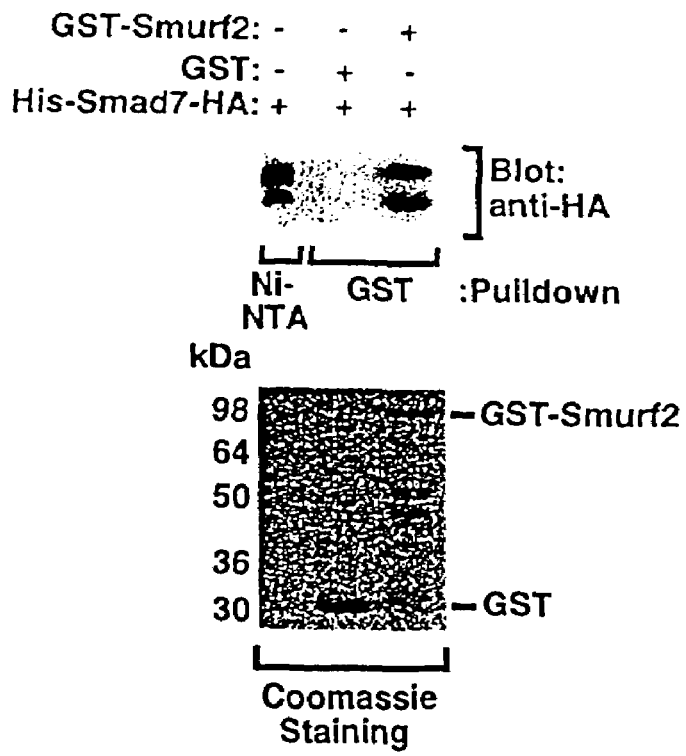
Figure 15C:
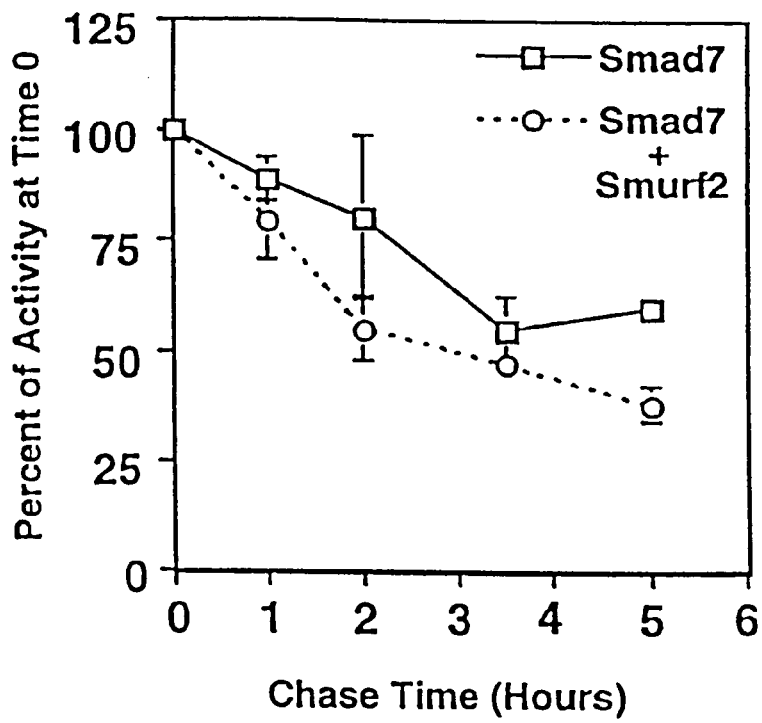

Smurf2 does not regulate Smad steady-state levels. Smads were expressed in 293T cells in the absence or presence of Smurf2. Surprisingly, unlike Smurf1 which targets Smad1 for ubiquitin-mediated proteolysis, Smurf2 expression did not alter the steady-state levels of Smads 1, 2, 4 or 7 (FIG. 15A). To determine whether Smurf2 might associate with any of these Smads, the cell lysates were subjected to anti-Smurf2 immunoprecipitation and associated Smads examined by immunoblotting. In cells coexpressing Smad1, 2, or 4, no Smads were found to coprecipitate with Smurf2 under these conditions (FIG. 15B). In contrast, in cells expressing Smad7, a strong interaction between Smurf2 and Smad7 was detected. To confirm that Smurf2 expression did not alter Smad7 turnover, we also performed pulse-chase analysis of Smad7. Smad7 expressed in the absence or presence of Smurf2 displayed a similar half-life of approximately 4 h (FIG. 15C). To characterize the Smad7-Smurf2 association, GST-Smurf2 fusion protein was purified from bacteria and incubated with bacterially produced Smad7. Under these in vitro conditions Smad7 bound efficiently to Smurf2, indicating that Smurf2 associates directly with Smad7 (FIG. 15D). We also analyzed the determinants on Smad7 and Smurf2 that mediate their interaction. Smad7 possesses a PPXY sequence (PY motif) in its linker region, which can mediate interaction with WW domains such as those found in Smurf2 (71). The Smad7 PY motif was altered by changing the tyrosine residue to alanine (Smad7 (Y211A)) or by deleting the entire motif (Smad7(ΔPY)). Analysis in 293T cells of Smurf2 binding to either Smad7 mutant revealed that the interaction with Smurf2 was reduced but not entirely abolished (FIG. 15E). This suggests that the PY motif makes an important contribution to the Smad7-Smurf2 interaction, however, it is not the sole determinant, and other regions in Smad7 may also contribute to their association. We also made mutants of Smurf2 in which each of the three WW domains were deleted. The interaction of Smad7 with a Smurf2 mutant that lacked the first WW domain was comparable to wild type Smurf2, however deletion of either WW2 or WW3 abolished any detectable interaction with Smad7 (FIG. 15F). Thus, the WW2 and WW3 domains in Smurf2 are both required to mediate binding to Smad7. Together, these results show that Smurf2 binds directly to Smad7 via its WW2 and WW3 domains but that it does not target Smad7 for ubiquitin-mediated proteolysis in the absence of TGFβ signalling.

Smad7 recruits Smurf2 into a complex with the TGFβ receptors. Smad7 binds heteromeric complexes of TGFβ type II (TβRII) and type I (TβRI) receptors through interactions with the activated type I receptor subunit (72, 56). The constitutive association between Smad7 and Smurf2 thus raised the interesting possibility that Smad7 might function to recruit Smurf2 to the TGFβ receptor complex. To test this, we expressed TGFβ receptors in COS-1 cells in the presence and absence of Smad7 and Smurf2. Receptors were then labelled by crosslinking to [$^{125}$I]-TGFβ. Affinity-labelled receptor complexes that co-precipitated with Smurf2 were visualized by autoradiography. In the absence or presence of Smad7, little or no TGFβ receptor complexes were found to co-precipitate with wild type Smurf2 (FIG. 16). A Smurf2 catalytic mutant was constructed in Smurf2 in which cysteine 716 was converted to an alanine residue (C716A). This mutation targeted the cysteine residue in the HECT ubiquitin-ligase domain that is thought to form a thiolester bond with ubiquitin. When Smurf2(C716A) was expressed alone we detected a slight interaction with the TGFβ receptors (FIG. 16). However in the presence of Smad7 the interaction of Smurf2(C716A) with the receptors was dramatically enhanced. Thus, Smad7 mediates the interaction of Smurf2 with the TGFβ receptors.

We also examined Smad7 bound to the receptors. Smad7 binds heteromeric TGFβ receptor complexes by interacting with the activated type I receptor subunit (72, 56). In the presence of wild type Smurf2 we observed a strong decrease in the amount of TGFβ receptor complexes that co-precipitated with Smad7 (FIG. 16, lane 3). This correlated with a decrease in the total amount of type I receptor present in these transfectants. Since Smad7 binds to receptor complexes via interactions with the activated type I receptor, these results suggest that Smurf2 decreases the levels of Smad7-bound receptor complexes. Consistent with this notion, when Smad7 was co-expressed with the catalytically inactive mutant of Smurf2, a decrease in Smad7-bound receptor levels was not observed (FIG. 16, lane 5). These results indicate that the catalytic activity of Smurf2 mediates the down-regulation of TGFβ receptors that are bound to Smad7.

Smad7 controls the subcellular localization of Smurf2. Smad7 resides in the nucleus and upon activation of TGFβ signalling is exported into the cytoplasm where it binds to TGFβ receptors through interaction with the receptor I subunit (73). To investigate whether Smad7 recruited Smurf2 to the receptors in intact cells, we determined whether Smad7 might regulate Smurf2 localization. For this, we expressed TβRII, TβRI and Smurf2(C716A) in the absence or presence of Smad7 and examined the subcellular distribution of the appropriate protein by immunofluorescence microscopy.

Smad7 was localized to the nucleus, but in the presence of signalling was found predominantly in the cytoplasm, where it also colocalized with the transiently expressed TGFβ receptors in a punctate pattern. This distribution of TGFβ receptors has been observed previously by us and others (74-76). Smurf2 was similarly found predominantly in the nucleus, but this localization was not altered in the presence of TGFβ signalling. However, when Smad7 was coexpressed, the subcellular distribution of Smurf2 was dramatically altered and the protein was found predominantly outside of the nucleus and was extensively colocalized with the TGFβ receptors. These results suggest that Smad7 expression leads to export of Smurf2 from the nucleus and recruitment of Smurf2 to the TGFβ receptor complex.

Figure 17A:
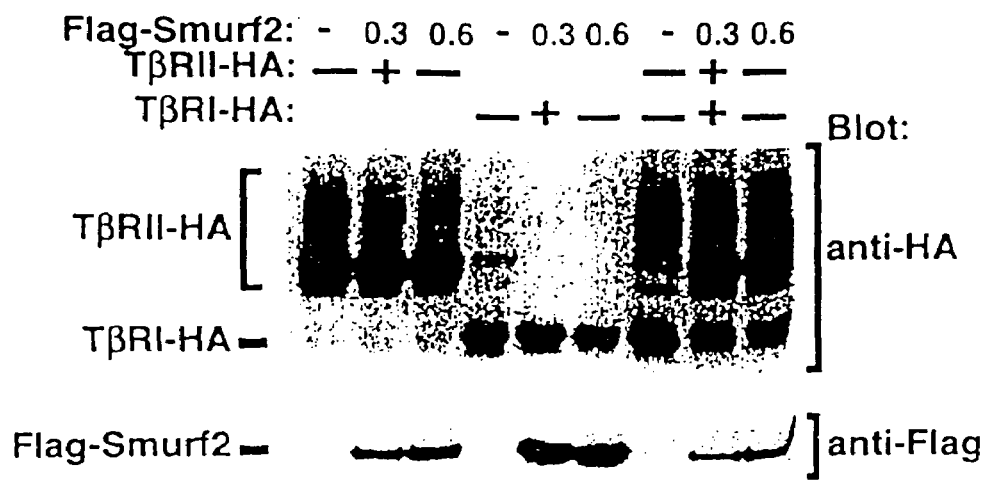
Figure 17B:
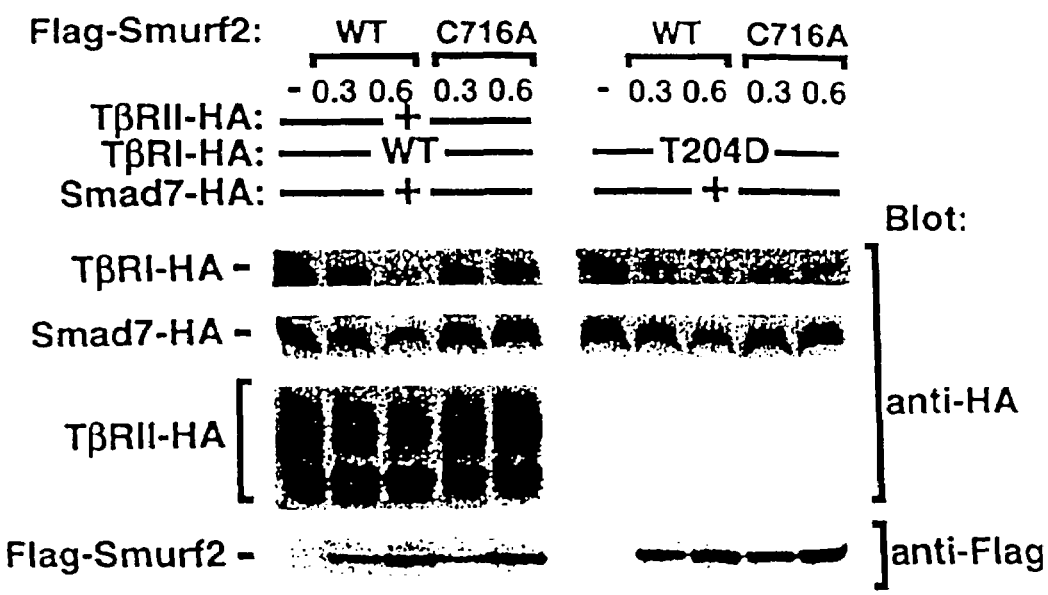
Figure 17C:
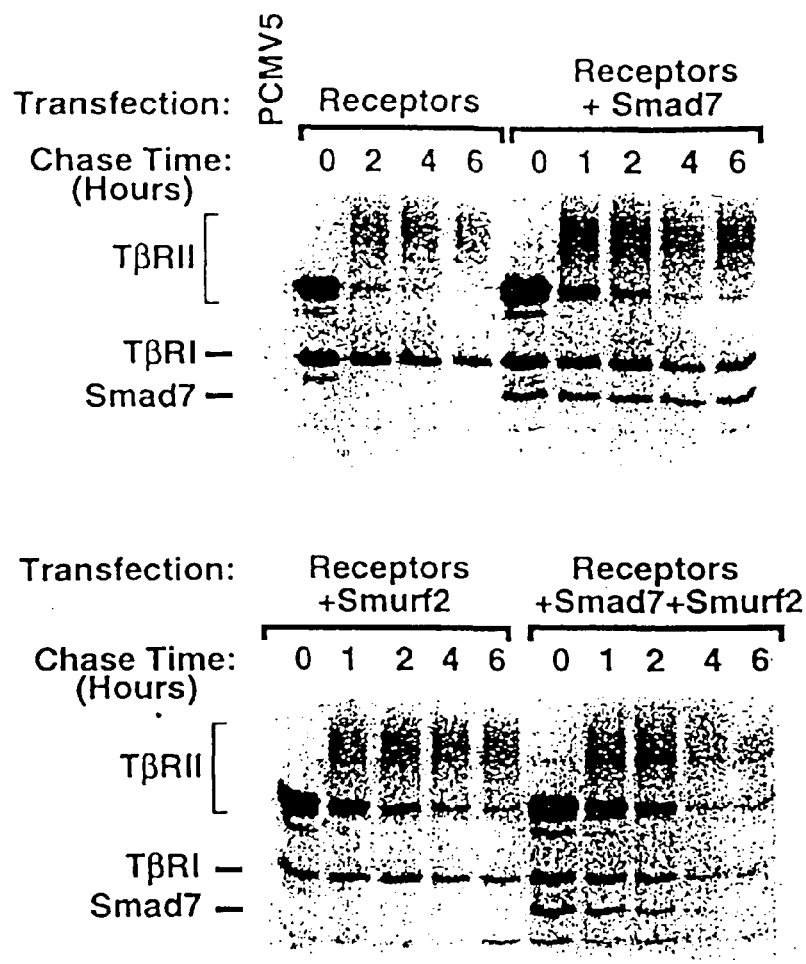

Smurf2 induces degradation of TGFβ receptors and Smad7. The strong decrease in Smad7-associated receptors in the presence of wild type but not mutant Smurf2 suggested the possibility that Smurf2 might catalyze degradation of Smad7-bound receptor complexes. To analyze Smurf2-dependent turnover of TGFβ receptor complexes we coexpressed TβRII and TβRI in 293T cells. Under these conditions TβRII and TβRI assemble efficiently into functional heteromeric complexes, allowing us to investigate the turnover of the entire receptor pool. We first investigated steady-state levels of the receptors in cells expressing Smurf2 (FIG. 17A) and observed that Smurf2 had minimal effects on the steady-state levels of type II or type I receptors when the receptors were expressed either alone or together. However, in the presence of wild type Smad7, increasing Smurf2 expression led to a strong decrease in the steady-state levels of the type I receptor (FIG. 17B). In contrast, Smurf2 (C716A) had no effect. Levels of type II receptor were also decreased upon expression of wild type Smurf2, although to a lesser extent than that observed for the type I receptor. This difference may be due to the fact that Smad7 binds receptor complexes via the activated type I receptor and does not interact with TβRII alone. We also tested whether Smurf2 targets a constitutively active version of the type I receptor, TβRI (T204D). This receptor mediates TGFβ signalling in the absence of the type II receptor and also binds Smad7 (72). Similar to receptor complexes, wild type Smurf2, but not Smurf2(C716A) caused a decrease in the steady-state levels of the activated type I receptor (FIG. 17B). To confirm that changes in receptor steady-state levels reflected alterations in receptor turnover, we analyzed by pulse-chase analysis the half-life of TβRII and TβRI (FIG. 17C). Analysis of the type II receptor revealed that the newly synthesized protein had a half-life of approximately 1 h. In contrast TβRI was considerably more stable and displayed a half-life of approximately 4-6 h. Furthermore, the half-life of the type I receptor was unchanged when either Smad7 or Smurf2 were expressed individually with the receptors. However, when Smurf2 and Smad7 were co-expressed together with the TGFβ receptor complex, the half-life of the type I receptor was decreased to approximately 1 h. Thus, Smad7 and Smurf2 enhance the turnover of the type I receptor.

Ubiquitin-mediated proteolysis of membrane receptors can be mediated by both the proteasome and lysosome (60).

Figure 17D:
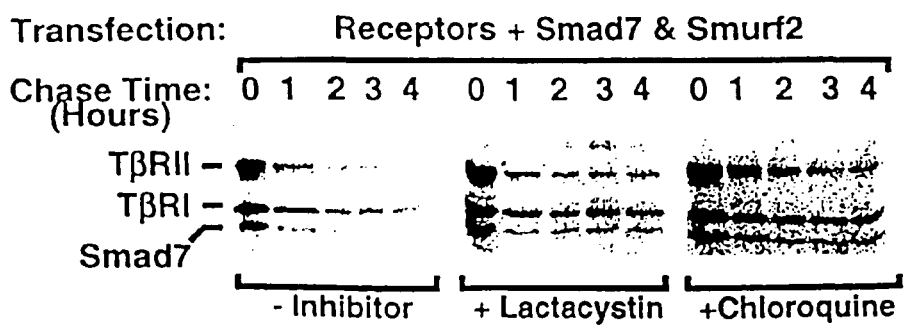

To test whether Smurf2-dependent enhancement of TGFβ receptor degradation was dependent on proteasome and lysosome function we assessed the turnover of receptors in the presence and absence of lactacystin and chloroquine, which inhibit protein degradation by the proteasome and lysosome, respectively. Pulse-chase analysis of receptors revealed that each inhibitor on its own caused stabilization of a subset of the total TGFβ receptor pool (FIG. 17D). These results suggest that both the proteasome and the lysosome contribute to the enhanced turnover of the receptors that is observed in the presence of Smad7 and Smurf2.

In the course of these analyses of the TGFβ receptor we also evaluated Smad7 protein levels. In the absence of TGFβ receptor complexes Smad7 steady-state level and turnover was unaffected by Smurf2 (see FIG. 15). However, in the presence of TGFβ receptor complexes, Smad7 steady-state levels and half-life were decreased by Smurf2 expression (FIGS. 17B and 17C, respectively). Furthermore, this decrease in Smad7 was dependent on the catalytic activity of the Smurf2 HECT domain, since expression of the Smurf2 (C716A) mutant did not alter Smad7 levels. Smad7 turnover was also stabilized by lactacystin and chloroquine, suggesting that like the receptor complex, Smad7 is degraded by both proteasomal and lysosomal pathways. Thus, in the presence of TGFβ signalling Smurf2 induces degradation of Smad7, possibly by targeting the entire receptor-Smad7 complex.

Figure 17E:
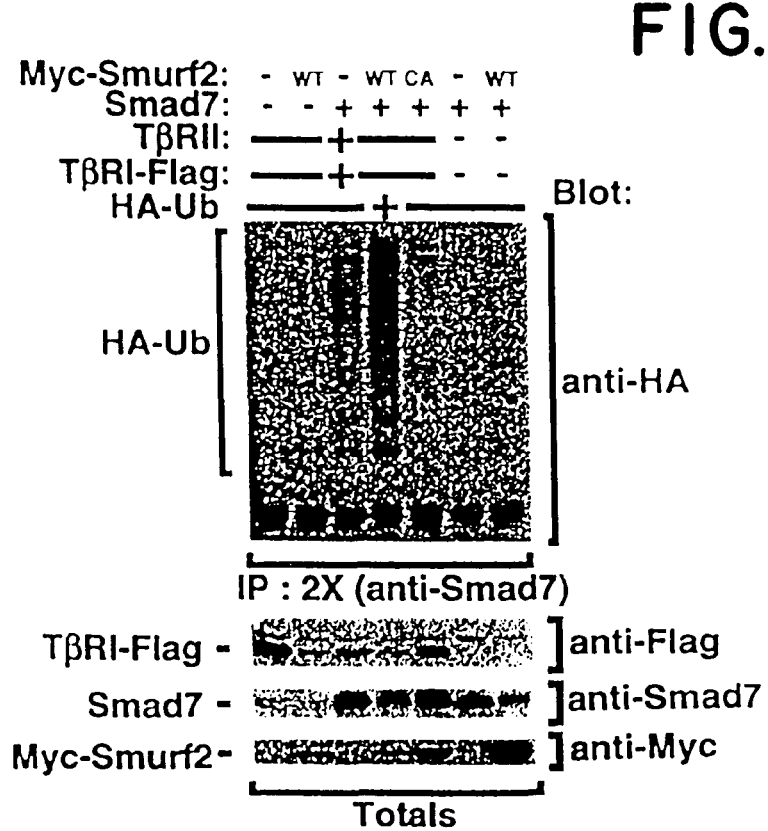

To investigate ubiquitination of the receptors and Smad7, we expressed an HA epitope-tagged version of ubiquitin and evaluated ubiquitin-conjugates of TβRII, TβRI or Smad7 by immunoprecipitation followed by immunoblotting. To ensure specificity, immunoprecipitated samples were boiled in SDS and then reprecipitated with the appropriate antibody prior to immunoblotting. Analysis of Smad7 ubiquitination revealed that in the absence or presence of Smurf2 there was little ubiquitin conjugated to the protein (FIG. 17E). However, when Smurf2 was coexpressed with Smad7 and the TGFβ receptors, we observed high molecular weight ubiquitin conjugates of Smad7 that were not detected when the catalytic mutant of Smurf2 was used. In contrast to Smad7, we were unable to detect significant Smurf2-dependent ubiquitination of the type I receptor. Since receptor turnover is increased in the presence of Smurf2 and Smad7, the inability to detect ubiquitin-conjugated receptors may reflect rapid degradation of the receptors that may occur once they are ubiquitinated. Alternatively, ubiquitination of Smad7 may serve as the signal that targets the entire receptor-Smad7 complex to the proteasome. Together these results show that Smad7-dependent recruitment of Smurf2 to the TGFβ receptor leads to proteasome and lysosome-mediated degradation of TGFβ receptor complexes and Smad7.

Figure 18C:
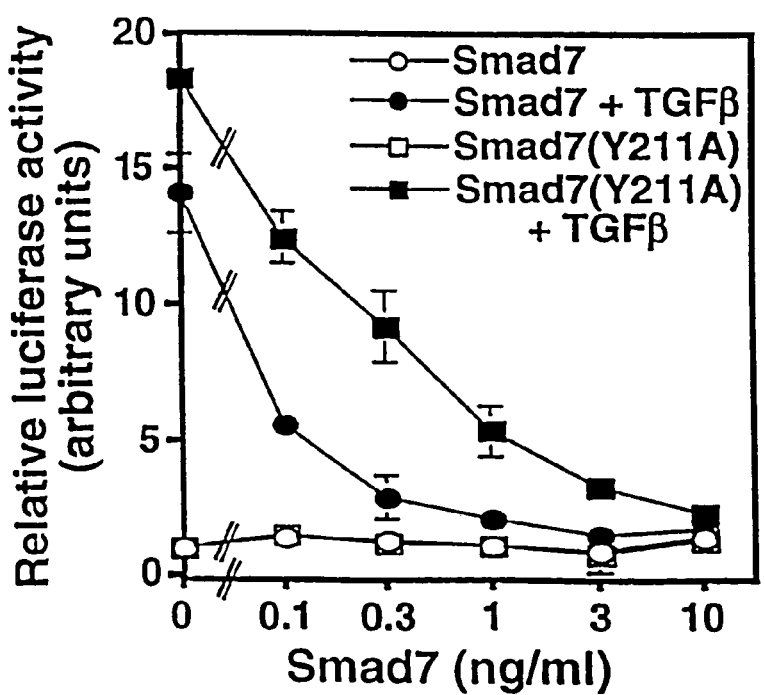
Figure 18A:
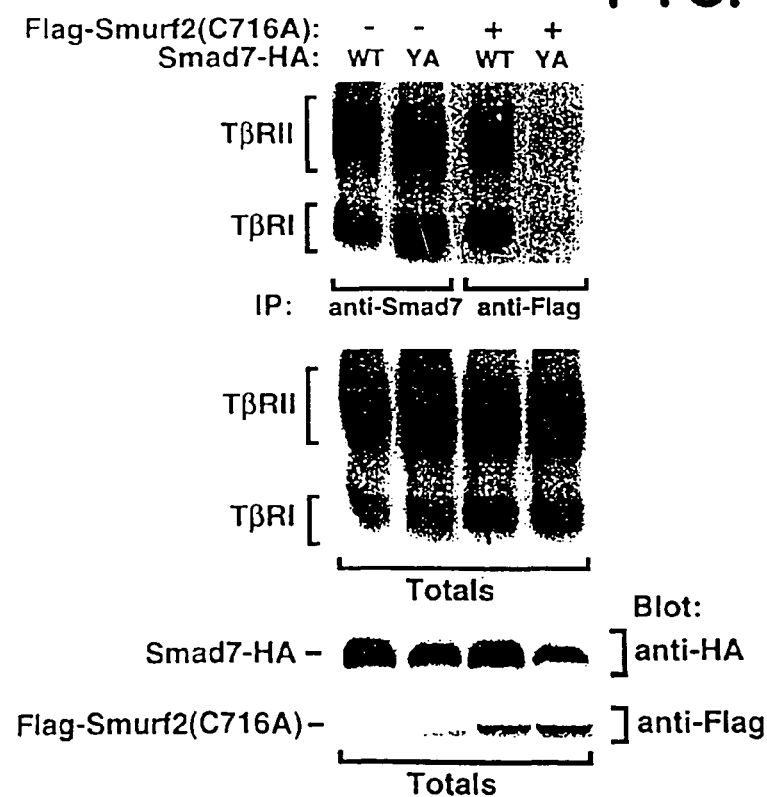
Figure 18B:
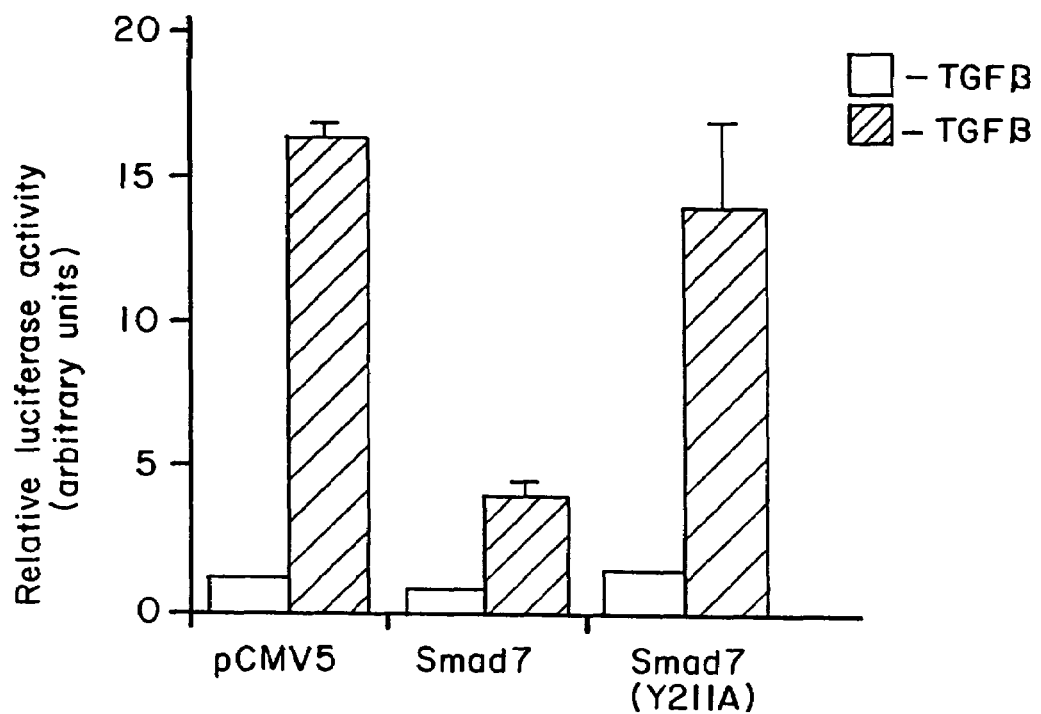

Association of Smurf2 enhances the inhibitory activity of Smad7. Our studies indicate that Smurf2 may be recruited to the TGFβ receptor complex via Smad7 and target the receptors for degradation. This suggests that ubiquitin-mediated degradation may contribute to the inhibitory activity of Smad7 in the TGFβ pathway. To test this we first investigated whether Smad7(Y211A), which displays poor interactions with Smurf2 (see FIG. 15D), has an altered ability to recruit Smurf2 to the TGFβ receptor. For this, wild type Smad7 or Smad7(Y211A) were coexpressed with TGFβ receptors in the presence or absence of Smurf2 (C716A) and receptor interaction was measured by analyzing affinity labelled receptors that coprecipitated with either Smad7 or Smurf2. The interaction of TGFβ receptor complexes with Smad7(Y211A) was comparable to that observed with wild type Smad7 (FIG. 18A), demonstrating that this mutation in the PY motif does not affect Smad7 interaction with the TGFβ receptor. However, the ability of Smurf2(C716A) to associate with TGFβ receptors was substantially reduced in the presence of mutant Smad7, correlating with the reduced efficiency observed for the interaction between Smurf2 and Smad7(Y211A) described above. Next we investigated whether Smad7(Y211A) had an altered capacity to inhibit TGFβ signalling in HepG2 cells, which express endogenous Smurf2. For this, we assessed TGFβ signalling using the well characterized 3TP-lux reporter construct. Expression of wild type Smad7 strongly reduced TGFb-dependent induction of this reporter (FIG. 18B). In contrast, the Smad7(Y211A) mutant had a substantially reduced inhibitory activity, despite its ability to interact efficiently with the TGFβ receptor complex. This suggests that binding of Smurf2 to Smad7 enhances Smad7 inhibitory activity towards the TGFβ signalling pathway.

Previous studies have shown that Smad7 binding to TGFβ receptor complexes prevents access of Smad2 to the receptors. Since Smad7(Y211A) interacts efficiently with the TGFβ receptor, we sought to determine whether the mutant protein might retain inhibitory activity to the TGFβ pathway at higher levels of expression. To examine this, we compared the relative efficiency of Smad7 versus Smad7(Y211A) in blocking TGFβ signalling by varying the amount of Smad7 expression. Wild type Smad7 potently inhibited TGFβ signalling at the lowest doses tested, whereas Smad7(Y211A) was much less efficient (FIG. 18C). However, at the highest dose tested, Smad7(Y211A) was capable of inhibiting TGFβ responsiveness. These results indicate that Smad7(Y211A) retains some inhibitory activity, probably through its ability to bind to the receptor and prevent access of Smad2 or Smad3. Together these data suggest that Smurf2 cooperates with Smad7 to promote its inhibitory activity.

Discussion

Figure 18D:
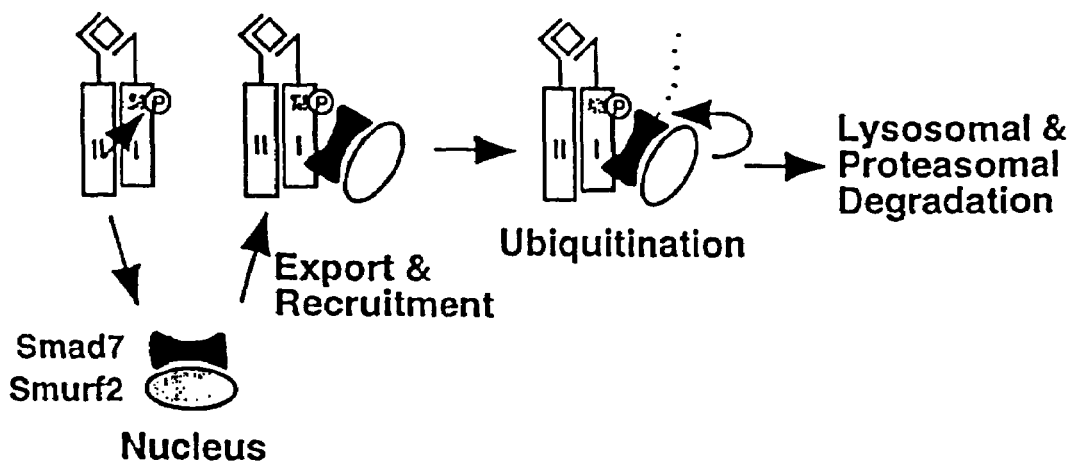

This Example confirms the identity of a new ubiquitin ligase, Smurf2, that functions in partnership with Smad7 to target the TGFβ receptor for degradation. Smurf2 bound TGFβ receptors very weakly and was unable to affect turnover of the receptors. However, in presence of Smad7, Smurf2 formed efficient complexes with the heteromeric TGFβ receptor and targeted the receptors for degradation. Since Smad7 binds directly to Smurf2 and also associates with the TGFβ receptor complex, these results indicated that Smad7 functions as an adaptor protein that mediates the interaction of Smurf2 with the TGFβ receptor complex (FIG. 18D). Consistent with this, mutations in the Smad7 PY motif that disrupted Smad7-Smurf2 interaction also interfered with the ability of Smad7 to recruit Smurf2 into a complex with the receptor. This mutant of Smad7 was also compromised in its ability to block TGFβ signalling, indicating that Smurf2 plays a role in mediating Smad7 inhibitory function. Since Smad7 competes with R-Smads for binding to the activated TGFβ receptor, this cooperation may be particularly important when Smad7 is expressed transiently or at low levels (53-58). By targeting receptors for degradation, Smurf2 can thus provide a mechanism for permanent inactivation of the Smad7-bound receptor complex. Concomitant with Smurf2-dependent degradation of TGFβ receptors, we also observed degradation of Smad7 that was dependent on TGFβ signalling.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein reference in their entireties.

REFERENCES CITED

1. Hogan, B. L., Blessing, M., Winnier, G. E., Suzuki, N. & Jones, C. M. Growth factors in development: The role of TGF-β related polypeptide signaling molecules in embryogenesis. Development. (1995).
2. Kingsley, D. M. The TGF-β superfamily: new members, new receptors, and new genetic tests of function in different organisms. Genes and Develop. 8, 133-146 (1994).
3. Roberts, A. B. & Sporn, M. B. The transforming growth factor-bs. Peptide Growth Factors and Their Receptors 1, 419-472 (1990).
4. Whitman, M. Smads and early developmental signaling by the TGFβ superfamily. Genes and Dev. 12, 2445-2462 (1998).
5. Harland, R. & Gerhart, J. Formation and Function of Spemann's organizer. Annu. Rev. Cell Biol. 13, 611-667 (1997).
6. Heldin, C. H., Miyazono, K. & ten Dijke, P. TGF-beta signaling from cell membrane to nucleus through SMAD proteins. Nature 390, 465-71 (1997).
7. Massague, J. TGF-beta signal transduction. Annu Rev Biochem 67, 753-791 (1998).
8. Wilson, P. A., Lagna, G., Suzuki, A. & Hemmati-Brivanlou, A. Concentration-dependent patterning of the *Xenopus* ectoderm by BMP4 and its signal transducer Smad1. Development 124, 3177-84 (1997).
9. Suzuki, A., Chang, C., Yingling, J. M., Wang, X. F. & Hemmati-Brivanlou, A. Smad5 induces ventral fates in *Xenopus* embryos. Dev. Biol. 184, 402-405 (1997).
10. Graff, J. M., Bansal, A. & Melton, D. A. *Xenopus* Mad proteins transduce distinct subsets of signals for the TGFβ superfamily. Cell 86, 1-20 (1996).
11. Baker, J. C. & Harland, R. M. A novel mesoderm inducer, Madr2, functions in the activin signal transduction pathway. Genes Dev 10, 1880-9 (1996).
12. Hershko, A. & Ciechanover, A. The ubiquitin system. Ann. Rev. Biochem. 67, 425-479 (1998).
13. Hochstrasser, M. Ubiquitin-dependent protein degradation. Annu. Rev. Genet., 405-439 (1996).
14. Pukatzki, S., Tordilla, N., Franke, J. & Kessin, R. H. A novel component involved in ubiquitination is required for development of *Dictyostelium discoideum*. J Biol Chem 273, 24131-8 (1998).
15. Lindsey, D. F., et al. A deubiquitinating enzyme that disassembles free polyubiquitin chains is required for development but not growth in Dictyostelium. J Biol Chem 273, 29178-87 (1998).
16. Chung, C. Y., Reddy, T. B., Zhou, K. & Firtel, R. A. A novel, putative MEK kinase controls developmental timing and spatial patterning in dictyostelium and is regulated by ubiquitin-mediated protein degradation [In Process Citation]. Genes Dev 12, 3564-78 (1998).
17. Epps, J. L. & Tanda, S. The *Drosophila* semushi mutation blocks nuclear import of Bicoid during embryogenesis. Curr. Biol. 8, 1277-1280 (1998).
18. Dickson, B. J. Photoreceptor development: breaking down the barriers. Curr Biol 8, R90-2 (1998).
19. Huang, Y., Baker, R. T. & Fischer-Vize, J. A. Control of cell fate by a deubiquitinating enzyme encoded by the fat facets gene. Science 270, 1828-31 (1995).
20. Jiang, J. & Struhl, G. Regulation of the Hedgehog and Wingless signaling pathways by the F-box/WD40-repeat protein Slimb. Nature 391, 493-6 (1998).
21. Muralidhar, M. G. & Thomas, J. B. The *Drosophila* bendless gene encodes a neural protein related to ubiquitin-conjugating enzymes. Neuron 11, 253-66 (1993).
22. Huibregtse, J. M., Scheffner, M., Beaudenon, S. & Howley, P. M. A family of proteins structurally and functionally related to the E6-AP ubiquitin-protein ligase. Proc Natl Acad Sci USA 92, 2563-7 (1995).
23. Nefsky, B. & Beach, D. Pub1 acts as an E6-AP-like protein ubiquitin ligase in the degradation of cdc25. EMBO J. 15, 1301-1312 (1996).
24. Scheffner, M., Huibregtse, J. M., Vierstra, R. D. & Howley, P. M. The HPV-16 E6 and E6-AP complex functions as a ubiquitin-protein ligase in the ubiquitination of p53. Cell 75, 495-505 (1993).
25. Hein, C., Springael, J., Volland, C., Haguenauer-Tsapis, R. & Andre, B. NP11, an essential yeast gene involved in induced degradation of Gap1 and Fur4 permeases, encodes the Rsp5 ubiquitin-protein ligase. Mol. Microbiol. 18, 77-87 (1995).
26. Kumar, S., et al. cDNA cloning, expression analysis, and mapping of the mouse Nedd4 gene. Genomics 40, 435-43 (1997).
27. Kwon, Y. T., et al. The mouse and human genes encoding the recognition component of the-end rule pathway. Proc Natl Acad Sci USA 95, 7898-903 (1998).
28. Bartel, B., Wunning, I. & Varshavsky, A. The recognition component of the N-end rule pathway. Embo J 9, 3179-89 (1990).
29. Patton, E. E., Willems, A. R. & Tyers, M. Combinatorial control in ubiquitin-dependent proteolysis: don't Skp the F-box hypothesis. Trends. Genet. 14, 236-243 (1998).
30. Wang, G., Yang, J. & Huibregtse, J. M. Functional domains of the rsp5 ubiquitin-protein ligase. Mol Cell Biol 19, 342-52 (1999).
31. Nalefski, E. A. & Falke, J. J. The C2 domain calcium-binding motif: structural and functional diversity. Protein Sci. 5, 2375-2390 (1996).
32. Plant, P. J., Yeger, H., Staub, O., Howard, P. & Rotin, D. The C2 domain of the ubiquitin protein ligase Nedd4 mediates Ca2+-dependent plasma membrane localization. J Biol Chem 272, 32329-36 (1997).
33. Staub, O. & Rotin, D. WW domains. Structure 4, 495-499 (1996).
34. Fainsod, A., Steinbeisser, H. & De Robertis, E. M. On the function of BMP-4 in patterning the marginal zone of the *Xenopus* embryo. Embo J 13, 5015-25 (1994).
35. Hemmati-Brivanlou, A. & Thomsen, G. H. Ventral mesodermal patterning in *Xenopus* embryos: expression patterns and activities of BMP-2 and BMP-4. Dev Genet. 17, 78-89 (1995).
36. Thomsen, G. H. *Xenopus* mothers against decapentaplegic is an embryonic ventralizing agent that acts downstream of the BMP-2/4 receptor. Development 122, 2359-66 (1996).
37. Hoodless, P. A., et al. MADR1, a MAD-related protein that functions in BMP2 signaling pathways. Cell 85, 489-500 (1996).
38. Kretzschmar, M., Liu, F., Hata, A., Doody, J. & Massague, J. The TGF-beta family mediator Smad1 is phosphorylated directly and activated functionally by the BMP receptor kinase. Genes Dev 11, 984-95 (1997).
39. Thomsen, G. H. Antagonism within and around the Spemann organizer: BMPs and their binding proteins in dorsal-ventral patterning. Trends Genet. 13, 209-211 (1997).
40. Sasai, Y. & De Robertis, E. M. Ectodermal patterning in vertebrate embryos. Dev Biol 182, 5-20 (1997).
41. Hemmati-Brivanlou, A. & Melton, D. Vertebrate embryonic cells will become nerve cells unless told otherwise. Cell 88, 13-17 (1997).
42. Kawabata, M., Imamura, T. & Miyazono, K. Signal transduction by bone morphogenetic proteins. Cytokine Growth Factor Rev 9, 49-61 (1998).
43. Bashirullah, A., Cooperstock, R. L. & Lipshitz, H. D. RNA localization in development. Annu Rev Biochem 67, 335-94 (1998).
44. Kimelman, D. & Griffin, K. J. Mesoderm induction: a postmodern view. Cell 94, 419-21 (1998).
45. Joseph, E. M. & Melton, D. A. Mutant Vg1 ligands disrupt endoderm and mesoderm formation in *Xenopus* embryos. Development 125, 2677-85 (1998).
46. Bartel, P. & Fields, S. Analyzing protein-protein interactions using two-hybrid system. Methods Enzymol. 254, 241-263 (1995).
47. Eppert, K., et al. MADR2 maps to 18q21 and encodes a TGFβ regulated MAD-related protein that is functionally mutated in colorectal carcinoma. Cell 86, 543-552 (1996).
48. Horb, M. E. & Thomsen, G. H. A vegetally-localized *Xenopus* T-box gene specifies mesoderm and endoderm and is essential for mesoderm formation. Dev. 124, 1689-1698 (1997).
49. Wigler, M., et al. Transformation of mammalian cells with genes from procaryotes and eucaryotes. Cell 16, 777-85 (1979).
50. Macias-Silva, M., Hoodless, P. A., Tang, S. J., Buchwald, M. & Wrana, J. L. Specific activation of Smad1 signaling pathways by the BMP7 type I receptor, ALK2. J Biol Chem 273, 25628-36 (1998).
51. Staub, O., et al. Immunolocalization of the ubiquitin-protein ligase Nedd4 in tissues expressing the epithelial Na+ channel (ENaC). Am J Physiol 272, C1871-80 (1997).
52. Reddi, A. H., Role of morphogenetic proteins in skeletal tissue engineering and regeneration, Nature Biotechnology 16, 247-252 (1998).
53. Afrakhte, M., Morén, A., Jossan, S., Itoh, S., Sampath, K., Westermark, B., Heldin, C.-H., Heldin, N.-E., and ten Dijke, P. (1998). Induction of Inhibitory Smad6 and Smad7 mRNA by TGF-b Family Members. Biochem. Biophys. Res. Comm. 249, 505-511.
54. Bitzer, M., von Gersdorff, G., Liang, D., Dominguez-Rosales, A., Beg, A. A., Rojkind, M., and Bottinger, E. P. (2000). A mechanism of suppression of TGF-b/Smad signaling by NF-kB/RelA. Genes Dev. 14, 187-197.
55. Ishiaki, A., Yamato, K., Nakao, A., Nonaka, K., Ohguchi, M., ten Dijke, P., and Nishihara, T. (1998). Smad7 Is an Activin-inducible Inhibitor of Activin-induced Growth Arrest and Apoptosis in Mouse B Cells. J. Biol. Chem. 273, 24293-24296.
56. Nakao, A., Afrakhte, M., Morén, A., Nakayama, T., Christian, J. L., Heuchel, R., Itoh, S., Kawabata, M., Heldin, N.-E., Heldin, C.-H., and ten Dijke, P. (1997). Identification of Smad7, a TGFb-inducible antagonist of TGF-b signalling. Nature 389, 631-635.
57. Takase, M., Imamura, T., Sampath, T. K., Takeda, K., Ichijo, H., Miyazono, K., and Kawabata, M. (1998). Induction of Smad6 mRNA by bone morphogenetic proteins. Biochem. Biophys. Res. Commun. 244, 26-29.
58. Ulloa, L., Doody, J., and Massagué, J. (1999). Inhibition of transforming growth factor-b/SMAD signalling by the interferon-n/STAT pathway. Nature 397, 710-713.
59. Bonifacino, J. S., and Weissman, A. M. (1998). Ubiquitin and the control of protein fate in the secretory and endocytic pathways. Ann. Rev. Cell. Biol. 14, 19-57.
60. Hicke, L. (1999). Gettin' down with ubiquitin: turning off cell-surface receptors, transporters and channels. Trends Cell Biol. 9, 107-112.
61. Govers, R., ten Broeke, T., van Kerkhof, P., Schwartz, A. L., and Strous, G. J. (1999). Identification of a novel ubiquitin conjugation motif, required, for ligand-induced internalization of the growth hormone receptor. EMBO J. 18, 28-36.
62. van Kerkhof, P., Govers, R., Alves dos Santos, C. M., and Strous, G. J. (2000). Endocytosis and degradation of the Growth Hormone Receptor are proteasome-dependent. J. Biol. Chem. 275, 1575-1580.
63. Harvey, K. F., and Kumar, S. (1999). Nedd4-like proteins: an emerging family of ubiquitin-protein ligases implicated in diverse cellular functions. Trends Cell Biol. 9, 166-169.
64. Staub, O., Abriel, H., Plant, P., Ishikawa, T., Kanelis, V., Saleki, R., Horisberger, J. D., Schild, L., and Rotin, D. (2000). Regulation of the epithelial Na+ channel by Nedd4 and ubiquitination. Kidney Int. 57, 809-815.
65. Staub, O., Dho, S., Henry, P., Correa, J., Ishikawa, T., McGlade, J., and Rotin, D. (1996). WW domains of Nedd4 bind to the proline-rich PY motifs in the epithelial Na+ channel deleted in Liddle's syndrome. EMBO J. 15, 2371-2380.
66. Staub, O., Gautschi, I., Ishikawa, T., Breitschopf, K., Ciechanover, A., Schild, L., and Rotin, D. (1997). Regulation of stability and function of the epithelial Na+ channel (ENaC) by ubiquitination. EMBO J. 16, 6325-6336.
67. Joazeiro, C. A. P., Wing, S. S., Huang, H.-K., Leverson, J. D., Hunter, T., and Liu, Y.-C. (1999). The tyrosine kinase negative regulator c-cbl as a RING-type E2-dependent ubiquitin-protein ligase. Science 286, 309-312.
68. Levkowitz, G., Waterman, H., Ettenberg, S. A., Katz, M., Tsygankov, A. Y., Alroy, I., Lavi, S., Iwai, K., Reiss, Y., Ciechanover, A., Lipkowitz, S., and Yarden, Y. (1999). Ubiquitin ligase activity and tyrosine phosphorylation underlie suppression of growth factor signaling by c-Cbl/Sli-1. Mol. Cell. 4, 1029-1040.
69. Hoodless, P. A., Haerry, T., Abdollah, S., Stapleton, M., O'Connor, M. B., Attisano, L., and Wrana, J. L. (1996). MADR1, a MAD-related protein that functions in BMP2 signalling pathways. Cell 85, 489-500.
70. Macías-Silva, M., Abdollah, S., Hoodless, P. A., Pirone, R., Attisano, L., and Wrana, J. L. (1996). MADR2 is a substrate of the TGFβ receptor and its phosphorylation is required for nuclear accumulation and signalling. Cell 87, 1215-1224.
71. Chen, H. I., and Sudol, M. (1995). The WW domain of Yes-associated protein binds a proline-rich ligand that differs from the consensus established for Src homology 3-binding modules. Proc Natl Acad Sci USA 82, 7819-7823.

72. Hayashi, H., Abdollah, S., Qiu, Y., Cai, J., Xu, Y.-Y., Grinnell, B. W., Richardson, M. A., Topper, J. N., Gimbrone Jr., M. A., Wrana, J. L., and Falb, D. (1997). The MAD-related protein Smad7 associates with the TGFβ receptor and functions as an antagonist of TGFβ signaling. Cell 89, 1165-1173.

73. Itoh, S., Landstrom, M., Hermansson, A., Itoh, F., Heldin, C.-H., Heldin, N.-E., and ten Dijke, P. (1998). Transforming Growth Factor b1 induces nuclear export of inhibitory Smad7. J. Biol. Chem. 273, 29195-29201.

74. Gilboa, L., Wells, R. G., Lodish, H. F., and Henis, Y. I. (1998). Oligomeric structure of type I and type II Transforming Growth Factor-b receptors: Homodimers form in the ER and persist at the plasma membrane. J. Cell. Biol. 140, 767-777.

75. Henis, Y. I., Moustakas, A., Lin, H. Y., and Lodish, H. F. (1994). The type II and III transforming growth factor-β receptors form homo-oligomers. J. Cell Biol. 126, 139-154.

76. Tsukazaki, T., Chiang, T. A., Davison, A. F. Attisano, L., and Wrana, J. L. (1998). SARA, a FYVE domain protein that recruits Smad2 to the TGF-b receptor. Cell 95, 779-791.

77. Derynck, R., Zhang, Y., and Feng, X.-H. (199S). Smads: Transcriptional activators of TGF-b responses. Cell 95, 737-740.

78. Heldin, C.-H., Miyazono, K., and ten Dijke, P. (1997). TGF-b signalling from cell membrane to nucleus through SMAD proteins. Nature. 390, 465-471.

79. Massagué, J., and Chen, Y. G. (2000). Controlling TGF-beta signaling. Genes Dev. 14, 627-644.

80. Miyazono, K. (2000). TGF-beta signaling by Smad proteins. Cyto. Growth Factor Rev. 11, 15-22.

81. Wrana, J. L. (2000). Regulation of Smad Activity. Cell 100, 189-192.

82. Imamura, T., Takase, M., Nishihara, A., Oeda. E., Hanai, J.-I., Kawabata, M., and Miyazono, K. (1997). Smad6 inhibits signalling by the TGF-b superfamily. Nature 389, 622-626.

What is claimed is:

1. A method of screening for a modulator of Smurf activity which comprises detecting modulation of Smurf activity in the presence of a test compound relative to Smurf activity in the absence of the test compound, wherein the Smurf activity detected is the activity of a Smurf comprising a WW domain and a HECT domain, wherein the Smurf comprises the amino acid sequence depicted in SEQ ID NO:2, and wherein the Smurf activity is ubiquitination of a Smad polypeptide, ubiquitination of a TGFβ receptor or interaction of a Smurf WW domain with a PPXY domain of a Smad polypeptide.

2. The method according to claim 1, wherein the Smurf activity is ubiquitination of a Smad polypeptide in a host cell.

3. The method according to claim 1, wherein the Smurf activity is interaction of a Smurf WW domain with a PPXY domain of a Smad polypeptide.

4. The method according to claim 3, wherein the test compound is screened for the ability to inhibit the interaction.

5. The method according to claim 1, wherein the Smurf activity detected is the activity of a Smurf comprising the amino acid sequence depicted in SEQ ID NO:2.

6. A method of screening for a modulator of Smurf activity which comprises detecting modulation of Smurf activity in the presence of a test compound relative to Smurf activity in the absence of the test compound, wherein the Smurf activity detected is activity of a human Smurf comprising the amino acid sequence depicted in SEQ ID NO:4, and wherein the Smurf activity is ubiquitination of a Smad polypeptide in a host cell, interaction of a Smurf WW domain with a PPXY domain of a Smad polypeptide, or ubiquitination of a TGFβ receptor.

7. The method according to claim 6, wherein the Smurf activity is ubiquitination of a Smad polypeptide.

8. The method according to claim 6, wherein the Smurf activity is ubiquitination of a Smad polypeptide in a host cell.

9. The method according to claim 6, wherein the Smurf activity is interaction of a Smurf WW domain with a PPXY domain of a Smad polypeptide.

10. The method according to claim 9, wherein the test compound is screened for the ability to inhibit the interaction.

11. The method according to claim 6, wherein the Smurf activity is ubiquitination of a TGFβ receptor.

12. The method according to claim 6, wherein the screening assay is conducted in vitro.

13. The method according to claim 6, wherein the screening assay is conducted in a host cell.

14. The method according to claim 1, wherein the Smurf activity is ubiquitination of a Smad polypeptide.

15. The method according to claim 1, wherein the Smurf activity is ubiquitination of a TGFβ receptor.

16. The method according to claim 1, wherein the screening assay is conducted in vitro.

17. The method according to claim 1, wherein the screening assay is conducted in a host cell.

18. The method according to claim 1, wherein the screening assay is conducted in vivo.

19. The method according to claim 6, wherein the screening assay is conducted in vivo.

* * * * *

```
                        SEQUENCE LISTING

<160> NUMBER OF SEQ ID NOS: 13

<210> SEQ ID NO 1
<211> LENGTH: 2172
<212> TYPE: DNA
<213> ORGANISM: Homo sapiens
<220> FEATURE:
<223> OTHER INFORMATION: Human Smurf1

<400> SEQUENCE: 1
ggaggctcca gcatcaagat ccgtctgaca gtgttatgtg ccaagaacct tgcaaagaaa      60
gacttcttca ggctccctga ccctttgca aagattgtcg tggatgggtc tgggcagtgc     120
cactcaaccg acactgtgaa aaacacattg gacccaaagt ggaaccagca ctatgatcta    180
tatgttggga aaacggattc gataaccatt agcgtgtgga accataagaa aattcacaag    240
aaacagggag ctggcttcct gggctgtgtg cggctgctct ccaatgccat cagcagatta    300
aaagataccg gataccagcg tttggatcta tgcaaactaa accctcaga tactgatgca     360 gttcgtggcc agatagtggt cagtttacag acacgagaca gaataggaac cggcggctcg    420
gtggtggact gcagaggact gttagaaaat gaaggaacgg tgtatgaaga ctccgggcct    480
gggaggccgc tcagctgctt catggaggaa ccagcccctt acacagatag caccggtgct    540
gctgctggag gagggaattg caggttcgtg gagtccccaa gtcaagatca aagacttcag    600
gcacagcggc ttcgaaaccc tgatgtgcga ggttcactac agacgcccca gaaccgacca    660
cacggccacc agtccccgga actgcccgaa ggctacgaac aaagaacaac agtccagggc    720
caagtttact ttttgcatac acagactgga gttagcacgt ggcacgaccc caggatacca    780
agagacctta acagtgtgaa ctgtgatgaa cttggaccac tgccgccagg ctgggaagtc    840
agaagtacag tttctgggag gatatatttt gtagatcata taaccgaac aacccagttt    900 acagacccaa ggttacacca catcatgaat caccagtgcc aactcaagga gcccagccag    960
ccgctgccac tgcccagtga gggctctctg gaggacgagg agcttcctgc ccagagatac    1020
gaaagagatc tagtccagaa gctgaaagtc ctcagacacg aactgtcgct tcagcagccc    1080
```

-continued

```
caagctggtc attgccgcat cgaagtgtcc agagaagaaa tctttgagga gtcttaccgc    1140
cagataatga agatgcgacc gaaagacttg aaaaaacggc tgatggtgaa attccgtggg    1200
gaagaaggtt tggattacgg tggtgtggcc agggagtggc tttacttgct gtgccatgaa    1260
atgctgaatc cttattacgg gctcttccag tattctacgg acaatattta catgttgcaa    1320
ataaatccgg attcttcaat caaccccgac cacttgtctt atttccactt tgtggggcgg    1380
atcatggggc tggctgtgtt ccatggacac tacatcaacg ggggcttcac agtgcccttc    1440
tacaagcagc tgctggggaa gcccatccag ctctcagatc tggaatctgt ggacccagag    1500
ctgcataaga gcttggtgtg gatcctagag aacgacatca cgcctgtact ggaccacacc    1560
ttctgcgtgg aacacaacgc cttcgggcgg atcctgcagc atgaactgaa acccaatggc    1620
agaaatgtgc cagtcacaga ggagaataag aaagaatacg tccggttgta tgtaaactgg    1680
aggtttatga gaggaatcga agcccagttc ttagctctgc agaagggggtt caatgagctc    1740 atccctcaac atctgctgaa gccttttgac cagaaggaac tggagctgat cataggcggc    1800
ctggataaaa tagacttgaa cgactggaag tcgaacacgc ggctgaagca ctgtgtggcc    1860
gacagcaaca tcgtgcggtg gttctggcaa gcggtggaga cgttcgatga agaaaggagg    1920
gccaggctcc tgcagtttgt gactgggtcc acgcgagtcc cgctccaagg cttcaaggct    1980
ttgcaaggtt ctacaggcgc ggcagggccc cggctgttca ccatccacct gatagacgcg    2040
aacacagaca accttccgaa ggcccatacc tgctttaacc ggatcgacat tccaccatat    2100
gagtcctatg agaagctcta cgagaagctg ctgacagccg tggaggagac ctgcgggttt    2160
gctgtggagt aa                                                        2172
```

<210> SEQ ID NO 2
<211> LENGTH: 723
<212> TYPE: PRT
<213> ORGANISM: Homo sapiens
<220> FEATURE:
<223> OTHER INFORMATION: Human Smurf1

<400> SEQUENCE: 2

```
Gly Gly Ser Ser Ile Lys Ile Arg Leu Thr Val Leu Cys Ala Lys Asn
1               5                   10                  15

Leu Ala Lys Lys Asp Phe Phe Arg Leu Pro Asp Pro Phe Ala Lys Ile
            20                  25                  30

Val Val Asp Gly Ser Gly Gln Cys His Ser Thr Asp Thr Val Lys Asn
        35                  40                  45

Thr Leu Asp Pro Lys Trp Asn Gln His Tyr Asp Leu Tyr Val Gly Lys
    50                  55                  60

Thr Asp Ser Ile Thr Ile Ser Val Trp Asn His Lys Lys Ile His Lys
65                  70                  75                  80

Lys Gln Gly Ala Gly Phe Leu Gly Cys Val Arg Leu Leu Ser Asn Ala
                85                  90                  95

Ile Ser Arg Leu Lys Asp Thr Gly Tyr Gln Arg Leu Asp Leu Cys Lys
            100                 105                 110

Leu Asn Pro Ser Asp Thr Asp Ala Val Arg Gly Gln Ile Val Val Ser
        115                 120                 125

Leu Gln Thr Arg Asp Arg Ile Gly Thr Gly Gly Ser Val Val Asp Cys
    130                 135                 140

Arg Gly Leu Leu Glu Asn Glu Gly Thr Val Tyr Glu Asp Ser Gly Pro
145                 150                 155                 160
```

```
Gly Arg Pro Leu Ser Cys Phe Met Glu Glu Pro Ala Pro Tyr Thr Asp
                165                 170                 175
Ser Thr Gly Ala Ala Gly Gly Asn Cys Arg Phe Val Glu Ser
            180                 185                 190
Pro Ser Gln Asp Gln Arg Leu Gln Ala Gln Arg Leu Arg Asn Pro Asp
            195                 200                 205
Val Arg Gly Ser Leu Gln Thr Pro Gln Asn Arg Pro His Gly His Gln
    210                 215                 220
Ser Pro Glu Leu Pro Glu Gly Tyr Glu Gln Arg Thr Thr Val Gln Gly
225                 230                 235                 240
Gln Val Tyr Phe Leu His Thr Gln Thr Gly Val Ser Thr Trp His Asp
                245                 250                 255
Pro Arg Ile Pro Arg Asp Leu Asn Ser Val Asn Cys Asp Glu Leu Gly
            260                 265                 270
Pro Leu Pro Pro Gly Trp Glu Val Arg Ser Thr Val Ser Gly Arg Ile
        275                 280                 285
Tyr Phe Val Asp His Asn Asn Arg Thr Thr Gln Phe Thr Asp Pro Arg
    290                 295                 300
Leu His His Ile Met Asn His Gln Cys Gln Leu Lys Glu Pro Ser Gln
305                 310                 315                 320
Pro Leu Pro Leu Pro Ser Glu Gly Ser Leu Glu Asp Glu Glu Leu Pro
                325                 330                 335
Ala Gln Arg Tyr Glu Arg Asp Leu Val Gln Lys Leu Lys Val Leu Arg
            340                 345                 350
His Glu Leu Ser Leu Gln Gln Pro Gln Ala Gly His Cys Arg Ile Glu
        355                 360                 365
Val Ser Arg Glu Glu Ile Phe Glu Glu Ser Tyr Arg Gln Ile Met Lys
    370                 375                 380
Met Arg Pro Lys Asp Leu Lys Lys Arg Leu Met Val Lys Phe Arg Gly
385                 390                 395                 400
Glu Glu Gly Leu Asp Tyr Gly Gly Val Ala Arg Glu Trp Leu Tyr Leu
                405                 410                 415
Leu Cys His Glu Met Leu Asn Pro Tyr Tyr Gly Leu Phe Gln Tyr Ser
            420                 425                 430
Thr Asp Asn Ile Tyr Met Leu Gln Ile Asn Pro Asp Ser Ser Ile Asn
        435                 440                 445
Pro Asp His Leu Ser Tyr Phe His Phe Val Gly Arg Ile Met Gly Leu
    450                 455                 460
Ala Val Phe His Gly His Tyr Ile Asn Gly Gly Phe Thr Val Pro Phe
465                 470                 475                 480
Tyr Lys Gln Leu Leu Gly Lys Pro Ile Gln Leu Ser Asp Leu Glu Ser
                485                 490                 495
Val Asp Pro Glu Leu His Lys Ser Leu Val Trp Ile Leu Glu Asn Asp
            500                 505                 510
Ile Thr Pro Val Leu Asp His Thr Phe Cys Val Glu His Asn Ala Phe
        515                 520                 525
Gly Arg Ile Leu Gln His Glu Leu Lys Pro Asn Gly Arg Asn Val Pro
    530                 535                 540
Val Thr Glu Glu Asn Lys Lys Glu Tyr Val Arg Leu Tyr Val Asn Trp
545                 550                 555                 560
Arg Phe Met Arg Gly Ile Glu Ala Gln Phe Leu Ala Leu Gln Lys Gly
                565                 570                 575
Phe Asn Glu Leu Ile Pro Gln His Leu Leu Lys Pro Phe Asp Gln Lys
```

-continued

```
           580             585             590
Glu Leu Glu Leu Ile Ile Gly Gly Leu Asp Lys Ile Asp Leu Asn Asp
        595                 600                 605
Trp Lys Ser Asn Thr Arg Leu Lys His Cys Val Ala Asp Ser Asn Ile
    610                 615                 620
Val Arg Trp Phe Trp Gln Ala Val Glu Thr Phe Asp Glu Glu Arg Arg
625                 630                 635                 640
Ala Arg Leu Leu Gln Phe Val Thr Gly Ser Thr Arg Val Pro Leu Gln
                645                 650                 655
Gly Phe Lys Ala Leu Gln Gly Ser Thr Gly Ala Ala Gly Pro Arg Leu
            660                 665                 670
Phe Thr Ile His Leu Ile Asp Ala Asn Thr Asp Asn Leu Pro Lys Ala
        675                 680                 685
His Thr Cys Phe Asn Arg Ile Asp Ile Pro Pro Tyr Glu Ser Tyr Glu
    690                 695                 700
Lys Leu Tyr Glu Lys Leu Leu Thr Ala Val Glu Glu Thr Cys Gly Phe
705                 710                 715                 720
Ala Val Glu
```

<210> SEQ ID NO 3
<211> LENGTH: 2247
<212> TYPE: DNA
<213> ORGANISM: Homo sapiens
<220> FEATURE:
<223> OTHER INFORMATION: Human Smurf2

<400> SEQUENCE: 3

```
atgtctaacc ccggacgccg gaggaacggg cccgtcaagc tgcgcctgac agtactctgt      60
gcaaaaaacc tggtgaaaaa ggattttttc cgacttcctg atccatttgc taaggtggtg     120
gttgatggat ctgggcaatg ccattctaca gatactgtga agaatacgct tgatccaaag     180
tggaatcagc attatgacct gtatattgga aagtctgatt cagttacgat cagtgtatgg     240
aatcacaaga gatccataa gaaacaaggt gctggatttc tcggttgtgt tcgtcttctt     300
tccaatgcca tcaaccgcct caaagacact ggttatcaga ggttggattt atgcaaactc     360
gggccaaatg acaatgatac agttagagga cagatagtag taagtcttca gtccagagac     420
cgaataggca caggaggaca agttgtggac tgcagtcgtt tatttgataa cgatttacca     480
gacggctggg aagaaaggag aaccgcctct ggaagaatcc agtatctaaa ccatataaca     540
agaactacgc aatgggagcg cccaacacga ccggcatccg aatattctag ccctggcaga     600
cctcttagct gctttgttga tgagaacact ccaattagtg aacaaatggt gcaacatgt      660
ggacagtctt cagatcccag gctggcagag aggagagtca ggtcacaacg acatagaaat     720
tacatgagca gaacacattt acatactcct ccagacctac agaaggcta tgaacagagg     780
acaacgcaac aaggccaggt gtatttctta catacacaga ctggtgtgag cacatggcat     840
gatccaagag tgcccaggga tcttagcaac atcaattgtg aagagcttgg tccattgcct     900
cctggatggg agatccgtaa tacggcaaca ggcagagttt atttcgttga ccataacaac     960
agaacaacac aatttacaga tcctcggctg tctgctaact tgcatttagt tttaaatcgg    1020
cagaaccaat tgaaagacca acagcaacag caagtggtat cgttatgtcc tgatgacaca    1080
gaatgcctga cagtcccaag gtacaagcga gacctggttc agaaactaaa aattttgcgg    1140
caagaacttt cccaacaaca gcctcaggca ggtcattgcc gcattgaggt ttccagggaa    1200
gagatttttg aggaatcata tcgacaggtc atgaaaatga gaccaaaaga tctctggaag    1260
```

-continued

```
cgattaatga taaaatttcg tggagaagaa ggccttgact atggaggcgt tgccagggaa    1320
tggttgtatc tcttgtcaca tgaaatgttg aatccatact atggcctctt ccagtattca    1380
agagatgata tttatacatt gcagatcaat cctgattctg cagttaatcc ggaacattta    1440
tcctatttcc actttgttgg acgaataatg ggaatggctg tgtttcatgg acattatatt    1500
gatggtggtt tcacattgcc ttttataag caattgcttg ggaagtcaat taccttggat     1560
gacatggagt tagtagatcc ggatcttcac aacagtttag tgtggatact tgagaatgat    1620
attacaggtg ttttggacca taccttctgt gttgaacata atgcatatgg tgaaattatt    1680
cagcatgaac ttaaaccaaa tggcaaaagt atccctgtta atgaagaaaa taaaaaagaa    1740
tatgtcaggc tctatgtgaa ctggagattt ttacgaggca ttgaggctca attcttggct    1800
ctgcagaaag gatttaatga agtaattcca caacatctgc tgaagacatt tgatgagaag    1860
gagttagagc tcattatttg tggacttgga aagatagatg ttaatgactg gaaggtaaac    1920
acccggttaa aacactgtac accagacagc aacattgtca aatggttctg gaaagctgtg    1980
gagttttttg atgaagagcg acgagcaaga ttgcttcagt ttgtgacagg atcctctcga    2040
gtgcctctgc agggcttcaa agcattgcaa ggtgctgcag gcccgagact ctttaccata    2100
caccagattg atgcctgcac taacaacctg ccgaaagccc acacttgctt caatcgaata    2160
gacattccac cctatgaaag ctatgaaaag ctatatgaaa agctgctaac agccattgaa    2220
gaaacatgtg gatttgctgt ggaatga                                        2247
```

<210> SEQ ID NO 4
<211> LENGTH: 748
<212> TYPE: PRT
<213> ORGANISM: Homo sapiens
<220> FEATURE:
<223> OTHER INFORMATION: Human Smurf1

<400> SEQUENCE: 4

```
Met Ser Asn Pro Gly Arg Arg Asn Gly Pro Val Lys Leu Arg Leu
1               5                   10                  15

Thr Val Leu Cys Ala Lys Asn Leu Val Lys Lys Asp Phe Phe Arg Leu
            20                  25                  30

Pro Asp Pro Phe Ala Lys Val Val Val Asp Gly Ser Gly Gln Cys His
        35                  40                  45

Ser Thr Asp Thr Val Lys Asn Thr Leu Asp Pro Lys Trp Asn Gln His
    50                  55                  60

Tyr Asp Leu Tyr Ile Gly Lys Ser Asp Ser Val Thr Ile Ser Val Trp
65                  70                  75                  80

Asn His Lys Lys Ile His Lys Lys Gln Gly Ala Gly Phe Leu Gly Cys
                85                  90                  95

Val Arg Leu Leu Ser Asn Ala Ile Asn Arg Leu Lys Asp Thr Gly Tyr
            100                 105                 110

Gln Arg Leu Asp Leu Cys Lys Leu Gly Pro Asn Asp Asn Asp Thr Val
        115                 120                 125

Arg Gly Gln Ile Val Val Ser Leu Gln Ser Arg Asp Arg Ile Gly Thr
    130                 135                 140

Gly Gly Gln Val Val Asp Cys Ser Arg Leu Phe Asp Asn Asp Leu Pro
145                 150                 155                 160

Asp Gly Trp Glu Glu Arg Arg Thr Ala Ser Gly Arg Ile Gln Tyr Leu
                165                 170                 175

Asn His Ile Thr Arg Thr Thr Gln Trp Glu Arg Pro Thr Arg Pro Ala
```

-continued

```
                180                 185                 190
Ser Glu Tyr Ser Ser Pro Gly Arg Pro Leu Ser Cys Phe Val Asp Glu
            195                 200                 205
Asn Thr Pro Ile Ser Gly Thr Asn Gly Ala Thr Cys Gly Gln Ser Ser
        210                 215                 220
Asp Pro Arg Leu Ala Glu Arg Val Arg Ser Gln Arg His Arg Asn
225                 230                 235                 240
Tyr Met Ser Arg Thr His Leu His Thr Pro Asp Leu Pro Glu Gly
            245                 250                 255
Tyr Glu Gln Arg Thr Thr Gln Gln Gly Gln Val Tyr Phe Leu His Thr
            260                 265                 270
Gln Thr Gly Val Ser Thr Trp His Asp Pro Arg Val Pro Arg Asp Leu
        275                 280                 285
Ser Asn Ile Asn Cys Glu Glu Leu Gly Pro Leu Pro Pro Gly Trp Glu
        290                 295                 300
Ile Arg Asn Thr Ala Thr Gly Arg Val Tyr Phe Val Asp His Asn Asn
305                 310                 315                 320
Arg Thr Thr Gln Phe Thr Asp Pro Arg Leu Ser Ala Asn Leu His Leu
                325                 330                 335
Val Leu Asn Arg Gln Asn Gln Leu Lys Asp Gln Gln Gln Gln Val
            340                 345                 350
Val Ser Leu Cys Pro Asp Asp Thr Glu Cys Leu Thr Val Pro Arg Tyr
        355                 360                 365
Lys Arg Asp Leu Val Gln Lys Leu Lys Ile Leu Arg Gln Glu Leu Ser
                375                 380
        370
Gln Gln Gln Pro Gln Ala Gly His Cys Arg Ile Glu Val Ser Arg Glu
385                 390                 395                 400
Glu Ile Phe Glu Glu Ser Tyr Arg Gln Val Met Lys Met Arg Pro Lys
                405                 410                 415
Asp Leu Trp Lys Arg Leu Met Ile Lys Phe Arg Gly Glu Glu Gly Leu
                420                 425                 430
Asp Tyr Gly Gly Val Ala Arg Glu Trp Leu Tyr Leu Leu Ser His Glu
            435                 440                 445
Met Leu Asn Pro Tyr Tyr Gly Leu Phe Gln Tyr Ser Arg Asp Asp Ile
        450                 455                 460
Tyr Thr Leu Gln Ile Asn Pro Asp Ser Ala Val Asn Pro Glu His Leu
465                 470                 475                 480
Ser Tyr Phe His Phe Val Gly Arg Ile Met Gly Met Ala Val Phe His
                485                 490                 495
Gly His Tyr Ile Asp Gly Gly Phe Thr Leu Pro Phe Tyr Lys Gln Leu
            500                 505                 510
Leu Gly Lys Ser Ile Thr Leu Asp Asp Met Glu Leu Val Asp Pro Asp
        515                 520                 525
Leu His Asn Ser Leu Val Trp Ile Leu Glu Asn Asp Ile Thr Gly Val
        530                 535                 540
Leu Asp His Thr Phe Cys Val Glu His Asn Ala Tyr Gly Glu Ile Ile
545                 550                 555                 560
Gln His Glu Leu Lys Pro Asn Gly Lys Ser Ile Pro Val Asn Glu Glu
                565                 570                 575
Asn Lys Lys Glu Tyr Val Arg Leu Tyr Val Asn Trp Arg Phe Leu Arg
            580                 585                 590
Gly Ile Glu Ala Gln Phe Leu Ala Leu Gln Lys Gly Phe Asn Glu Val
            595                 600                 605
```

```
Ile Pro Gln His Leu Leu Lys Thr Phe Asp Glu Lys Glu Leu Glu Leu
        610                 615                 620

Ile Ile Cys Gly Leu Gly Lys Ile Asp Val Asn Asp Trp Lys Val Asn
625                 630                 635                 640

Thr Arg Leu Lys His Cys Thr Pro Asp Ser Asn Ile Val Lys Trp Phe
                645                 650                 655

Trp Lys Ala Val Glu Phe Phe Asp Glu Glu Arg Arg Ala Arg Leu Leu
                660                 665                 670

Gln Phe Val Thr Gly Ser Ser Arg Val Pro Leu Gln Gly Phe Lys Ala
            675                 680                 685

Leu Gln Gly Ala Ala Gly Pro Arg Leu Phe Thr Ile His Gln Ile Asp
        690                 695                 700

Ala Cys Thr Asn Asn Leu Pro Lys Ala His Thr Cys Phe Asn Arg Ile
705                 710                 715                 720

Asp Ile Pro Pro Tyr Glu Ser Tyr Glu Lys Leu Tyr Glu Lys Leu Leu
                725                 730                 735

Thr Ala Ile Glu Glu Thr Cys Gly Phe Ala Val Glu
            740                 745

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
gtcctgtgac tggaaccc                                               18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 6
gaggactgct agacaat                                                17

<210> SEQ ID NO 7
<211> LENGTH: 731
<212> TYPE: PRT
<213> ORGANISM: Xenopus sp.

<400> SEQUENCE: 7

Met Ser Asn Val Val Thr Arg Arg Gly Gly Ser Ser Ile Arg Val Arg
1               5                   10                  15

Leu Thr Val Leu Cys Ala Lys Asn Leu Ala Lys Arg Asp Phe Phe Arg
            20                  25                  30

Leu Pro Asp Pro Phe Ala Lys Ile Val Val Asp Gly Ser Gly Gln Cys
        35                  40                  45

His Ser Thr Asp Thr Val Lys Asn Thr Leu Asp Pro Lys Trp Asn Gln
    50                  55                  60

His Tyr Asp Leu Tyr Val Gly Lys Met Asp Ser Ile Thr Ile Ser Ile
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
```

-continued

```
              100                 105                 110
Tyr Gln Arg Leu Asp Leu Cys Lys Leu Asn Pro Thr Asp Asn Asp Ala
            115                 120                 125
Val Arg Gly Gln Ile Val Val Ser Leu Gln Thr Arg Asp Arg Ile Gly
            130                 135                 140
Thr Leu Gly Ser Val Val Asp Cys Arg Gly Leu Leu Asp Asn Glu Gly
145                 150                 155                 160
Ala Leu Leu Glu Asp Thr Gly Pro Gly Arg Pro Leu Ser Cys Phe Met
                165                 170                 175
Asp Glu Pro Ala Pro Tyr Thr Asp Gly Pro Gly Ala Ala Gly Gly Gly
            180                 185                 190
Pro Gly Arg Leu Val Glu Ser Pro Gly Gln Glu Gln Arg Leu Gln Ala
            195                 200                 205
Gln Arg Val Arg Gly Pro Glu Val Arg Glu His Val Gln Thr Pro Gln
            210                 215                 220
Asn Arg Ser His Gly Phe Gln Ser Gln Asp Leu Pro Glu Gly Tyr Glu
225                 230                 235                 240
Gln Arg Thr Thr Val Gln Gly Gln Val Tyr Phe Leu His Thr Gln Thr
                245                 250                 255
Gly Val Ser Thr Trp His Asp Pro Arg Ile Pro Arg Asp Leu Asn Ser
                260                 265                 270
Val Asn Cys Asp Asp Leu Gly Ser Leu Pro Ala Gly Trp Glu Val Arg
            275                 280                 285
Thr Thr Val Ser Gly Arg Ile Tyr Phe Val Asp His Asn Asn Arg Thr
            290                 295                 300
Thr Gln Phe Thr Asp Pro Arg Leu His His Ile Ile Asn His Gln Ser
305                 310                 315                 320
Gln Leu Lys Glu Pro Asn His Ala Ile Pro Val Gln Ser Asp Gly Ser
                325                 330                 335
Leu Glu Asp Gly Asp Glu Phe Pro Ala Gln Arg Tyr Glu Arg Asp Leu
                340                 345                 350
Val Gln Lys Leu Lys Val Leu Arg His Glu Leu Ser Leu Leu Gln Pro
            355                 360                 365
Gln Ala Gly His Cys Arg Val Glu Val Ser Arg Glu Glu Ile Phe Glu
            370                 375                 380
Glu Ser Tyr Arg Gln Ile Met Lys Met Arg Pro Lys Asp Leu Lys Lys
385                 390                 395                 400
Arg Leu Met Val Lys Phe Arg Gly Glu Glu Gly Leu Asp Tyr Gly Gly
                405                 410                 415
Val Ala Arg Glu Trp Leu Tyr Leu Leu Cys His Glu Met Leu Asn Pro
            420                 425                 430
Tyr Tyr Gly Leu Phe Gln Tyr Ser Thr Asp Asn Ile Tyr Thr Leu Gln
            435                 440                 445
Ile Asn Pro Asp Ser Ser Ile Asn Pro Asp His Leu Ser Tyr Phe His
            450                 455                 460
Phe Val Gly Arg Ile Met Gly Leu Ala Val Phe His Gly His Tyr Ile
465                 470                 475                 480
Asn Gly Gly Phe Thr Val Pro Phe Tyr Lys Gln Leu Leu Gly Lys Pro
                485                 490                 495
Ile Gln Leu Ser Asp Leu Glu Ser Val Asp Pro Glu Leu His Lys Ser
            500                 505                 510
Leu Val Trp Ile Leu Glu Asn Asp Ile Thr Ser Val Leu Asp His Thr
            515                 520                 525
```

```
Phe Cys Val Glu His Asn Ala Phe Gly Arg Leu Leu Gln His Glu Leu
            530                 535                 540

Lys Pro Asn Gly Lys Asn Leu Gln Val Thr Glu Glu Asn Lys Lys Glu
545                 550                 555                 560

Tyr Val Arg Leu Tyr Val Asn Trp Arg Phe Met Arg Gly Ile Glu Ala
                565                 570                 575

Gln Phe Leu Ala Leu Gln Lys Gly Phe Asn Glu Leu Ile Pro Gln His
            580                 585                 590

Leu Leu Lys Pro Phe Glu Gln Lys Glu Leu Glu Leu Ile Ile Gly Gly
        595                 600                 605

Leu Asp Lys Ile Asp Ile Ser Asp Trp Lys Ala Asn Thr Arg Leu Lys
610                 615                 620

His Cys Leu Ala Asn Ser Asn Ile Val Gln Trp Phe Trp Gln Ala Val
625                 630                 635                 640

Glu Ser Phe Asp Glu Glu Arg Arg Ala Arg Leu Leu Gln Phe Val Thr
                645                 650                 655

Gly Ser Thr Arg Val Pro Leu Gln Gly Phe Lys Ala Leu Gln Gly Ser
            660                 665                 670

Thr Gly Ala Ala Gly Pro Arg Leu Phe Thr Ile His Leu Ile Asp Ala
        675                 680                 685

Asn Thr Asp Asn Leu Pro Lys Ala His Thr Cys Phe Asn Arg Ile Asp
690                 695                 700

Ile Pro Pro Tyr Glu Ser Tyr Glu Lys Leu Tyr Glu Lys Leu Leu Thr
705                 710                 715                 720

Ala Val Glu Glu Thr Ser Gly Phe Ala Val Glu
                725                 730

<210> SEQ ID NO 8
<211> LENGTH: 766
<212> TYPE: PRT
<213> ORGANISM: Schizosaccharomyces pombe

<400> SEQUENCE: 8

Met Ser Asn Ser Ala Gln Ser Arg Arg Ile Arg Val Thr Ile Val Ala
1               5                   10                  15

Ala Asp Gly Leu Tyr Lys Arg Asp Val Phe Arg Phe Pro Asp Pro Phe
            20                  25                  30

Ala Val Leu Thr Val Asp Gly Glu Gln Thr His Thr Thr Thr Ala Ile
        35                  40                  45

Lys Lys Thr Leu Asn Pro Tyr Trp Asn Glu Thr Phe Glu Val Asn Val
50                  55                  60

Thr Asp Asn Ser Thr Ile Ala Ile Gln Val Phe Asp Gln Lys Lys Phe
65                  70                  75                  80

Lys Lys Lys Gly Gln Gly Phe Leu Gly Val Ile Asn Leu Arg Val Gly
                85                  90                  95

Asp Val Leu Asp Leu Ala Ile Gly Gly Asp Glu Met Leu Thr Arg Asp
            100                 105                 110

Leu Lys Lys Ser Asn Glu Asn Thr Val Val His Gly Lys Ile Ile Ile
        115                 120                 125

Asn Leu Ser Thr Thr Ala Gln Ser Thr Leu Gln Val Pro Ser Ser Ala
130                 135                 140

Ala Ser Gly Ala Arg Thr Gln Arg Thr Ser Ile Thr Asn Asp Pro Gln
145                 150                 155                 160

Ser Ser Lys Ser Ser Ser Val Ser Arg Asn Pro Ala Ser Ser Arg Ala
```

-continued

```
                165                 170                 175
Gly Ser Pro Thr Arg Asp Asn Ala Pro Ala Ser Pro Ala Ser Ser
            180                 185                 190
Glu Pro Arg Thr Phe Ser Ser Phe Glu Asp Gln Tyr Gly Arg Leu Pro
                195                 200                 205
Pro Gly Trp Glu Arg Arg Thr Asp Asn Leu Gly Arg Thr Tyr Tyr Val
            210                 215                 220
Asp His Asn Thr Arg Ser Thr Thr Trp Ile Arg Pro Asn Leu Ser Ser
225                 230                 235                 240
Val Ala Gly Ala Ala Ala Glu Leu His Ser Ser Ala Ser Ser Ala
                245                 250                 255
Asn Val Thr Glu Gly Val Gln Pro Ser Ser Asn Ala Ala Arg Arg
            260                 265                 270
Thr Glu Ala Ser Val Leu Thr Ser Asn Ala Thr Ala Gly Ser Gly
                275                 280                 285
Glu Leu Pro Pro Gly Trp Glu Gln Arg Tyr Thr Pro Glu Gly Arg Pro
            290                 295                 300
Tyr Phe Val Asp His Asn Thr Arg Thr Thr Thr Trp Val Asp Pro Arg
305                 310                 315                 320
Arg Gln Gln Tyr Ile Arg Ser Tyr Gly Gly Pro Asn Asn Ala Thr Ile
                325                 330                 335
Gln Gln Gln Pro Val Ser Gln Leu Gly Pro Leu Pro Ser Gly Trp Glu
            340                 345                 350
Met Arg Leu Thr Asn Thr Ala Arg Val Tyr Phe Val Asp His Asn Thr
                355                 360                 365
Lys Thr Thr Thr Trp Asp Asp Pro Arg Leu Pro Ser Ser Leu Asp Gln
            370                 375                 380
Asn Val Pro Gln Tyr Lys Arg Asp Phe Arg Arg Lys Leu Ile Tyr Phe
385                 390                 395                 400
Leu Ser Gln Pro Ala Leu His Pro Leu Pro Gly Gln Cys His Ile Lys
                405                 410                 415
Val Arg Arg Asn His Ile Phe Glu Asp Ser Tyr Ala Glu Ile Met Arg
            420                 425                 430
Gln Ser Ala Thr Asp Leu Lys Lys Arg Leu Met Ile Lys Phe Asp Gly
            435                 440                 445
Glu Asp Gly Leu Asp Tyr Gly Gly Leu Ser Arg Glu Tyr Phe Phe Leu
            450                 455                 460
Leu Ser His Glu Met Phe Asn Pro Phe Tyr Cys Leu Phe Glu Tyr Ser
465                 470                 475                 480
Ser Val Asp Asn Tyr Thr Leu Gln Ile Asn Pro His Ser Gly Ile Asn
                485                 490                 495
Pro Glu His Leu Asn Tyr Phe Lys Phe Ile Gly Arg Val Ile Gly Leu
            500                 505                 510
Ala Ile Phe His Arg Arg Phe Val Asp Ala Phe Phe Val Val Ser Phe
            515                 520                 525
Tyr Lys Met Ile Leu Gln Lys Lys Val Thr Leu Gln Asp Met Glu Ser
            530                 535                 540
Met Asp Ala Glu Tyr Tyr Arg Ser Leu Val Trp Ile Leu Asp Asn Asp
545                 550                 555                 560
Ile Thr Gly Val Leu Asp Leu Thr Phe Ser Val Glu Asp Asn Cys Phe
                565                 570                 575
Gly Glu Val Val Thr Ile Asp Leu Lys Pro Asn Gly Arg Asn Ile Glu
            580                 585                 590
```

-continued

```
Val Thr Glu Glu Asn Lys Arg Glu Tyr Val Asp Leu Val Thr Val Trp
        595                 600                 605

Ile Gln Lys Arg Ile Glu Glu Gln Phe Asn Ala Phe His Glu Gly Phe
    610                 615                 620

Ser Glu Leu Ile Pro Gln Leu Ile Asn Val Phe Asp Glu Arg Glu
625                 630                 635                 640

Leu Glu Leu Leu Ile Gly Gly Ile Ser Glu Ile Asp Met Glu Asp Trp
                    645                 650                 655

Lys Lys His Lys Asp Tyr Arg Ser Tyr Ser Glu Asn Asp Gln Ile Ile
                660                 665                 670

Lys Trp Phe Trp Glu Leu Met Asp Glu Trp Ser Asn Glu Lys Lys Ser
        675                 680                 685

Arg Leu Leu Gln Phe Thr Thr Gly Thr Ser Arg Ile Pro Val Asn Gly
    690                 695                 700

Phe Lys Asp Leu Gln Gly Ser Asp Gly Pro Arg Lys Phe Thr Ile Glu
705                 710                 715                 720

Lys Ala Gly Glu Pro Asn Lys Leu Pro Lys Ala His Thr Cys Phe Asn
                725                 730                 735

Arg Leu Asp Leu Pro Pro Tyr Thr Ser Lys Lys Asp Leu Asp His Lys
                740                 745                 750

Leu Ser Ile Ala Val Glu Glu Thr Ile Gly Phe Gly Gln Glu
        755                 760                 765

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Consensus

<400> SEQUENCE: 9

Leu Glu Ser Pro Pro Pro Pro Tyr Ser Arg Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Consensus

<400> SEQUENCE: 10

Leu Glu Ser Pro Pro Pro Pro Ala Ser Arg Tyr
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Consensus

<400> SEQUENCE: 11

Leu Glu Ser Ser Arg Tyr
1               5

<210> SEQ ID NO 12
<211> LENGTH: 4
<212> TYPE: PRT
<213> ORGANISM: Artificial Sequence
<220> FEATURE:
```

```
-continued

<223> OTHER INFORMATION: Description of Artificial Sequence: Consensus
<220> FEATURE:
<221> NAME/KEY: misc_feature
<222> LOCATION: 3
<223> OTHER INFORMATION: Xaa = Any amino acid

<400> SEQUENCE: 12

Pro Pro Xaa Tyr
1

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Consensus

<400> SEQUENCE: 13

Pro Pro Pro Pro Tyr
1               5
```